United States Patent
Hansen et al.

(10) Patent No.: US 11,622,719 B2
(45) Date of Patent: Apr. 11, 2023

(54) SENSOR ASSEMBLY PART, BASE PLATE AND MONITOR DEVICE OF A MEDICAL SYSTEM AND ASSOCIATED METHOD

(71) Applicant: Coloplast A/S, Humlebaek (DK)

(72) Inventors: Jais Ask Hansen, Jaegerspris (DK); Niels Hvid, Vedbaek (DK); Finn Speiermann, Virum (DK); Lars Erup Larsen, Maaloev (DK)

(73) Assignee: Coloplast A/S, Humlebaek (DK)

( * ) Notice: Subject to any disclaimer, the term of this patent is extended or adjusted under 35 U.S.C. 154(b) by 311 days.

(21) Appl. No.: 16/955,065

(22) PCT Filed: Dec. 20, 2018

(86) PCT No.: PCT/DK2018/050403
§ 371 (c)(1),
(2) Date: Jun. 18, 2020

(87) PCT Pub. No.: WO2019/120447
PCT Pub. Date: Jun. 27, 2019

(65) Prior Publication Data
US 2020/0383637 A1    Dec. 10, 2020

(30) Foreign Application Priority Data

Dec. 22, 2017 (DK) .......................... PA 2017 70989
Dec. 22, 2017 (DK) .......................... PA 2017 70990
(Continued)

(51) Int. Cl.
*A61B 5/00* (2006.01)
*A61B 90/96* (2016.01)
(Continued)

(52) U.S. Cl.
CPC .......... *A61B 5/6802* (2013.01); *A61B 5/0002* (2013.01); *A61B 5/6832* (2013.01);
(Continued)

(58) Field of Classification Search
CPC ........ A61F 5/445; A61F 5/4404; A61F 5/443; A61B 5/6802; A61B 5/0002;
(Continued)

(56) References Cited

U.S. PATENT DOCUMENTS

| | | |
|---|---|---|
| 2,327,514 A | 8/1943 | Fenwick |
| 2,542,233 A | 2/1951 | Carroll |

(Continued)

FOREIGN PATENT DOCUMENTS

| | | |
|---|---|---|
| CN | 203786580 U | 8/2014 |
| CN | 104902399 A | 9/2015 |

(Continued)

*Primary Examiner* — Joseph M Dietrich
*Assistant Examiner* — Michael T. Holtzclaw
(74) *Attorney, Agent, or Firm* — Coloplast Corp., Coloplast A/S; Nick Baumann

(57) ABSTRACT

Disclosed is a sensor assembly part for a base plate of an ostomy system and an associated method for operating a monitor device, wherein the sensor assembly part comprises: an electrode assembly including a plurality of electrodes, each electrode including a sensing part and a connection part, the connection part being configured to electrically couple the sensing part to a monitor device of the ostomy system; a monitor interface configured to couple the sensor assembly part to the monitor device; and a first identifier element configured to be queried by the monitor device.

20 Claims, 18 Drawing Sheets

(30) Foreign Application Priority Data

Dec. 22, 2017 (DK) .................... PA 2017 71002
Dec. 22, 2017 (DK) .................... PA 2017 71006

(51) Int. Cl.

| | |
|---|---|
| A61B 90/98 | (2016.01) |
| A61F 5/44 | (2006.01) |
| A61F 5/443 | (2006.01) |
| G16H 40/63 | (2018.01) |

(52) U.S. Cl.

CPC .......... *A61B 5/7405* (2013.01); *A61B 5/7455* (2013.01); *A61B 90/96* (2016.02); *A61B 90/98* (2016.02); *A61F 5/443* (2013.01); *A61F 5/4404* (2013.01); *G16H 40/63* (2018.01); *A61B 2562/227* (2013.01)

(58) Field of Classification Search

CPC ... A61B 5/6832; A61B 5/7405; A61B 5/7455; A61B 90/96; A61B 90/98; A61B 2562/227; G16H 40/63; G16H 20/40

See application file for complete search history.

(56) References Cited

U.S. PATENT DOCUMENTS

| | | | |
|---|---|---|---|
| 2,544,579 | A | 3/1951 | Ardner |
| 3,214,502 | A | 10/1965 | Schaar |
| 3,832,510 | A | 8/1974 | Pfau et al. |
| 3,915,171 | A | 10/1975 | Shermeta |
| 3,941,133 | A | 3/1976 | Chen |
| 4,231,369 | A | 11/1980 | Sorensen et al. |
| 4,372,308 | A | 2/1983 | Steer et al. |
| 4,449,970 | A | 5/1984 | Bevan et al. |
| 4,668,227 | A | 5/1987 | Kay |
| 4,754,264 | A | 6/1988 | Okada et al. |
| 4,775,374 | A | 10/1988 | Cilento et al. |
| 4,834,731 | A | 5/1989 | Nowak et al. |
| 4,973,323 | A | 11/1990 | Kaczmarek et al. |
| 4,982,742 | A | 1/1991 | Claude |
| 5,013,307 | A | 5/1991 | Broida |
| 5,016,645 | A | 5/1991 | Williams et al. |
| 5,051,259 | A | 9/1991 | Olsen et al. |
| 5,074,851 | A | 12/1991 | Plass et al. |
| 5,111,812 | A | 5/1992 | Swanson et al. |
| 5,167,650 | A | 12/1992 | Johnsen et al. |
| 5,237,995 | A | 8/1993 | Cano |
| 5,318,543 | A | 6/1994 | Ross et al. |
| 5,358,488 | A | 10/1994 | Suriyapa |
| 5,486,158 | A | 1/1996 | Samuelsen |
| 5,570,082 | A | 10/1996 | Mahgerefteh et al. |
| 5,593,397 | A | 1/1997 | La Gro |
| 5,672,163 | A | 9/1997 | Ferreira et al. |
| 5,677,221 | A | 10/1997 | Tseng |
| 5,704,905 | A | 1/1998 | Jensen et al. |
| 5,790,036 | A | 8/1998 | Fisher et al. |
| 5,800,415 | A | 9/1998 | Olsen |
| 5,816,252 | A | 10/1998 | Faries, Jr. et al. |
| 5,834,009 | A | 11/1998 | Sawers et al. |
| 5,879,292 | A | 3/1999 | Sternberg et al. |
| 5,942,186 | A | 8/1999 | Sanada et al. |
| 6,015,399 | A | 1/2000 | Mracna et al. |
| 6,025,725 | A | 2/2000 | Gershenfeld et al. |
| 6,057,689 | A | 5/2000 | Saadat |
| 6,103,033 | A | 8/2000 | Say et al. |
| 6,135,986 | A | 10/2000 | Leisner et al. |
| 6,171,289 | B1 * | 1/2001 | Millot .................... A61F 5/443 604/336 |
| 6,206,864 | B1 | 3/2001 | Kavanagh et al. |
| 6,407,308 | B1 | 6/2002 | Roe et al. |
| 6,433,244 | B1 | 8/2002 | Roe et al. |
| 6,482,491 | B1 | 11/2002 | Samuelsen et al. |
| 6,485,476 | B1 | 11/2002 | Dyck et al. |
| 6,520,943 | B1 | 2/2003 | Wagner |
| 6,659,989 | B1 | 12/2003 | Otto |
| 6,764,474 | B2 | 7/2004 | Nielsen et al. |
| 7,066,919 | B1 | 6/2006 | Sauerland et al. |
| 7,150,728 | B2 | 12/2006 | Hansen et al. |
| 7,166,091 | B1 | 1/2007 | Zeltner |
| 7,199,501 | B2 | 4/2007 | Pei et al. |
| 7,214,217 | B2 | 5/2007 | Pedersen et al. |
| 7,326,190 | B2 | 2/2008 | Botten |
| 7,341,578 | B2 | 3/2008 | Bulow et al. |
| 7,347,844 | B2 | 3/2008 | Cline et al. |
| 7,367,965 | B2 | 5/2008 | Poulsen et al. |
| 7,559,922 | B2 | 7/2009 | Botten |
| 7,625,362 | B2 | 12/2009 | Boergringer et al. |
| 7,641,612 | B1 | 1/2010 | McCall |
| 7,670,289 | B1 | 3/2010 | McCall |
| 7,943,812 | B2 | 5/2011 | Stroebeck et al. |
| 7,981,098 | B2 | 7/2011 | Boergringer et al. |
| 3,061,360 | A1 | 11/2011 | Locke et al. |
| 8,277,427 | B2 | 10/2012 | Edvardsen et al. |
| 8,319,003 | B2 | 11/2012 | Olsen et al. |
| 8,398,575 | B1 | 3/2013 | McCall |
| 8,398,603 | B2 | 3/2013 | Thirstrup et al. |
| 8,399,732 | B2 | 3/2013 | Oelund et al. |
| 8,409,158 | B2 | 4/2013 | Edvardsen et al. |
| 8,449,471 | B2 | 5/2013 | Tran |
| 8,500,718 | B2 | 8/2013 | Locke et al. |
| 8,632,492 | B2 | 1/2014 | Delegge |
| 8,680,991 | B2 | 3/2014 | Tran |
| 8,684,982 | B2 | 4/2014 | Nguyen-Demary et al. |
| 8,740,865 | B2 | 6/2014 | Krystek et al. |
| 8,795,257 | B2 | 8/2014 | Coulthard et al. |
| 8,821,464 | B2 | 9/2014 | Hanuka et al. |
| 8,975,465 | B2 | 3/2015 | Hong et al. |
| 9,046,085 | B2 | 6/2015 | Schoess et al. |
| 9,066,812 | B2 | 6/2015 | Edvardsen et al. |
| 9,216,104 | B2 | 12/2015 | Thirstrup et al. |
| 9,308,332 | B2 | 4/2016 | Heppe |
| 9,322,797 | B1 | 4/2016 | Lastinger et al. |
| 9,629,964 | B2 | 4/2017 | Wuepper |
| 9,693,908 | B2 | 7/2017 | Eriksson et al. |
| 9,770,359 | B2 | 9/2017 | Edvardsen et al. |
| 9,788,991 | B2 | 10/2017 | Bird |
| 9,867,934 | B2 | 1/2018 | Heppe |
| 9,928,341 | B2 | 3/2018 | Angelides |
| 10,016,298 | B2 | 7/2018 | Thirstrup et al. |
| D826,740 | S | 8/2018 | Stevens et al. |
| 10,500,084 | B2 | 12/2019 | Hansen et al. |
| 10,531,977 | B2 | 1/2020 | Schoess et al. |
| 10,646,370 | B2 | 5/2020 | Keleny et al. |
| 10,792,184 | B2 | 10/2020 | Hvid et al. |
| 10,799,385 | B2 | 10/2020 | Hansen et al. |
| 10,849,781 | B2 | 12/2020 | Hansen et al. |
| 10,874,541 | B2 | 12/2020 | Seres et al. |
| 10,987,243 | B2 | 4/2021 | Thirstrup et al. |
| 11,096,818 | B2 | 8/2021 | Thirstrup et al. |
| 11,135,084 | B2 | 10/2021 | Seres et al. |
| 11,406,525 | B2 | 8/2022 | Seres et al. |
| 11,471,318 | B2 | 10/2022 | Hansen et al. |
| 2002/0019615 | A1 | 2/2002 | Roe et al. |
| 2003/0132763 | A1 | 7/2003 | Ellenz |
| 2003/0169032 | A1 | 9/2003 | Minchole et al. |
| 2004/0006320 | A1 | 1/2004 | Buglino et al. |
| 2004/0030305 | A1 | 2/2004 | Sakamoto |
| 2004/0036484 | A1 | 2/2004 | Tamai |
| 2004/0049145 | A1 | 3/2004 | Flick |
| 2004/0078219 | A1 | 4/2004 | Kaylor et al. |
| 2004/0100376 | A1 | 5/2004 | Lye et al. |
| 2004/0106908 | A1 | 6/2004 | Leise, Jr. et al. |
| 2004/0111072 | A1 | 6/2004 | McKissick |
| 2004/0133175 | A1 | 7/2004 | Hagedom-Olsen |
| 2004/0171999 | A1 | 9/2004 | Andersen et al. |
| 2004/0193122 | A1 | 9/2004 | Cline et al. |
| 2004/0193123 | A1 | 9/2004 | Fenton |
| 2004/0216833 | A1 | 11/2004 | Fleming et al. |
| 2005/0054997 | A1 | 3/2005 | Bugling et al. |
| 2005/0065488 | A1 | 3/2005 | Elliott |
| 2005/0070863 | A1 | 3/2005 | Von Bulow et al. |
| 2005/0085779 | A1 | 4/2005 | Poulsen et al. |
| 2005/0101841 | A9 | 5/2005 | Kaylor et al. |

(56) References Cited

U.S. PATENT DOCUMENTS

| | | |
|---|---|---|
| 2005/0240163 A1 | 10/2005 | Andersen |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | McMichael |
| 2006/0194324 A1 | 8/2006 | Faries, Jr. et al. |
| 2006/0271002 A1 | 11/2006 | Botten |
| 2007/0035405 A1 | 2/2007 | Wada et al. |
| 2007/0038044 A1* | 2/2007 | Dobbies ............ A61B 5/1495 600/316 |
| 2007/0135782 A1 | 6/2007 | Bager et al. |
| 2007/0185464 A1 | 8/2007 | Fattman et al. |
| 2008/0038536 A1 | 2/2008 | Stroebech et al. |
| 2008/0071214 A1 | 3/2008 | Locke et al. |
| 2008/0075934 A1 | 3/2008 | Barlow, Jr. et al. |
| 2008/0091154 A1 | 4/2008 | Botten |
| 2008/0140057 A1 | 6/2008 | Wood et al. |
| 2008/0234641 A1 | 9/2008 | Locke et al. |
| 2008/0275327 A1 | 11/2008 | Faarbaek et al. |
| 2008/0278337 A1 | 11/2008 | Huang et al. |
| 2008/0300559 A1 | 12/2008 | Gustafdon et al. |
| 2008/0306459 A1 | 12/2008 | Albrectsen |
| 2009/0012501 A1 | 1/2009 | Boehringer et al. |
| 2009/0118600 A1 | 5/2009 | Oritz et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0227969 A1 | 9/2009 | Jaeb et al. |
| 2009/0247970 A1 | 10/2009 | Keleny et al. |
| 2010/0010460 A1 | 1/2010 | Butler |
| 2010/0030167 A1 | 2/2010 | Thirstrup et al. |
| 2010/0036206 A1 | 2/2010 | Lorio |
| 2010/0072271 A1 | 3/2010 | Thorstensson |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2012/0013130 A1 | 1/2012 | Jung |
| 2012/0143154 A1 | 6/2012 | Edvardsen et al. |
| 2012/0143155 A1 | 6/2012 | Edvardsen et al. |
| 2012/0253224 A1 | 10/2012 | Mir et al. |
| 2012/0258302 A1 | 10/2012 | Hunt et al. |
| 2012/0259230 A1 | 10/2012 | Riley |
| 2012/0283678 A1 | 11/2012 | Nguyen-Demary et al. |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Shcertiger et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0261575 A1 | 10/2013 | Kiyoshi |
| 2013/0303867 A1 | 11/2013 | Elfstrom et al. |
| 2013/0324952 A1 | 12/2013 | Krystek et al. |
| 2013/0324955 A1 | 12/2013 | Wong et al. |
| 2014/0051946 A1 | 2/2014 | Arne et al. |
| 2014/0200538 A1 | 7/2014 | Euliano et al. |
| 2014/0236111 A1 | 8/2014 | Casado et al. |
| 2014/0236335 A1 | 8/2014 | Lewia et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0118759 A1* | 4/2015 | Blackburn ............ G01N 33/66 436/95 |
| 2015/0231802 A1 | 8/2015 | Quan et al. |
| 2015/0250639 A1 | 9/2015 | Thirstrup et al. |
| 2015/0257923 A1* | 9/2015 | Thirstrup ............ A61F 13/42 604/318 |
| 2015/0342777 A1 | 12/2015 | Seres et al. |
| 2015/0374896 A1 | 12/2015 | Du et al. |
| 2016/0084869 A1 | 3/2016 | Yuen et al. |
| 2016/0158056 A1 | 6/2016 | Davis et al. |
| 2016/0158969 A1 | 6/2016 | McLane et al. |
| 2016/0166438 A1 | 6/2016 | Rovaniemi |
| 2016/0218555 A1 | 7/2016 | Slaby et al. |
| 2016/0235581 A1 | 8/2016 | Keleny et al. |
| 2016/0278990 A1 | 9/2016 | Chen |
| 2016/0284084 A1 | 9/2016 | Gurcan et al. |
| 2016/0305776 A1 | 10/2016 | Martensson et al. |
| 2016/0310140 A1 | 10/2016 | Belson et al. |
| 2016/0310329 A1 | 10/2016 | Patel et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079576 A1 | 3/2017 | Stroebech et al. |
| 2017/0112658 A1 | 4/2017 | Hosono |
| 2017/0140103 A1 | 5/2017 | Angelides |
| 2017/0156920 A1 | 6/2017 | Hunt et al. |
| 2017/0262986 A1 | 9/2017 | Xiong et al. |
| 2017/0340474 A1 | 11/2017 | Thirstrup et al. |
| 2017/0348137 A1 | 12/2017 | Hvid et al. |
| 2017/0360592 A1 | 12/2017 | Carrubba |
| 2018/0049667 A1 | 2/2018 | Heppe |
| 2018/0055359 A1 | 3/2018 | Shamim et al. |
| 2018/0171183 A1 | 6/2018 | Sakurai et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0374163 A1 | 12/2019 | Faarbaek et al. |
| 2019/0374372 A1 | 12/2019 | Seres et al. |
| 2020/0100931 A1 | 4/2020 | Schoess et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Herencia |
| 2020/0306074 A1 | 10/2020 | Speiermann et al. |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |

(56) References Cited

U.S. PATENT DOCUMENTS

| | | |
|---|---|---|
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0128364 A1 | 5/2021 | Cole et al. |
| 2021/0177642 A1 | 6/2021 | Andersen et al. |
| 2021/0212855 A1 | 7/2021 | Hansen et al. |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0386368 A1 | 12/2021 | Carlsson et al. |
| 2022/0000652 A1 | 1/2022 | Thirstrup et al. |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |

FOREIGN PATENT DOCUMENTS

| | | | |
|---|---|---|---|
| CN | 104980878 A | | 10/2015 |
| CN | 105588856 A | | 5/2016 |
| CN | 206271160 U | | 6/2017 |
| CN | 206450708 U | | 8/2017 |
| DE | 3437950 A1 | | 4/1985 |
| DE | 3836590 A1 | | 5/1990 |
| DE | 19900611 C1 | | 7/2000 |
| DE | 102011014321 A1 | | 9/2012 |
| DE | 102011076219 A1 | | 11/2012 |
| EP | 0168967 A1 | | 1/1986 |
| EP | 0373782 A1 | | 6/1990 |
| EP | 0416397 A1 | | 3/1991 |
| EP | 0800804 A1 | | 10/1997 |
| EP | 1275357 A2 | | 1/2003 |
| EP | 1188157 B1 | | 12/2005 |
| EP | 2108345 A1 | | 10/2009 |
| EP | 2489561 A2 | | 8/2012 |
| EP | 2601915 A1 | | 6/2013 |
| EP | 2654646 B1 | | 7/2016 |
| EP | 3213727 A1 | | 9/2017 |
| EP | 3064179 B1 | | 9/2021 |
| GB | 2219679 A | | 12/1989 |
| GB | 2465742 A | | 6/2010 |
| GB | 2542093 A | | 3/2017 |
| JP | H0474882 A | | 3/1992 |
| JP | H06152077 A | | 5/1994 |
| JP | H0910184 A | | 1/1997 |
| JP | 2000093448 A | | 4/2000 |
| JP | 2001087299 A | | 4/2001 |
| JP | 2002055074 A | | 2/2002 |
| JP | 2002224093 A | | 8/2002 |
| JP | 2005323981 A | | 11/2005 |
| JP | 2007319561 A | | 12/2007 |
| JP | 2014033745 A | | 2/2014 |
| JP | 2014054368 A | | 3/2014 |
| JP | 2014507182 A | | 3/2014 |
| KR | 20120003987 A | | 1/2012 |
| RU | 2527155 C2 | | 8/2014 |
| TW | 201201783 A | | 1/2012 |
| WO | 1994015562 A1 | | 7/1994 |
| WO | 1997010012 A1 | | 3/1997 |
| WO | 1999033037 A1 | | 7/1999 |
| WO | 1999036017 A1 | | 7/1999 |
| WO | 2000079497 A1 | | 12/2000 |
| WO | 2001013830 A1 | | 3/2001 |
| WO | 2001050996 A1 | | 7/2001 |
| WO | 2002052302 A2 | | 7/2002 |
| WO | 2002099765 A1 | | 12/2002 |
| WO | 2005082271 A2 | | 9/2005 |
| WO | 2006008866 A1 | | 1/2006 |
| WO | 2006094513 A2 | | 9/2006 |
| WO | 2007000168 A1 | | 1/2007 |
| WO | 2007059774 A2 | | 5/2007 |
| WO | 2007098762 A1 | | 9/2007 |
| WO | 2007133555 A2 | | 11/2007 |
| WO | 2008057884 A2 | | 5/2008 |
| WO | 2009006900 A1 | | 1/2009 |
| WO | 2009052496 A1 | | 4/2009 |
| WO | 2009112912 A2 | | 9/2009 |
| WO | 2011003421 A1 | | 1/2011 |
| WO | 2011004165 A1 | | 1/2011 |
| WO | 2011105701 A2 | | 9/2011 |
| WO | 2011161254 A2 | | 12/2011 |
| WO | 2012068386 A1 | | 5/2012 |
| WO | 2012076022 A2 | | 6/2012 |
| WO | 2013013197 A1 | | 1/2013 |
| WO | 2014004207 A1 | | 1/2014 |
| WO | 2014086369 A1 | | 6/2014 |
| WO | 2015007284 A1 | | 1/2015 |
| WO | 2015014774 A1 | | 2/2015 |
| WO | 2015084462 A1 | | 6/2015 |
| WO | 2015094064 A1 | | 6/2015 |
| WO | 2016166731 A1 | | 10/2016 |
| WO | 2017023794 A1 | | 2/2017 |
| WO | 2017062042 A1 | | 4/2017 |
| WO | 2017067558 A1 | | 4/2017 |
| WO | 2017067560 A1 | | 4/2017 |
| WO | 2017088153 A1 | | 6/2017 |
| WO | 2017136696 A1 | | 8/2017 |
| WO | 2017190752 A1 | | 11/2017 |
| WO | 2018028756 A1 | | 2/2018 |
| WO | 2019094635 A1 | | 5/2019 |
| WO | 2019161863 A1 | | 8/2019 |

\* cited by examiner

SENSOR ASSEMBLY PART, BASE PLATE AND MONITOR DEVICE OF A MEDICAL SYSTEM AND ASSOCIATED METHOD

The present disclosure relates to an ostomy system, devices thereof and method for monitoring an ostomy appliance. In particular, the present disclosure relates to a sensor assembly and/or a base plate of an ostomy system and a monitor device and associated method for.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
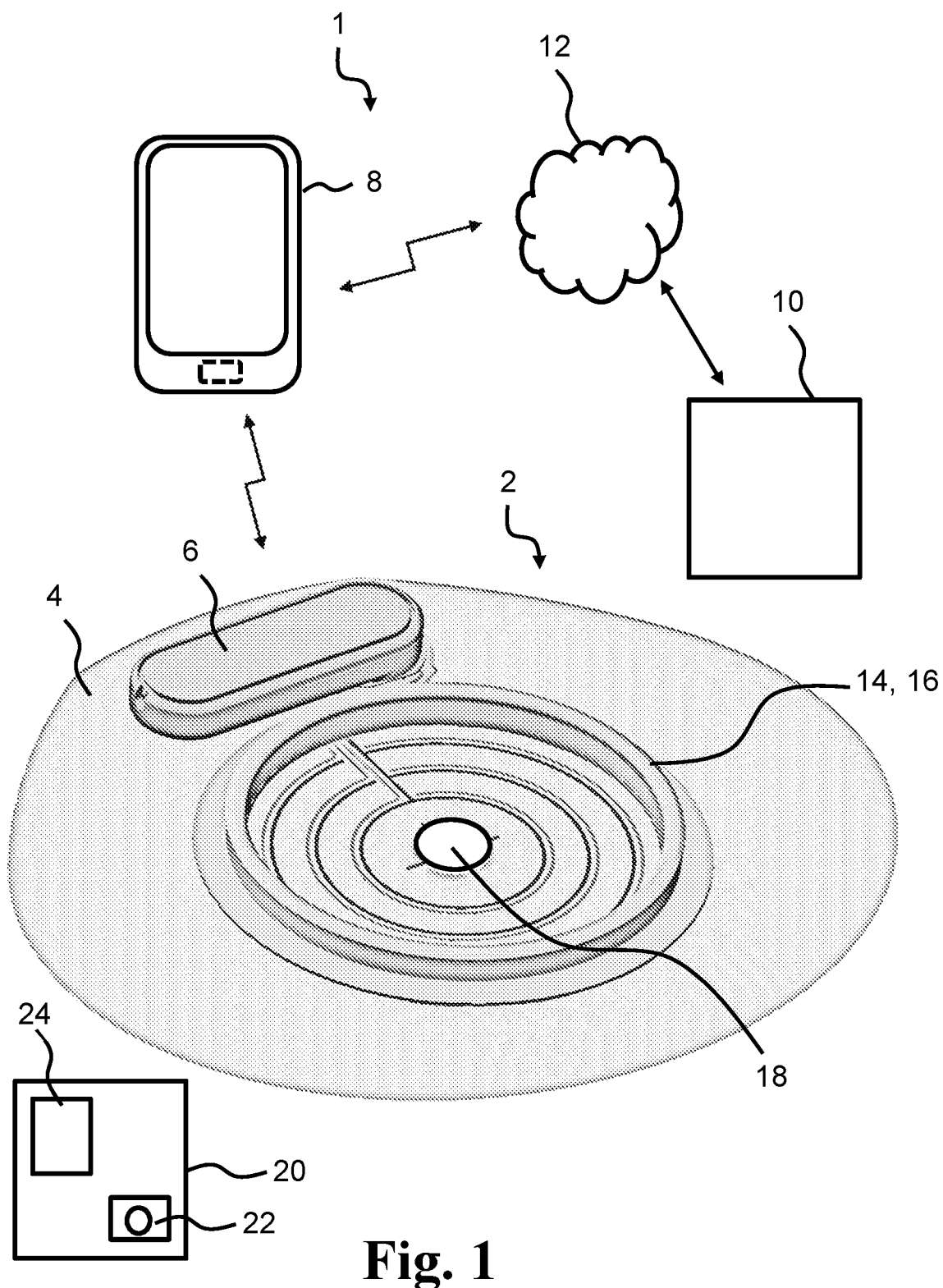
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The ostomy appliance may comprise a sensor assembly part, such as a sensor assembly part to be applied to a base plate. For example, to allow an arbitrary base plate, such as a conventional base plate, to achieve the features as described herein. It is emphasized, that any of the features as described with respect to the base plate herein may be provided by a sensor assembly part to be applied to a base plate, e.g. by the user.

The base plate and/or the sensor assembly part may comprise a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate and/or the sensor assembly part to the skin surface of a user. The first adhesive layer may have a stomal opening, such as a first adhesive stomal opening, with a center point.

The first adhesive layer may be made of a first composition. The first composition may comprise one or more polyisobutenes and/or styrene-isoprene-styrene. The first composition may comprise one or more hydrocolloids. The first composition may comprise one or more water soluble or water swellable hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethylcellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate and/or the sensor assembly part may comprise a second layer. The second layer may be an adhesive layer, also denoted rim adhesive layer. The second layer may have a second radial extension that is larger than a first radial extension of the first adhesive layer at least in a first angular range of the base plate and/or the sensor assembly part. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening, such as a second layer stomal opening and/or a second adhesive stomal opening, with a center point.

The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate and/or the sensor assembly part may comprise one or more electrodes, such as a plurality of electrodes, such as two, three, four, five, six, seven or more electrodes. The sensor assembly part may be applied to the base plate, such as to provide the base plate with the one or more electrodes.

The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals. An electrode may comprise one or more conductor parts and/or one or more sensing parts. A conductor part may be considered part of an electrode connecting two or more sensing parts, and/or connecting a sensing part with a connection part of the respective electrode. A sensing part may be considered a part of the electrode being suitable for sensing, e.g. liquid, such as liquid content, and/or output, such as output resulting from a leakage, or an imminent leakage. The sensing part may be suitable for sensing e.g. by its shape, said shape potentially being circular, oval, or rectangular. Thus, the conductor part may conduct a signal arising from the sensing part. An electrode may comprise alternating conductor parts and sensing parts. The electrode assembly may be arranged between the first adhesive layer and the second adhesive layer. The base plate and/or the sensor assembly part, e.g. the electrode assembly, may comprise a first electrode, a second electrode and optionally a third electrode. The base plate and/or the sensor assembly part, e.g. the electrode assembly, may comprise a fourth electrode and/or a fifth electrode. The base plate and/or the sensor assembly part, e.g. the electrode assembly, optionally comprises a sixth electrode. The base plate and/or the sensor assembly part, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode. The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair. The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly, such as the support layer of the electrode assembly, may have a stomal opening, such as an electrode assembly stomal opening and/or a support layer stomal opening, with a center point.

The support layer may comprise polymeric (e.g. polyurethane, PTFE, PVDF) and/or ceramic (e.g. alumina, silica) materials. In one or more exemplary base plates and/or sensor assembly parts, the support layer is made of thermoplastic polyurethane (TPU). The support layer material may be made of or comprise one or more of polyester, a thermoplastic elastomer (TPE), polyimide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part, such as the electrode assembly may comprise a masking element configured to insulate at least parts of the electrodes from the first adhesive layer of the base plate and/or the sensor assembly part. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates and/or sensor assembly parts, the masking element is made of or comprises thermoplastic polyurethane (TPU). In one or more exemplary base plates and/or sensor assembly parts, the masking element is made of or comprises polyester. The masking element material may be made of or comprise one or more of polyester, a thermoplastic elastomer (TPE), polyimide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part may comprise a first intermediate element. The first intermediate element may be arranged between the electrodes/electrode layer and the first adhesive layer and/or between the second layer and the first adhesive layer. The first intermediate layer may be made of an insulating material.

The base plate and/or the sensor assembly part may comprise a release liner. The release liner is a protective layer that protects adhesive layer(s) during transport and storage and is peeled off by the user prior to applying the base plate and/or the sensor assembly part on the skin. The release liner may have a stomal opening, such as a release liner stomal opening, with a center point.

The base plate and/or the sensor assembly part may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening, such as a top layer stomal opening, with a center point. The top layer may have a thickness in the range from 0.01 mm to 1.0 mm, e.g. in the range from 0.02 mm to 0.2 mm, such as 0.04 mm.

The base plate and/or the sensor assembly part comprises a monitor interface. The monitor interface may be configured for electrically and/or mechanically connecting the ostomy appliance (base plate and/or sensor assembly part) to the monitor device. The monitor interface may be configured for wirelessly connecting the ostomy appliance (base plate and/or sensor assembly part) to the monitor device. Thus, the monitor interface of the base plate and/or the sensor assembly part may be configured to electrically and/or mechanically couple the ostomy appliance and the monitor device.

The monitor interface of the base plate and/or the sensor assembly part may comprise, e.g. as part of a first connector of the monitor interface, a coupling part for forming a mechanical connection, such as a releasable coupling between the monitor device and the base plate and/or the sensor assembly part. The coupling part may be configured to engage with a coupling part of the monitor device for releasably coupling the monitor device to the base plate and/or the sensor assembly part.

The monitor interface of the base plate and/or the sensor assembly part may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate and/or the sensor assembly part, such as of the electrode assembly. The first intermediate element may be arranged between the terminal elements and the first adhesive layer. The first intermediate element may cover or overlap terminal element(s) of the base plate and/or the sensor assembly part when seen in the axial direction. Thus, the first adhesive layer may be protected or experience more evenly distributed mechanical stress from the terminal elements of the base plate and/or the sensor assembly part, in turn reducing the risk of terminal elements penetrating or otherwise damaging the first adhesive layer. The first intermediate element may protect or mechanically and/or electrically shield the first adhesive layer from the terminal elements of the base plate and/or the sensor assembly part.

The base plate may comprise a coupling ring or other coupling member for coupling an ostomy pouch to the base plate (two-part ostomy appliance). The center point may be defined as a center of the coupling ring.

The base plate and/or the sensor assembly part may have a stomal opening with a center point. The stomal opening of the base plate and/or the sensor assembly part may be formed collectively of stomal opening(s) of the layers of the base plate and/or the sensor assembly part, such as of the top layer, the first adhesive layer, the second layer and/or the sensor assembly part. The stomal opening(s) of the layers of the base plate and/or the sensor assembly part, such as of the top layer, the first adhesive layer, the second layer and/or the sensor assembly part may be aligned to form the stomal opening of the base plate and/or the sensor assembly part. The stomal opening may be a through-going passage of the base plate and/or the sensor assembly part. The stomal opening may be arranged substantially in the center of the base plate and/or the sensor assembly part. The stomal opening(s) of the layers of the base plate and/or the sensor assembly part may be arranged substantially in the center of the respective layer. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from a proximal side of the base plate and/or sensor assembly part to a distal side of the base plate and/or sensor assembly part. The size and/or shape of the stomal opening may typically be adjusted by the user or nurse before application of the ostomy appliance to accommodate the user's stoma. In one or more exemplary base plates and/or sensor assembly parts, the user forms the stomal opening during preparation of the base plate and/or the sensor assembly part for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate and/or the sensor assembly part coupled to the first interface. The ostomy data may comprise one or more, such as all, of first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate of the ostomy appliance based on one or more, such as all, of the first parameter data, the second parameter data and the third parameter data. The operating state may be indicative of a degree of radial erosion of the base plate, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate via the second interface; and/or in accordance with a determination that the operating state is a second operating state, transmit a second monitor signal comprising monitor data indicative of the second operating state of the base plate via the second interface.

In one or more exemplary monitor devices, the first operating state of the base plate corresponds to a situation wherein the first adhesive layer of the base plate and/or the sensor assembly part has experienced a first degree of radial erosion, e.g. the first adhesive layer is eroded to a first radial distance of the first electrode pair but not to a second radial distance of the second electrode pair.

In one or more exemplary monitor devices, the second operating state of the base plate corresponds to a situation wherein the first adhesive layer of the base plate and/or the sensor assembly part has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by
($P\_1\_1 < TH\_1\_1$),
($P\_2\_1 > TH\_1\_2$), and
($P\_3\_1 > TH\_1\_3$),
wherein $P\_1\_1$ is a first primary parameter based on the first parameter data, $TH\_1\_1$ is a first primary threshold value, $P\_2\_1$ is a second primary parameter based on the second parameter data, $TH\_1\_2$ is a first secondary threshold value, $P\_3\_1$ is a third primary parameter based on the third parameter data, and $TH\_1\_3$ is a first tertiary threshold value, and wherein the first operating state is indicative of low degree of radial erosion on the base plate and/or the sensor assembly part. The first threshold values ($TH\_1\_1$, $TH\_1\_2$ and $TH\_1\_3$) may be the same or different, e.g. depending on the electrode configuration of the base plate. The first tertiary criterion ($P\_3\_1 < TH\_1\_3$) may be omitted in the first criteria set.

The first primary parameter $P\_1\_1$ may be indicative of the resistance between the first electrode pair (first electrode and first electrode part of the ground electrode) of the base plate and/or the sensor assembly part.

The second primary parameter may be indicative of the resistance between the second electrode pair (second electrode and second electrode part of the ground electrode) of the base plate and/or the sensor assembly part.

The third primary parameter may be indicative of resistance between the third electrode pair (third electrode and third electrode part of the ground electrode) of the base plate and/or the sensor assembly part.

In one or more exemplary monitor devices, to determine an operating state of the base plate is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by
($P\_1\_1 < TH\_2\_1$),
($P\_2\_1 < TH\_2\_2$), and
($P\_3\_1 > TH\_2\_3$)
wherein $P\_1\_1$ is a first primary parameter based on the first parameter data and indicative of the resistance between the first electrode pair, $TH\_2\_1$ is a second primary threshold value, $P\_2\_1$ is a second primary parameter based on the second parameter data and indicative of the resistance between the second electrode pair, $TH\_2\_2$ is a second secondary threshold value, $P\_3\_1$ is a third primary parameter based on the third parameter data and indicative of the resistance between the third electrode pair, $TH\_2\_3$ is a second tertiary threshold value, and wherein the second operating state is indicative of medium degree of radial erosion on the base plate and/or the sensor assembly part. The second threshold values ($TH\_2\_1$, $TH\_2\_2$ and $TH\_2\_3$) may be the same or different, e.g. depending on the electrode configuration of the base plate and/or the sensor assembly part. The second primary criterion ($P\_1\_1 < TH\_2\_1$) and/or the second tertiary criterion ($P\_3\_1 > TH\_2\_3$) may be omitted in the second criteria set.

In one or more exemplary monitor devices, to determine an operating state of the base plate is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by
($P\_1\_1 > TH\_D\_1$),
($P\_2\_1 > TH\_D\_2$), and
($P\_3\_1 > TH\_D\_3$)
wherein $P\_1\_1$ is a first primary parameter based on the first parameter data and indicative of the resistance between the first electrode pair, $TH\_D\_1$ is a default primary threshold value, $P\_2\_1$ is a second primary parameter based on the second parameter data and indicative of the resistance between the second electrode pair, $TH\_D\_2$ is a default secondary threshold value, $P\_3\_1$ is a third primary parameter based on the third parameter data and indicative of the resistance between the third electrode pair, $TH\_D\_3$ is a default tertiary threshold value, and wherein the default operating state is indicative of very low or no degree of radial erosion on the base plate and/or the sensor assembly part. The default threshold values (TH_D_1, TH_D_2 and TH_D_3) may be the same or different, e.g. depending on the electrode configuration of the base plate and/or the sensor assembly part.

In one or more exemplary monitor devices, to determine an operating state of the base plate is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate corresponds to a situation wherein the first adhesive layer of the base plate and/or the sensor assembly part has experienced a third degree of radial erosion, e.g. the first adhesive layer is eroded to the third radial distance of the third electrode pair.

The third criteria set may be given by
($P\_1\_1 < TH\_3\_1$),
($P\_2\_1 < TH\_3\_2$), and
($P\_3\_1 < TH\_3\_3$)
wherein $P\_1\_1$ is a first primary parameter based on the first parameter data and indicative of the resistance between the first electrode pair, $TH\_3\_1$ is a third primary threshold value, $P\_2\_1$ is a second primary parameter based on the second parameter data and indicative of the resistance between the second electrode pair, $TH\_3\_2$ is a third secondary threshold value, $P\_3\_1$ is a third primary parameter based on the third parameter data and indicative of the resistance between the third electrode pair, $TH\_3\_3$ is a third tertiary threshold value, and wherein the third operating state is indicative of high degree of radial erosion on the base plate and/or the sensor assembly part. The third threshold values ($TH\_3\_1$, $TH\_3\_2$ and $TH\_3\_3$) may be the same or different, e.g. depending on the electrode configuration of the base plate and/or the sensor assembly part. The third primary criterion ($P\_1\_1 < TH\_3\_1$) and/or the third secondary criterion ($P\_2\_1 < TH\_3\_2$) may be omitted in the third criteria set.

In one or more exemplary monitor devices, the ostomy data comprises fourth ostomy data from a fourth electrode pair of the base plate and/or the sensor assembly part. To apply a processing scheme may comprise to obtain fourth parameter data based on the fourth ostomy data, and determine an operating state of the base plate of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate corresponds to a situation, wherein the fourth electrode pair detects fluid, such as output, between the distal surface of first adhesive layer and the skin of the user at a fourth radial distance, and thus there is a high risk of leakage from the ostomy appliance in the fourth operating state.

The fourth criteria set may be given by
($P\_4\_1 < TH\_4\_4$)
wherein $P\_4\_1$ is a fourth primary parameter based on the fourth parameter data and indicative of the resistance between the fourth electrode pair and $TH\_4\_4$ is a fourth quaternary threshold value, and wherein the fourth operating state is indicative of high risk of leakage from the ostomy appliance.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate and/or the sensor assembly part. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g. the monitor device may form an integrated part of a base plate and/or the sensor assembly part of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

A base plate for an ostomy appliance is disclosed. Also, a sensor assembly part for an ostomy appliance is disclosed, such as a sensor assembly part for being applied to a base plate. The base plate and/or the sensor assembly part comprises an electrode assembly including a plurality of electrodes. Each electrode includes a sensing part and a connection part. The connection part is configured to electrically couple the sensing part to a monitor device of the ostomy system. The base plate and/or the sensor assembly part comprises a monitor interface configured to couple the sensor assembly part to the monitor device. The base plate and/or the sensor assembly part comprises a first identifier element configured to be queried by the monitor device. For example, the first identifier element may be queried by the monitor device for the monitor device to identify the sensor assembly part and/or the base plate, for the monitor device to test the functionality of the sensor assembly part and/or the base plate, and/or for the monitor device to detect that it is fully connected to the base plate and/or the sensor assembly part.

For example, the first identifier element of the base plate and/or the sensor assembly part may comprise one or more of a resistor, a capacitive element, a magnet, a metallic actuator, a dielectric actuator, a sonic target, a photonic target, a bar code, a magnetic strip, an image ID, a variable depth ID, and a circuit element, such as an RFID tag, and an NFC tag.

Also disclosed is a monitor device of an ostomy system, such as a monitor device as disclosed above, e.g. including a base plate and/or a sensor assembly part as disclosed above. The monitor device may comprise a first interface, such as a first interface configured to couple the monitor device to a target device, such as a sensor assembly part and/or a base plate, and/or a docking station. The first interface may include a plurality of terminals configured to be connected with respective terminals of a monitor interface of the base plate or sensor assembly or docking station. The monitor device may comprise memory, and a processor coupled to the first interface and memory.

Also disclosed is a method for operating a monitor device, such as a monitor device as disclosed above, such as a monitor device configured to be connected to a base plate of an ostomy appliance, such as to a sensor assembly part of the base plate, wherein the base plate and/or the sensor assembly part has an electrode assembly; a monitor interface; and a first identifier element. The processor of the disclosed monitor device may be configured to perform the disclosed method.

The method comprises: querying the first identifier element; receiving a first identifier response from the first identifier element; and obtaining one or more parameters based on the first identifier response.

The one or more parameters may, for example, be indicative of one or more of: base plate and/or sensor assembly part type; base plate and/or sensor assembly part manufacturing batch; base plate and/or sensor assembly part manufacture date; and unique base plate and/or sensor assembly part identifier. The one or more parameters may, alternatively or additionally, be indicative of whether the monitor device is connected to a base plate and/or sensor assembly device or a docking station.

For example, the one or more parameters may be read from the first identifier element in the form of an NFC tag. Alternatively or additionally, the first identifier element may be in the form of an RFID tag and/or a bar code or a color code, measurable by the monitor device and indicative of the one or more parameters.

Alternatively or additionally, the first identifier element may comprise a resistor and/or capacitor with a known resistance and/or capacitance measurable by the monitor device and indicative of the one or more parameters. The one or more parameters may be obtained, e.g. partly, by measuring the resistance and/or capacitance of the first identifier element. For example, the first identifier element may be electrically coupled to a first set of electrodes of the plurality of electrodes, e.g. including a first electrode of the plurality of electrodes, such that the first identifier element can be queried through the first set of electrodes, e.g. through a first terminal pair of the monitor interface, corresponding to the first set of electrodes. The first set of electrodes may include the first electrode and a common electrode or ground electrode of the plurality of electrodes. Alternatively, the first set of electrodes may include the first electrode and a second electrode, or the first electrode and a third electrode.

Alternatively or additionally, the base plate and/or the sensor assembly part may comprise further identifier elements, such as a second identifier element, a third identifier element and/or a fourth identifier element. The further identifier element(s) of the base plate and/or the sensor assembly part may comprise one or more of a resistor, a capacitive element, a magnet, a metallic actuator, a dielectric actuator, a sonic target, a photonic target, a bar code, a magnetic strip, an image ID, a variable depth ID, and a circuit element, such as an RFID tag, and an NFC tag.

The method may comprise querying a further identifier element, such as the second identifier element, the third identifier element and/or the fourth identifier element. Further identifier response(s) may be received from the further identifier element(s), such as a second identifier response from the second identifier element. Obtaining the one or more parameters may include obtaining the one or more parameters based on the further identifier response(s), such as the second identifier response.

The second identifier element, the third identifier element and/or the fourth identifier element may comprise a second resistor having a second resistance, a third resistor having a third resistance, and/or a fourth resistor having a fourth resistance. The first resistance, the second resistance, the third resistance and the fourth resistance may be different from each other. Alternatively or additionally, the second identifier element, the third identifier element and/or the fourth identifier element may comprise a second capacitor having a second capacitance, a third capacitor having a third capacitance, and/or a fourth capacitor having a fourth capacitance. The first capacitance, the second capacitance, the third capacitance and the fourth capacitance may be different from each other. The one or more parameters may be obtained by the combination of measured resistances and/or capacitances. Thus, increasing the number of identifier elements may increase the number of distinguishable base plates and/or sensor assembly parts.

The second identifier element may be electrically coupled to a second set of electrodes of the plurality of electrodes, e.g. including a second electrode of the plurality of electrodes, such that the second identifier element can be queried through the second set of electrodes, e.g. through a second terminal pair of the monitor interface, corresponding to the second set of electrodes. The second set of electrodes may include the second electrode and the common electrode or ground electrode of the plurality of electrodes. Alternatively, the second set of electrodes may include the second electrode and a third electrode.

The third identifier element may be electrically coupled to a third set of electrodes of the plurality of electrodes, e.g. including a third electrode of the plurality of electrodes, such that the third identifier element can be queried through the third set of electrodes, e.g. through a third terminal pair of the monitor interface, corresponding to the third set of electrodes. The third set of electrodes may include the third electrode and the common electrode or ground electrode of the plurality of electrodes. Alternatively, the third set of electrodes may include the third electrode and a fourth electrode.

The fourth identifier element may be electrically coupled to a fourth set of electrodes of the plurality of electrodes, e.g. including a fourth electrode of the plurality of electrodes, such that the fourth identifier element can be queried through the fourth set of electrodes, e.g. through a fourth terminal pair of the monitor interface, corresponding to the fourth set of electrodes. The fourth set of electrodes may include the fourth electrode and the common electrode or ground electrode of the plurality of electrodes. Alternatively, the fourth set of electrodes may include the fourth electrode and a fifth electrode.

Querying the identifier elements may comprise measuring resistive values indicative of resistance between terminal pairs of the monitor interface corresponding to sets of electrodes. For example, querying the first identifier element may comprise measuring a first resistive value indicative of a resistance between a first terminal pair of the monitor interface, such as a first terminal pair corresponding to the first set of electrodes, and/or querying the second identifier element may comprise measuring a second resistive value indicative of a resistance between a second terminal pair of the monitor interface, such as a second terminal pair corresponding to the second set of electrodes. Identifier responses may be the resistive values. For example, the first identifier response may be the first resistive value, and/or the second identifier response may be the second resistive value. Alternatively or additionally, querying the identifier elements may comprise measuring capacitive values indicative of capacitance between terminal pairs of the monitor interface corresponding to sets of electrodes. For example, querying the first identifier element may comprise measuring a first capacitive value indicative of a capacitance between the first terminal pair of the monitor interface, and/or querying the second identifier element may comprise measuring a second capacitive value indicative of a capacitance between the second terminal pair of the monitor interface. Identifier responses may be the capacitive values. For example, the first identifier response may be the first capacitive value. Alternatively or additionally, querying the identifier elements may comprise measuring resonance frequency values indicative of a resonance frequency between terminal pairs of the monitor interface corresponding to sets of electrodes. For example, querying the first identifier element may comprise measuring a resonance frequency value indicative of a resonance frequency between the first terminal pair of the monitor interface, and/or querying the second identifier element may comprise measuring a resonance frequency value indicative of a resonance frequency between the second terminal pair of the monitor interface. Identifier responses may be the resonance frequency values. For example, the first identifier response may be the first resonance frequency value.

The identifier elements, such as the first identifier element and/or the second identifier element and/or the third identifier element and/or the fourth identifier element may be electrically connected to the connection part of the electrodes. Alternatively or additionally, and as will be described in further detail below, one or more or all of the identifier elements, such as the first identifier element and/or the second identifier element and/or the third identifier element and/or the fourth identifier element may be electrically connected to the sensing part of the electrodes.

The first resistor, the second resistor, the third resistor and/or the fourth resistor may be any suitable electrical resistance component including printed resistors, e.g. integrated as part of the electrodes and/or discrete electrical component resistors electrically coupling the electrodes.

The first resistance, the second resistance, the third resistance and/or the fourth resistance may be high resistances. For example, the electrical resistance may be selected not to interfere with monitoring of output leakage from the stoma between the adhesive layer and the skin of the patient. For example, a relatively high electrical resistance between electrodes will have little or no impact on detection of output causing a reduction in resistance between sensing parts. For example, the first resistance, the second resistance, the third resistance and/or the fourth resistance may be above 1 megaohm, such as above 10 megaohm, such as above 30 megaohm, such as above 50 megaohm, such as above 100 megaohm. For example, the first resistance, the second resistance, the third resistance and/or the fourth resistance may be at least 1 megaohm, such as between 1 and 100 megaohms, such as between 50 and 100 megaohms. The high end range of suitable resistance may be limited by the resistance between electrodes without inclusion of identifier elements.

The first capacitor, the second capacitor, the third capacitor and/or the fourth capacitor may be any suitable electrical resistance component including printed capacitors, e.g. integrated as part of the electrodes and/or discrete electrical component capacitors electrically coupling the electrodes.

The first capacitance, the second capacitance, the third capacitance and/or the fourth capacitance may be relatively small capacitance to limit power consumption and interference with the electrode configuration, but large enough to be detectable. For example, selected discrete capacitances may be at least 1 picofarad, such as between 1 picofarad and 100 nanofarads, such as between 1 picofarad and 10 nanofarads, such as between 1 picofarad and 1 nanofarad. Allowing higher potential capacitance values increase the possible number of discrete values for multi-level identification elements. However, such higher values may also increase power consumption related to capacitance measurement and increase the time constant of the sensor circuit. A high time constant may be a disadvantage because of the required delay from applying power until the circuit has settled and can be sampled, which is also a matter of power consumption because of the longer active time required for the circuit to be settled.

The one or more parameters may be directly derivable from the identifier elements, such as the first identifier element, e.g. from identifier response(s), such as the first identifier response. Alternatively or additionally, the one or more parameters may be obtained by retrieving the one or more parameters from a memory of the monitor device, e.g. based on the identifier response(s), such as the first identifier response. For example, a unique identifier may be retrieved from the first identifier element and a lookup in a table stored in the memory of the monitor device for the unique identifier may provide further information about the sensor assembly part and/or the base plate. Alternatively or additionally, the one or more parameters may be obtained by transmitting a request signal based on the identifier response(s), such as the first identifier response, to an accessory device and receiving the one or more parameters from the accessory device. For example, a unique identifier may be retrieved from the first identifier element and a lookup in a database or a table either on an accessory device or a remote server for the unique identifier may provide further information about the sensor assembly part and/or the base plate.

The method may comprise transmitting the one or more parameters. For example, the one or more parameters, such as information about the sensor assembly part and/or the base plate, such as type, batch number, manufacturing date, etc. may be transmitted, e.g. to an accessory device. Alternatively or additionally, the method may comprise storing the one or more parameters, e.g. for logging of usage, and/or for detecting systematic flaws related to specific types or batches of base plates and/or sensor assembly parts. Alternatively or additionally, the method may comprise processing the one or more parameters. For example, the one or more parameters may be used to regulate how the monitor device collects and/or processes data from the base plate and/or sensor assembly part. Alternatively or additionally, the one or more parameters may be used in processing of the parameter data of the base plate and/or sensor assembly part, e.g. in order to determine operating states of the base plate and/or sensor assembly part.

The ability to operate or control the monitor device based on base plate and/or sensor assembly part identification can enhance the functionality, use and/or efficacy of the device. For example, the monitor device can be used with a wide range of ostomy appliances having different characteristics and features, and through use of the base plate and/or sensor assembly part identification information the monitor device can be adapted for the particular ostomy appliance and/or base plate and/or sensor assembly part with which it is used.

The one or more parameters may be indicative of a data collection scheme. The method may include determining a data collection scheme based on the one or more parameters, such as the base plate and/or sensor assembly part identification information. The method may comprise collecting ostomy data representative of a condition, such as an operating state, of the ostomy appliance, e.g. from the base plate and/or the sensor assembly part, based on the data collection scheme, and transmitting, storing and/or processing the collected ostomy data. By this method, the monitor device can be adapted to collect data based on the ostomy appliance and/or base plate and/or sensor assembly part with which it is used. For example, a sampling rate may be adjusted based on knowledge, e.g. empirical knowledge, of how fast operating states may change for certain base plate and/or sensor assembly types. Alternatively or additionally, the data collection scheme may be indicative of which terminals on the monitor device from which to collect the ostomy data. Thus, the method may comprise determining which terminals on the monitor device to collect the ostomy data from, e.g. based on the one or more parameters, such as the data collection scheme, and/or the method may comprise determining timing of the ostomy data collection, e.g. based on the one or more parameters, such as the data collection scheme.

Determining the data collection scheme, such as obtaining the one or more parameters being indicative of the data collection scheme, may include receiving the one or more parameters, such as the data collection scheme, from an accessory device. For example, a request signal based on identifier response(s), such as the first identifier response, may be transmitted to the accessory device and the one or more parameters being indicative of the data collection scheme may be received from the accessory device. Determining the data collection scheme, such as obtaining the one or more parameters being indicative of the data collection scheme, may include retrieving the one or more parameters, such as the data collection scheme, from a memory of the monitor device.

The one or more parameters may be indicative of a data processing scheme. The method may include determining a processing scheme based on the one or more parameters, such as the base plate and/or sensor assembly part identification information. The method may comprise collecting ostomy data representative of a condition, such as an operating state, of the ostomy appliance, processing the collected ostomy data based on the processing scheme to obtain processed ostomy data, e.g. to determine an operating state of the ostomy appliance. The method may further comprise storing and/or transmitting the operating state. Processing the ostomy data based on the processing scheme may include determining an operating state indicative of one or more of (1) adhesive performance of the ostomy appliance, (2) moisture level of an adhesive layer of the ostomy appliance, (3) electrical properties of the adhesive layer of the ostomy appliance, (4) moisture patterns of the base plate and/or sensor assembly part, (5) leakage state of the ostomy appliance, (6) leakage location, or (7) leakage risk of the ostomy appliance. By this method, the monitor device can be adapted to use processing schemes based on the ostomy appliance and/or base plate and/or sensor assembly part with which it is used.

Determining the processing scheme, such as obtaining the one or more parameters being indicative of the processing scheme, can include receiving the one or more parameters, such as the processing scheme, from an accessory device. For example, a request signal based on identifier response(s), such as the first identifier response, may be transmitted to the accessory device and the one or more parameters being indicative of the processing scheme may be received from the accessory device. Determining the processing scheme, such as obtaining the one or more parameters being indicative of the processing scheme, may include retrieving the one or more parameters, such as the processing scheme, from a memory of the monitor device. The processing scheme, such as the one or more parameters, may be indicative of one or more base plate operating state parameters and/or one or more rules for processing the ostomy data. The method may include determining one or more base plate operating state parameters and/or one or more rules for processing the ostomy data, e.g. based on the one or more parameters.

The one or more parameters may be indicative of an operating state of the monitor device and/or the base plate and/or the sensor assembly part. The method may comprise determining if one or more operability criteria are satisfied based on the one or more parameters; and providing a first monitor device signal indicative of operating failure of the monitor device and/or the base plate and/or the sensor assembly part if the one or more operability criteria are not being satisfied. For example, the operability or functionality of the monitor device and/or the base plate and/or the sensor assembly part may be reported to users. Malfunctions and/or normal operation of the monitor device and/or the base plate and/or the sensor assembly part can be reported to users and other accessory devices, thereby providing warnings of possible problems. The system may be extended to also detect malfunctions or normal operation of other parts of an ostomy system, such as an accessory device and/or an ostomy pouch.

The one or more parameters may be indicative of a power capacity of the monitor device. Obtaining the one or more parameters may include obtaining a power parameter value indicative of a power capacity, such as a power reserve, of a power unit of the monitor device. Determining if the one or more operability criteria are satisfied may be based on the power parameter. For example, in order to satisfy the one or more operability criteria, it may be required that the power unit of the monitor device has a sufficient power capacity to be operational for a predetermined amount of time. Alternatively or additionally, the method may comprise determining if one or more secondary operability criteria are satisfied, e.g. based on the power parameter. The method may comprise providing another monitor device signal indicative of operating failure of the monitor device if the one or more secondary operability criteria are not being satisfied.

The method may comprise checking an electrical signal of the power unit of the monitor device to assess the power capacity of the power unit. For example, the power capacity of the power unit may be queried, e.g. by the processor, at one or more times, e.g. periodically while the monitor device is coupled to the base plate and/or when the monitor device is decoupled from the base plate. Thereby the operability of the monitor device may be assessed. For the foregoing exemplary queries of the power capacity of the power unit, it may be determined if one or more operability criteria are satisfied by comparing measured values to known values stored in memory.

In embodiments, the processor of the monitor device is configured to determine an operating failure type from a set of operating failure types stored in the memory. More particularly, in embodiments the processor is configured to assess the nature of an operability failure, such as an inoperable electrode and/or a low power capacity, and thereafter provide a first monitor device signal that is indicative of the operating failure type. By way of example, the monitor device can provide a warning for an inoperable electrode that is distinct from a warning for a low power capacity. Accordingly, the processor checks for operability issues and compares readings to known parameter criteria stored in the memory, and as necessary, references alert conditions and warnings that are also stored in memory, and then notifies the user as may be appropriate.

The identifier elements, such as the first identifier element, may include resistive elements having resistances, such as a first resistive element having a first resistance. The identifier elements may be connected to sensing parts of the electrodes. For example, the first identifier element may be electrically connected to a sensing part of the first electrode and/or electrically connected to a sensing part of the first set of electrodes. The sensing part of the electrodes may extend from the connection part of the respective electrode to a sensing part end of the respective electrode. For example, the sensing part of the first electrode may extend from the connection part of the first electrode to the sensing part end of the first electrode. An identifier element may be electrically connected near the sensing part end of the sensing part of the respective electrode. For example, the first identifier element may be electrically connected near the sensing part end of the sensing part of the first electrode. Thereby, the identifier elements, such as the first identifier element, may be queried by measuring resistance. By measuring a resistive value between sets of electrodes, such as between the first set of electrodes operability or malfunction of sets of electrodes may be revealed. Further identifier elements, such as the second identifier element, the third identifier element, and/or the fourth identifier element, may be provided, e.g. as further resistive elements, between further sets of electrodes, allowing measuring and detection of operability or malfunction of further sets, such as all sets, of the plurality of electrodes. Thereby, a determination of the operability of one or more electrodes of the base plate and/or sensor assembly part may be assessed. Determination of operability of one or more electrodes may further be used in determination of a processing scheme and/or a data collection scheme as described above. Determination of operability of one or more electrodes may comprise comparing a known set of values, such as resistive values, to measured values, such as measured resistances.

The method may comprise obtaining ostomy data from the base plate via the first interface during a time period that the base plate is applied to a skin surface of the user, e.g. to determine a base plate application parameter indicative of application quality based on the ostomy data. Determining if the one or more operability criteria are satisfied may, alternatively or additionally, be based on the base plate application parameter. Hence, the user may be warned if the base plate application parameter indicates that the application quality is decreasing, e.g. below a set threshold.

The method may comprise determining an operating failure type from a set of operating failure types. Providing the first monitor device signal may include providing the first monitor device signal indicative of the operating failure type. Thereby, the user may be assisted in solving an error causing the failure and/or the user may be provided with information of the status of operability. The first monitor device signal may indicate that a component of the ostomy appliance, e.g. the base plate, the sensor assembly part, an ostomy pouch, etc., is one or more of inoperative, damaged, defective, improperly connected or improperly attached. Alternatively or additionally, the method may further comprise in accordance with the operability criteria being satisfied, providing a second monitor device signal indicative of correct operation of the base plate and/or the sensor assembly part. For example, if the operability evaluation does not result in a finding of an operability problem, a notification may be provided, such as to the user, that the monitor device and/or base plate and/or sensor assembly part are functioning correctly. The processor may check the memory for notification types for the second monitor device signal, which can be one or more of an audible signal through a loudspeaker of the monitor device, a tactile signal through a haptic feedback element, or a wireless signal to an accessory device, such as a phone or a wearable item, e.g. a watch, wrist band or ring, that then may alert the user.

The first monitor device signal and/or the second monitor device signal may be one or more of an audible signal, a tactile signal, or a wireless signal to an accessory device.

The method may comprise obtaining a connection parameter indicative of mechanical connection quality between the monitor device and the base plate and/or sensor assembly part. Determining if the one or more operability criteria are satisfied may, alternatively or additionally, be based on the connection parameter. Thus, a poorly connected monitor device, having an increased risk of experiencing a failed connection, may be indicated by the first monitor device signal.

The one or more parameters may be indicative of connection, such as coupling, between the monitor device and the base plate and/or sensor assembly part. For example, the one or more parameters may be indicative of the monitor device being fully connected and/or coupled to the base plate and/or sensor assembly part.

The monitor device may comprise an identifier sensor configured to detect and/or query the identifier element(s) of the base plate and/or sensor assembly part, such as the first identifier element, the second identifier element, the third identifier element and/or the fourth identifier element.

The monitor device may be configured to detect coupling, such as correct and/or complete coupling, between the monitor device and a target device, such as the base plate and/or the sensor assembly part and/or a docking station. The identifier sensor may be a coupling sensor, such as a coupling sensor configured to detect and/or identify a identifier element of the target device and/or configured to detect complete coupling of the monitor device to the target device.

The detection and/or identification of the target device, e.g. by the identifier element(s) of the target device, may be utilized as data for data processing, a trigger for data collection, a trigger for activating a power-saving mode, and/or a trigger for indicating (e.g. with an alarm such as haptic or sound) a successfully coupling between the target device and the monitor device.

The processor and/or the identifier sensor may be configured to generate a coupled signal indicative of the monitor device being coupled, such as correctly and/or completely coupled, to the target device. Alternatively or additionally, the processor and/or the identifier sensor may be configured to generate an identifier signal. The identifier signal may be indicative of the target device, such as which target device is coupled to the monitor device and/or whether the target device is coupled, such as correctly and/or completely coupled, to the monitor device. The processor may be configured to receive the coupled signal and/or the identifier signal from the identifier sensor. The processor may be configured to determine whether the monitor device is coupled, such as completely and/or correctly coupled, to the target device, e.g. based on the identifier signal.

The identifier sensor may comprise a resistive sensor. The resistive sensor may be configured to measure a resistance of a target resistor, such as a target resistor of the target device, e.g. of the identifier element(s) of the target device, such as the first identifier element, the second identifier element, the third identifier element and/or the fourth identifier element.

The resistive sensor may comprise a first resistive sensor terminal and a second resistive sensor terminal.

The resistive sensor may be configured to generate the coupled signal, e.g. when the resistance measured substantially matches a target resistance and/or when the resistance measured is larger than a threshold resistance, and/or when the resistance measured by the resistive sensor substantially matches one of a plurality of reference resistances.

The resistive sensor may be configured, such as further configured, to generate the identifier signal, e.g. when the resistance measured by the resistive sensor substantially matches one of a plurality of reference resistances.

The resistive sensor may be configured, such as further configured, to generate the identifier signal. For example, the identifier signal may be indicative of the resistance measured by the resistive sensor.

The identifier sensor may comprise a Hall sensor. The Hall sensor may be configured to measure a magnetic flux density of a target magnet of the target device, e.g. of the identifier element(s) of the target device, such as the first identifier element, the second identifier element, the third identifier element and/or the fourth identifier element.

The Hall sensor may be configured, such as further configured, to generate the coupled signal, e.g. when the magnetic flux density measured substantially matches a target magnetic flux density and/or when the magnetic flux density measured is larger than a threshold magnetic flux density, and/or when the magnetic flux density measured by the Hall sensor substantially matches one of a plurality of reference magnetic flux densities.

The Hall sensor may be configured, such as further configured, to generate the identifier signal, e.g. when the magnetic flux density measured by the Hall sensor substantially matches one of a plurality of reference magnetic flux densities.

The Hall sensor may be configured, such as further configured, to generate the identifier signal. For example, the identifier signal may be indicative of the magnetic flux density measured by the Hall sensor.

The identifier sensor may comprise a reed switch. The reed switch may be configured to be triggered by a turning magnet of the target device, e.g. of the identifier element(s) of the target device, such as the first identifier element, the second identifier element, the third identifier element and/or the fourth identifier element.

The reed switch may be configured, such as further configured, to generate the coupled signal, e.g. when the reed switch is triggered.

The reed switch may be configured, such as further configured, to generate the identifier signal. For example, the identifier signal may be indicative of triggering of the reed switch.

The reed switch may be configured to switch from an open circuit to a closed circuit, e.g. when the reed switch is triggered.

The identifier sensor may comprise an inductive sensor. The identifier sensor may be configured to engage a metallic actuator of the target device, e.g. of the identifier element(s) of the target device, such as the first identifier element, the second identifier element, the third identifier element and/or the fourth identifier element. The metallic actuator may be ferrous (steel), or the metallic actuator may be nonferrous (e.g. aluminium, copper, stainless steel, brass).

The inductive sensor may be configured, such as further configured, to generate the coupled signal, e.g. when the inductive sensor engages the metallic actuator. The metallic actuator may be configured to affect the inductance measured by the inductive sensor.

The inductive sensor may detect the metallic actuator by detecting a change in oscillation amplitude and/or resonance frequency in the inductive sensor resulted from the metallic actuator being sufficiently near the inductive sensor. For example, the inductive sensor may detect engagement with the metallic actuator by detecting the change in oscillation amplitude and/or resonance frequency in the inductive sensor resulted from the metallic actuator being sufficiently near the inductive sensor.

The inductive sensor may generate the coupled signal, e.g. when the change in oscillation amplitude and/or resonance frequency substantially matches a target change in oscillation amplitude and/or resonance frequency, respectively. The target change in oscillation amplitude and/or resonance frequency may correspond to the change in oscillation amplitude and/or resonance frequency measurable by the inductive sensor when the monitor device and the target device are coupled, respectively.

The inductive sensor may be configured, such as further configured, to generate the identifier signal. For example, the identifier signal may be indicative of the oscillation amplitude and/or resonance frequency measured by the inductive sensor.

The inductive sensor may be configured, such as further configured, to detect a plurality of metallic actuators, e.g., each having one of a plurality of ferrite contents. The inductive response in oscillation amplitude and/or resonance frequency of the inductive sensor may differ between more ferrous and less ferrous materials. The inductive sensor may be configured, such as further configured to generate the identifier signal, to be received by the processor of the monitor device, e.g. based on the different inductive response correlating to which of the metallic actuator has engaged the inductive sensor.

Each of the plurality of metallic actuators may correspond to one of various target devices (e.g. one or more base plates, sensor assembly parts, or docking stations). For example, one of the plurality of base plates and/or sensor assembly parts may comprise a first metallic actuator, and a docking station may comprise a second metallic actuator. The correspondence between the plurality of metallic actuators and the various target devices may provide the inductive sensor and/or the processor to identify which target device is coupled to the monitor device.

The identifier sensor may comprise a capacitive sensor. The capacitive sensor may be configured to engage a dielectric actuator of the target device, e.g. of the identifier element(s) of the target device, such as the first identifier element, the second identifier element, the third identifier element and/or the fourth identifier element. The dielectric actuator may comprise material having dielectric constant greater than that of the material of the coupling parts of the monitor device and of the base plate. For example, the dielectric actuator may comprise alumina and/or titanates. The dielectric actuator may be configured to affect the oscillation amplitude and/or resonance frequency measured by the inductive sensor.

The capacitive sensor may be configured, such as further configured, to generate the coupled signal, e.g. when the capacitive sensor engages the dielectric actuator.

The capacitive sensor may detect the dielectric actuator by detecting a change in oscillation amplitude and/or resonance frequency of the inductive sensor resulted from the dielectric actuator being sufficiently near the capacitive sensor. For example, the capacitive sensor may detect engagement with the dielectric actuator by detecting the change in oscillation amplitude and/or resonance frequency of the inductive sensor resulted from the dielectric actuator being sufficiently near the capacitive sensor.

The capacitive sensor may generate the coupled signal, e.g. when the change in oscillation amplitude and/or resonance frequency substantially matches a target change in oscillation amplitude and/or resonance frequency, respectively. The target change in oscillation amplitude and/or resonance frequency may correspond to the change in oscillation amplitude and/or resonance frequency measurable by the capacitive sensor when the monitor device and the target device are coupled, respectively.

The capacitive sensor may be configured, such as further configured, to generate the identifier signal. For example, the identifier signal may be indicative of the oscillation amplitude and/or resonance frequency measured by the capacitive sensor.

The capacitive sensor may be configured, such as further configured, to detect a plurality of dielectric actuators, e.g., each having one of a plurality of dielectric constants. The capacitive response in oscillation amplitude and/or resonance frequency of the capacitive sensor may differ between materials with higher and lower dielectric constants. The capacitive sensor may be configured, such as further configured to generate the coupled signal and/or the identifier signal, to be received by the processor of the monitor device based on the different capacitive response correlating to which of the dielectric actuator has engaged the capacitive sensor.

Each of the plurality of dielectric actuators may correspond to one of various target devices (e.g. one or more base plates, sensor assembly parts or docking stations). For example, one of the plurality of base plates and/or sensor assembly parts may comprise a first dielectric actuator, and a docking station may comprise a second dielectric actuator. The correspondence between the plurality of dielectric actuators and the various target devices may provide the capacitive sensor and/or the processor to identify which target device is coupled to the monitor device.

The identifier sensor may comprise an ultrasonic sensor, e.g. including an emitter and/or a receiver. The ultrasonic sensor may be configured to detect a sonic target of the target device, e.g. of the identifier element(s) of the target device, such as the first identifier element, the second identifier element, the third identifier element and/or the fourth identifier element. The sonic target may be sound-reflective and/or sound-absorbent.

The ultrasonic sensor may be configured, such as further configured, to generate the coupled signal, e.g. when the sonic target is detected.

The ultrasonic sensor may be a diffuse ultrasonic sensor, a retro-reflective ultrasonic sensor, and/or a through-beam ultrasonic sensor.

The ultrasonic sensor may be configured, such as further configured, to generate the identifier signal. For example, the identifier signal may be indicative of a measured reflectance of a transmitted ultrasonic beam measured by the ultrasonic sensor.

The identifier sensor may comprise a photoelectric sensor, e.g. including an emitter and/or a receiver. The photoelectric sensor may be configured to detect a photonic target of the target device, e.g. of the identifier element(s) of the target device, such as the first identifier element, the second identifier element, the third identifier element and/or the fourth identifier element. The photonic target may be light-reflective and/or light-absorbent.

The photoelectric sensor may be configured, such as further configured, to generate the coupled signal, e.g. when the photonic target is detected.

The photoelectric sensor may be a diffuse photoelectric sensor, a retro-reflective photoelectric sensor, and/or a through-beam photoelectric sensor.

The photoelectric sensor may be configured, such as further configured, to generate the identifier signal. For example, the identifier signal may be indicative of a measured reflectance of transmitted light measured by the photoelectric sensor.

The identifier sensor may comprise a bar code reader, e.g. configured to identify a reference bar code of the target device, e.g. of the identifier element(s) of the target device, such as the first identifier element, the second identifier element, the third identifier element and/or the fourth identifier element.

The bar code reader may be configured, such as further configured, to generate the identifier signal, e.g. to be received by the processor, such as the processor of the monitor device, when the reference bar code is identified. The identifier signal may be indicative of the bar code read by the bar code reader.

The identifier sensor may comprise a magnetic strip reader, e.g. configured to identify a reference magnetic strip of the target device, e.g. of the identifier element(s) of the target device, such as the first identifier element, the second identifier element, the third identifier element and/or the fourth identifier element.

The magnetic strip reader may be configured, such as further configured, to generate the identifier signal, e.g. to be received by the processor, such as the processor of the monitor device, when the reference magnetic strip is identified. For example, the identifier signal may be indicative of the magnetic strip, such as a configuration of the magnetic strip, read by the magnetic strip reader.

The identifier sensor may comprise an image ID reader, e.g. configured to identify a reference image ID of the target device, e.g. of the identifier element(s) of the target device, such as the first identifier element, the second identifier element, the third identifier element and/or the fourth identifier element.

The image ID reader may be configured, such as further configured, to generate the identifier signal, e.g. to be received by the processor of the monitor device, when the reference image ID is identified. For example, the identifier signal may be indicative of the image ID read by the image ID reader.

The identifier sensor may comprise a variable depth ID reader, e.g. configured to identify a reference variable depth ID of the target device, e.g. of the identifier element(s) of the target device, such as the first identifier element, the second identifier element, the third identifier element and/or the fourth identifier element. In embodiments, the reference variable depth ID of the target device may comprise one or more regions with a first depth or height and one or more regions with a second depth or height.

The variable depth ID reader may be configured, such as further configured, to generate the identifier signal, e.g. to be received by the processor, such as the processor of the monitor device, when the reference variable depth ID is identified. For example, the identifier signal may be indicative of the variable depth ID read by the variable depth ID reader.

The identifier sensor may comprise an RFID reader, e.g. configured to identify a reference RFID of the target device, e.g. of the identifier element(s) of the target device, such as the first identifier element, the second identifier element, the third identifier element and/or the fourth identifier element.

The RFID reader may be configured, such as further configured to generate the identifier signal, e.g. to be received by the processor, such as the processor of the monitor device, when the reference RFID is identified. For example, the identifier signal may be indicative of the RFID tag read by the RFID tag reader.

The identifier sensor may comprise an NFC tag reader, e.g. configured to identify and/or read a reference NFC tag of the target device, e.g. of the identifier element(s) of the target device, such as the first identifier element, the second identifier element, the third identifier element and/or the fourth identifier element.

The NFC tag reader may be configured, such as further configured, to generate the identifier signal, e.g. to be received by the processor, such as the processor of the monitor device, when the reference NFC tag is identified. For example, the identifier signal may be indicative of the NFC tag read by the NFC tag reader.

The identifier sensor may comprise an optical sensor, e.g. configured to identify a reference optical element of the target device, e.g. of the identifier element(s) of the target device, such as the first identifier element, the second identifier element, the third identifier element and/or the fourth identifier element. The reference optical element may comprise a colour code, a QR code, a bar code, or similar.

The optical sensor may be configured, such as further configured to generate the identifier signal, e.g. to be received by the processor, such as the processor of the monitor device, when the reference optical element is identified. For example, the identifier signal may be indicative of the optical element identified by the optical sensor.

The identifier sensor may comprise a magnetic coil, e.g. configured to detect an inductor of the target device, e.g. of the identifier element(s) of the target device, such as the first identifier element, the second identifier element, the third identifier element and/or the fourth identifier element.

The magnetic coil sensor may be configured to generate the identifier signal. For example, the identifier signal may be indicative of the inductor detected by the magnetic coil sensor.

The identifier sensor may comprise a QR-code reader and/or a colour code reader, e.g. configured to identify a reference QR-code and/or colour code of the target device, e.g. of the identifier element(s) of the target device, such as the first identifier element, the second identifier element, the third identifier element and/or the fourth identifier element.

The QR-code reader and/or a colour code reader may be configured, such as further configured, to generate the identifier signal, e.g. to be received by the processor, such as the processor of the monitor device, when the reference QR-code and/or a colour code is identified.

The QR-code reader and/or a colour code reader may be configured, such as further configured, to generate the identifier signal. For example, the identifier signal may be indicative of the reference QR-code reader and/or a colour code reader identified by the QR-code reader and/or a colour code reader.

The disclosed base plate, sensor assembly part, monitor device and associated method provides several advantages, among others the operability or functionality of the monitor device and accessory devices or appliances coupled to the base plate can be assessed and detected, and those operational characteristics can be reported to users. For example, a determination of the operability of one or more electrodes can be assessed. The assembly/coupling of the monitor device to an ostomy appliance such as a base plate can be assessed. The monitor device can assess whether the base plate has been properly applied to the user's skin surface. Mechanical connections between the monitor device and base plate can be assessed. Battery capacity or other power characteristics of the monitor device can be assessed. Malfunctions and/or normal operation of the ostomy appliance and monitor device can be reported to users and other accessory devices, thereby providing warnings of possible problems.

Furthermore, more effective operation of a monitor device may be achieved by regulating data collection and/or processing schemes more effectively. For example, detection and/or identification may facilitate more accurately interpretation of data collected by the ostomy system. For example, electrode design, electrode coverage in the base plate and/or adhesive properties may differ for different base plates. Thus, allowing the monitor device to retrieve information regarding the attached device, may facilitate a better, e.g. more accurate, data analysis, e.g. regarding the status or health of the base plate.

For example, a target device may be one of a plurality of base plates and/or sensor assembly parts, wherein each of the plurality of base plates and/or sensor assembly parts may have different configurations configured for different types of sensing. For example, electrode design, electrode coverage in the base plate and/or adhesive properties may differ for different target devices. Thus, allowing the monitor device to retrieve information regarding the attached target device, may facilitate a better, e.g. more accurate, data analysis, e.g. regarding the status or health of the base plate.

FIG. 1 illustrates an exemplary ostomy system. The ostomy system 1 comprises an ostomy appliance 2 including a base plate 4 and an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate has a stoma-receiving opening 18 with a stoma center point. The size and/or shape of the stomal opening 18 is typically adjusted by the user or nurse before application of the ostomy appliance to accommodate the user's stoma.

The ostomy system 1 optionally comprises a docking station 20 forming an accessory device of the ostomy system 1. The docking station comprises 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
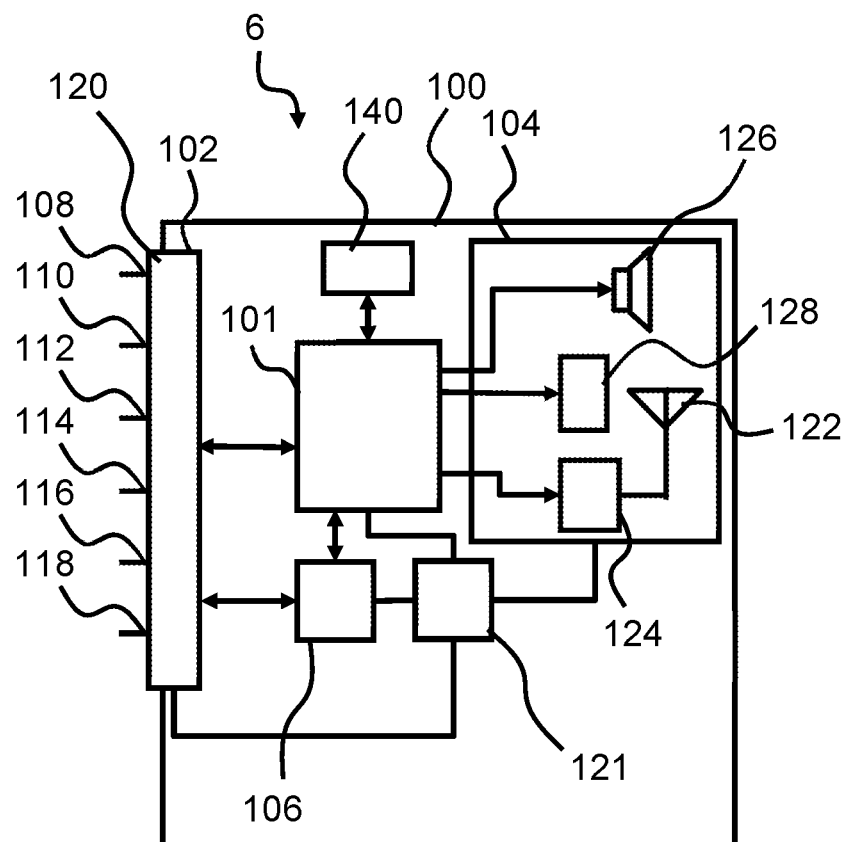
FIG. 2 illustrates an exemplary monitor device of the ostomy system.

FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a sensor unit 140 connected to the processor 101. The sensor unit 140 comprises a temperature sensor for feeding temperature data to the processor and a G-sensor or accelerometer for feeding acceleration data to the processor 101. Additionally or alternatively, the sensor unit 140 may comprise a humidity sensor and/or an acoustic sensor. The sensor unit 140 may comprise alternative and/or additional sensors suitable and/or relevant to an ostomy system as described.

The processor 101 is configured to apply a processing scheme, and the first interface 102 is configured for collecting ostomy data from the base plate coupled to the first interface, the ostomy data comprising first ostomy data from a first electrode pair of the base plate, second ostomy data from a second electrode pair of the base plate, and third ostomy data from a third electrode pair of the base plate. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate of the ostomy appliance based on one or more, e.g. all, of the first parameter data, the second parameter data and the third parameter data, wherein the operating state is indicative of a degree of radial erosion of the base plate and/or acute leakage risk for the ostomy appliance. The monitor device 6 is configured to, in accordance with a determination that the operating state is a first operating state, transmit a first monitor signal comprising monitor data indicative of the first operating state of the base plate via the second interface; and in accordance with a determination that the operating state is a second operating state, transmit a second monitor signal comprising monitor data indicative of the second operating state of the base plate via the second interface.

The processor 101 may receive identification information, such as base plate identification information through the first interface 102 via terminals 108, 110, 112, 114, 116, 118. For example, the identification information may be represented by identifier elements of an electrode configuration. The processor 101 may receive the identification information in the form of one or more resistance values, one or more capacitance values, one or more multiple bit digital values or by other techniques. The identification information may be representative of one or more of base plate and/or sensor assembly part type, manufacturing batch, manufacture date, and/or a unique identifier.

In some implementations, following receipt of the identification information, processor 101 may transmit the identification information by second interface 104, such as by the wireless transceiver 124 to the accessory device 8 and/or docking station 20, and/or the processor 101 may store the identification information in the memory 106, and/or the processor 101 may process the identification information.

The processor 101 may determine a data collection scheme based on the identification information, and/or the processor 101 may determine the data collection scheme by accessing the data collection scheme from memory 106 and/or by receiving the data collection scheme through the wireless transceiver 124. In some examples, the processor 101 may receive the data collection scheme from accessory device 8 and/or docking station 20. In the same or different implementations, the processor 101 may receive the data collection scheme from a remote server, e.g., via accessory device 8 and/or docking station 20. In implementations where the processor 101 receives the data collection scheme through the wireless transceiver 124, processor 101 may store the received data collection scheme in the memory 106 for subsequent access. The processor 101 may retrieve the data collection scheme from the memory 106 for preforming data collection according to the data collection scheme.

For example, in some implementations, the processor 101 determines the data collection scheme by determining which of terminals 108, 110, 112, 114, 116, 118 on the monitor device 6 to collect the ostomy data from. In the same or different implementations, the processor 101 determines the timing of the ostomy data collection. In various implementations, the processor 101 controls the collection of the ostomy data based on either or both of the determined terminals on the monitor device 106, and the determined timing.

In some implementations, the data collection scheme may include conductor integrity testing. Such implementations may be suitable for base plates and/or sensor assembly parts with resistive identifier elements or capacitive identifier elements located at the distal ends of conductive elements, such as a farthest end of the conductive elements, of the electrode configuration of the base plate and/or sensor assembly part. For example, resonance frequency may be measured between pairs terminals 108, 110, 112, 114, 116, 118, such as to determine their respective operability.

In the same or different implementations, the processor 101 may determine a processing scheme based on the base plate and/or sensor assembly part identification information. In some implementations the processor 101 determines the processing scheme by receiving the processing scheme through the transceiver 124 of second interface 104, e.g., from an accessory device and/or docking station. In such implementations, the processor 101 may store the processing scheme in the memory 106 for later retrieval.

The processor may 101 receive ostomy data representative of a condition of the ostomy appliance from the base plate and/or a sensor assembly part. The processor 101 may store the operating state and/or monitor data based on the ostomy data in memory 106 and/or transmit the operating state via second interface 104, e.g. with transceiver 124 of second interface 104, to an accessory device and/or a docking station.

Figure 3:
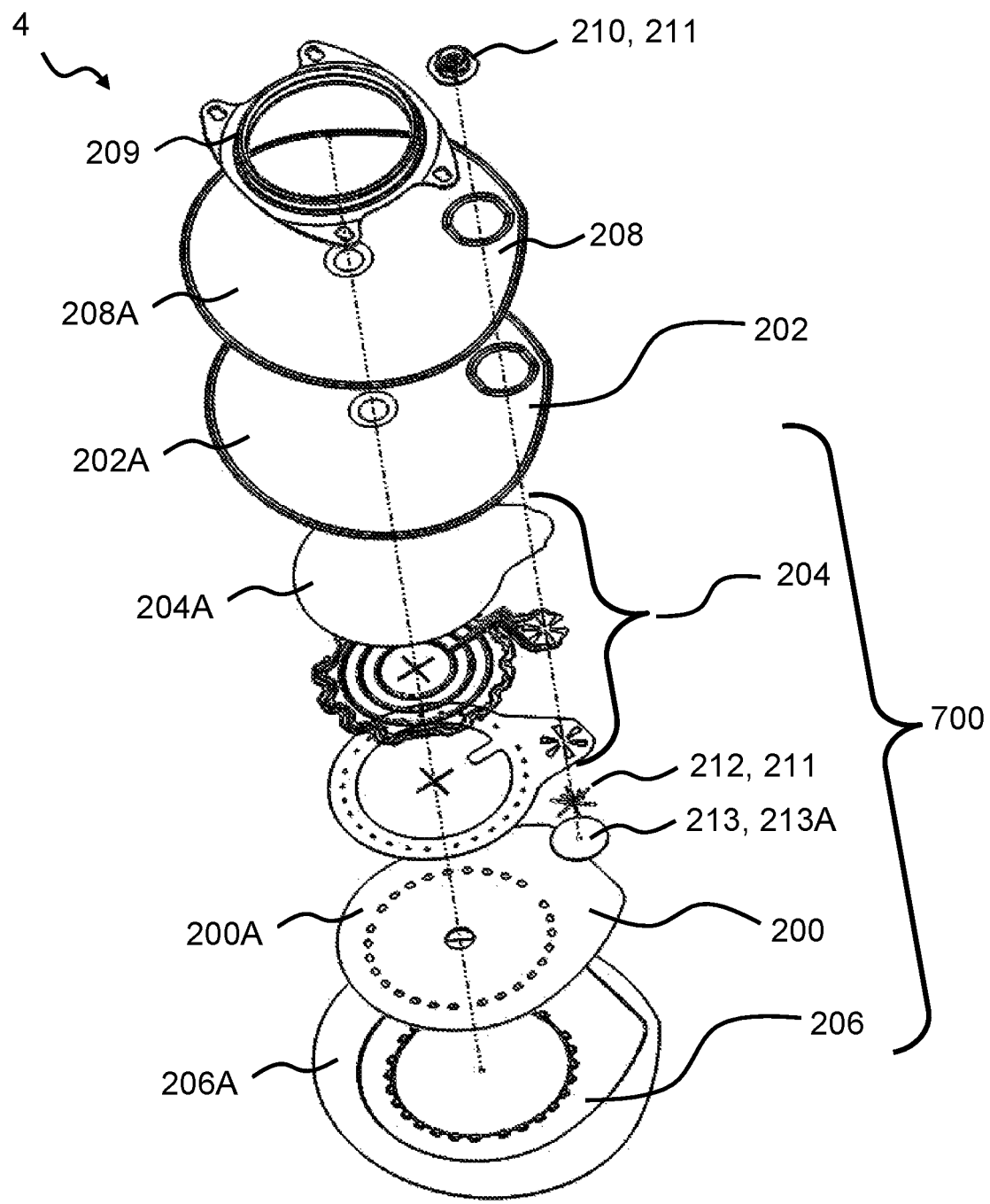
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the distal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
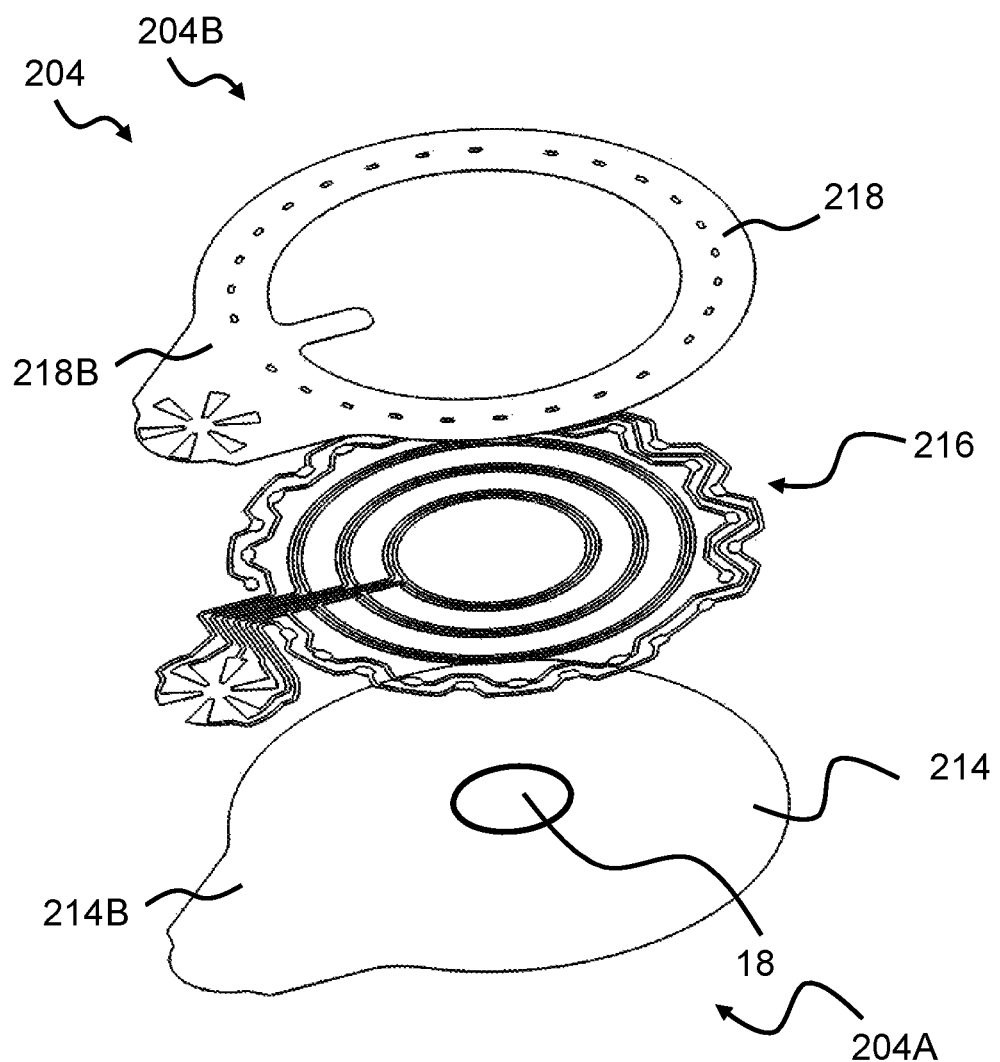
FIG. 4 is an exploded view of an exemplary electrode assembly.

FIG. 4 illustrates an exploded view of an exemplary electrode assembly 204 of a base plate and/or a sensor assembly part. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part for connecting the electrodes to respective terminal elements of the monitor interface. Further, electrode assembly 204 comprises a masking element 218 with proximal surface 218B and configured to insulate electrode parts of electrodes 216 from the first adhesive layer of the base plate and/or of the sensor assembly part. The masking element 218 covers or overlap with parts of the electrodes 216 when seen in the axial direction.

Figure 5:
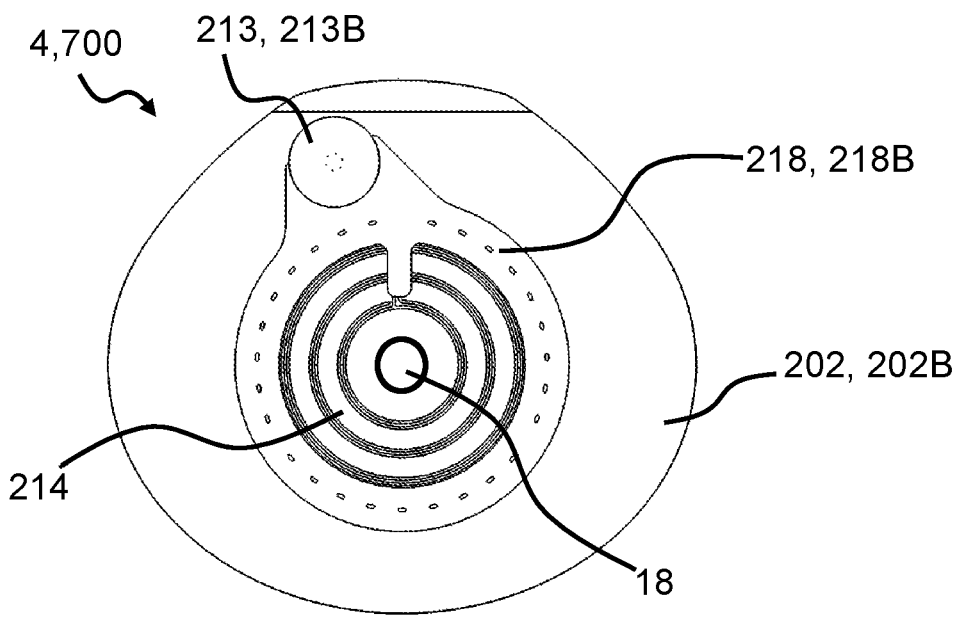
FIG. 5 is a proximal view of parts of a base plate and/or sensor assembly part.

FIG. 5 is a proximal view of proximal surfaces of base plate parts of the base plate and/or the sensor assembly part without the first adhesive layer and the release liner. The base plate 4 and/or the sensor assembly part 700 comprises a first intermediate element 213 on the distal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate and/or the sensor assembly part.

Figure 6:
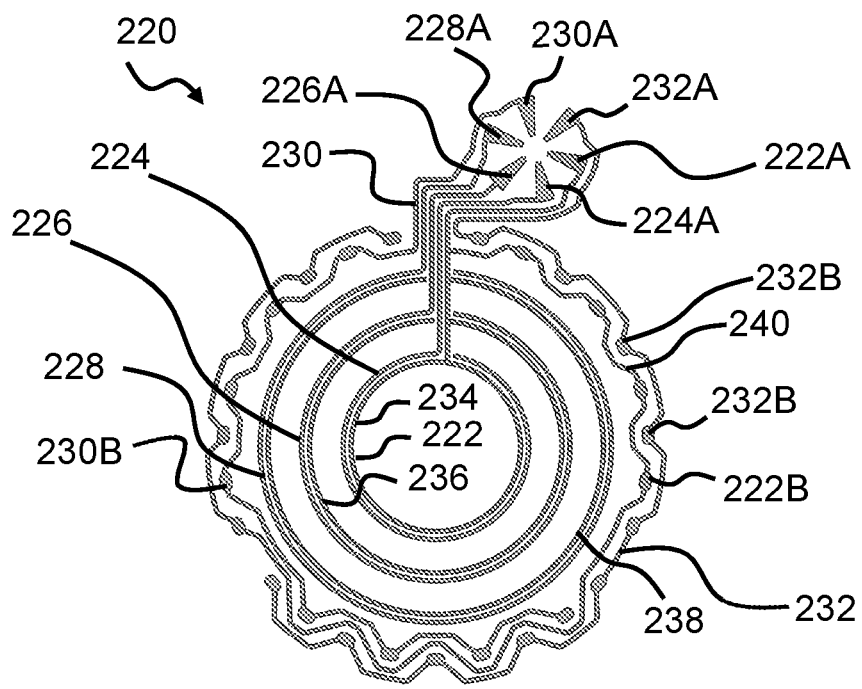
FIG. 6 is a distal view of an exemplary electrode configuration.

FIG. 6 is a distal view of an exemplary electrode configuration 220 of electrodes 216 of the electrode assembly 204. The electrode configuration 220/electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

Figure 7:
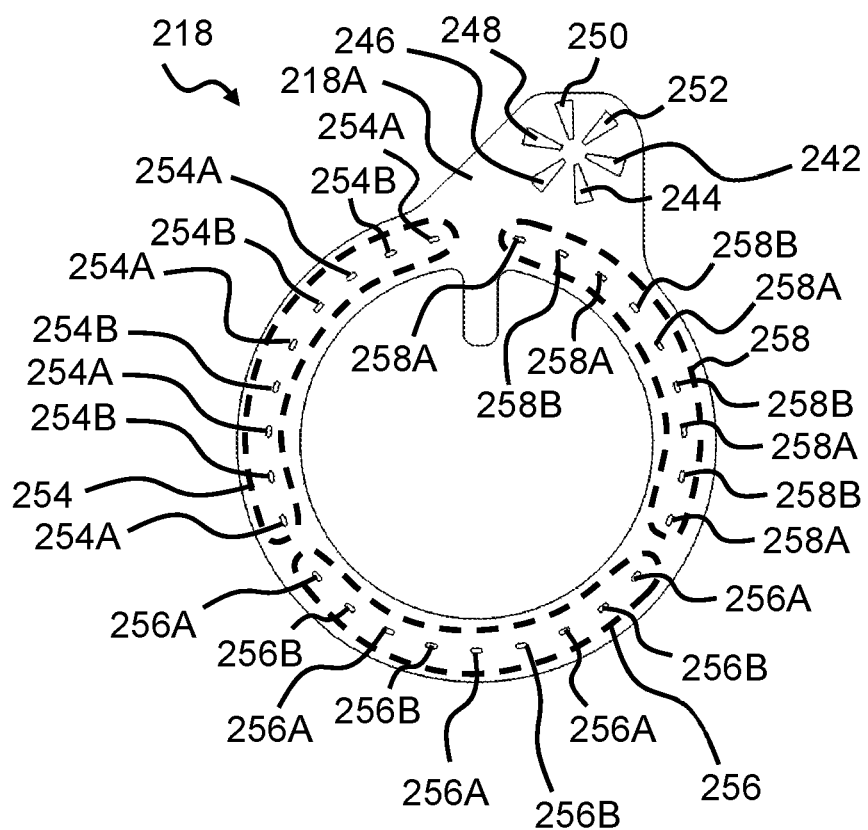
FIG. 7 is a distal view of an exemplary masking element.

The ground electrode 222 comprises a first electrode part 224 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
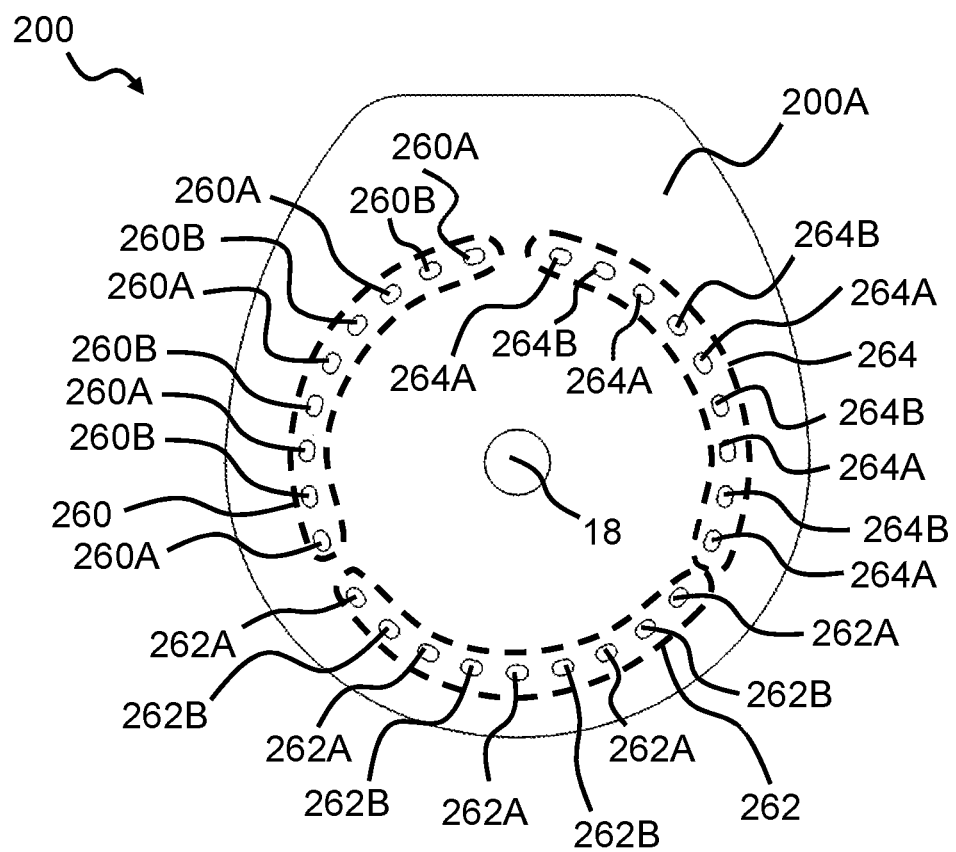
FIG. 8 is a distal view of an exemplary first adhesive layer.
Figure 9:
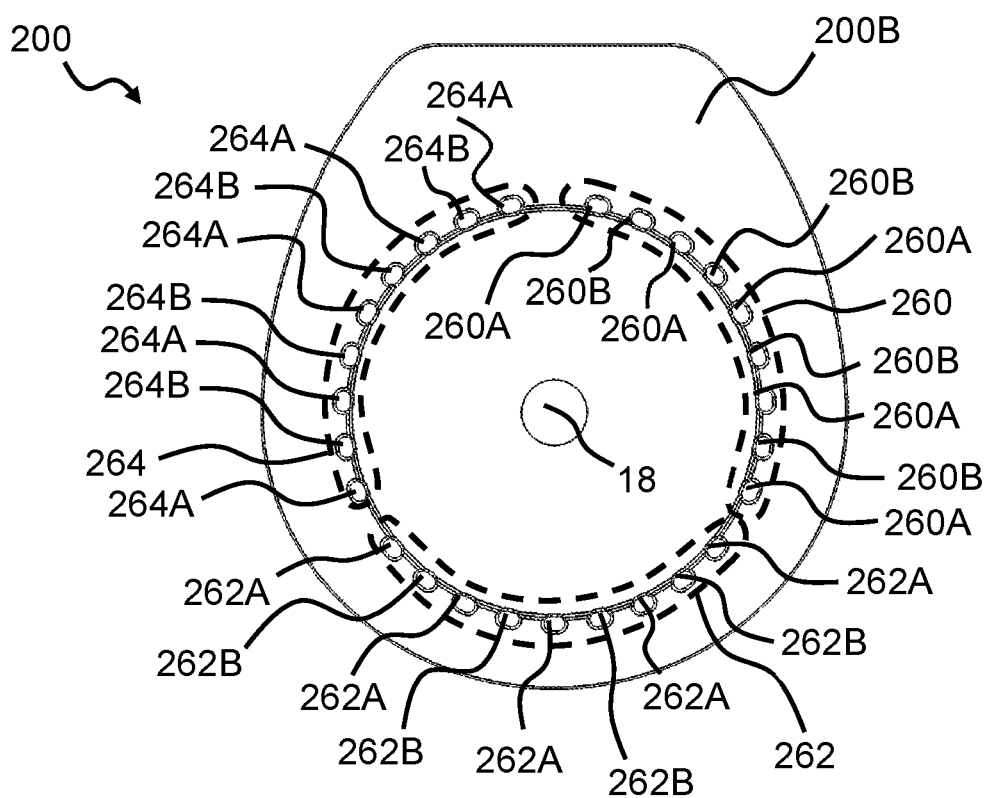
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
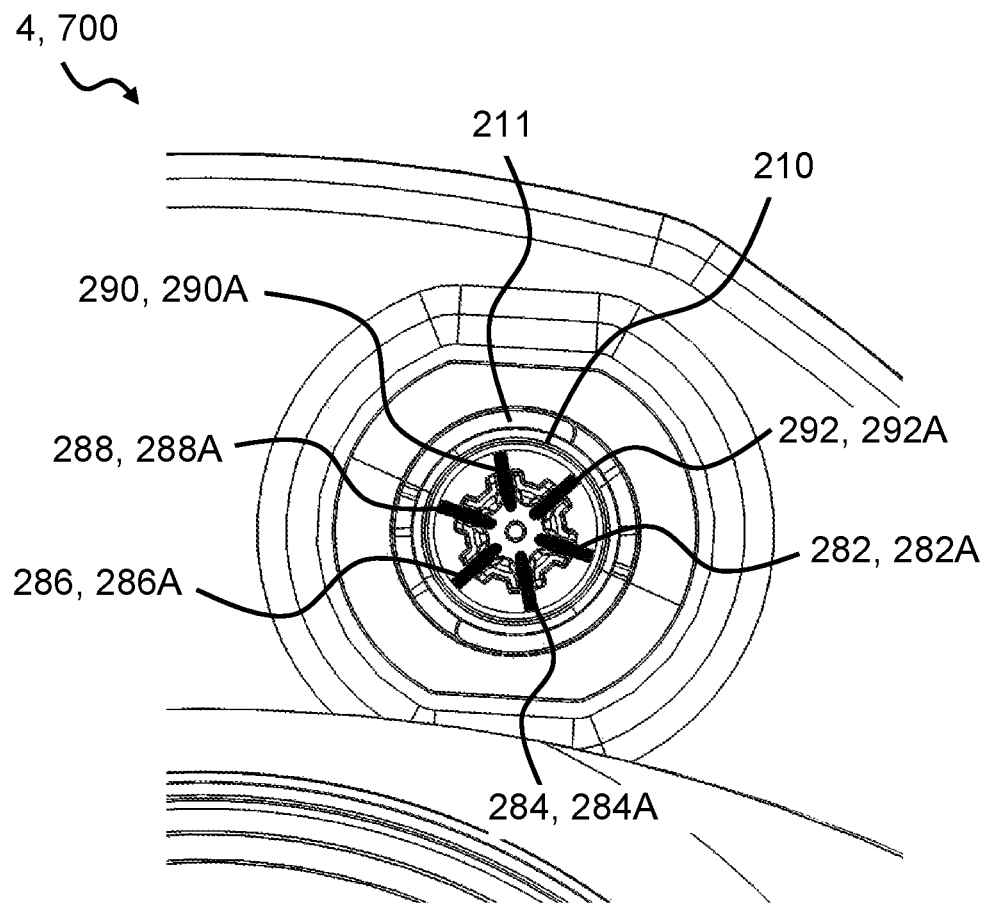
FIG. 10 is a distal view of a part of the base plate and/or sensor assembly part including a monitor interface.

FIG. 10 is a more detailed distal view of a part of the base plate 4 and/or the sensor assembly part 700. The base plate 4 and/or the sensor assembly part 700 comprises a monitor interface. The monitor interface comprises the first connector 211. The first connector 211 comprises coupling part 210 configured to releasably couple the monitor device to the base plate/or the sensor assembly part and thus forming a releasable coupling. The first connector 211 of the monitor interface comprises a plurality of terminals formed by respective terminal elements for forming respective electrical connections with respective terminals of the monitor device.

The plurality of terminals of the first connector 211 of the monitor interface comprises a ground terminal element 282 forming a ground terminal 282A, a first terminal element 284 forming a first terminal 284, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 292A. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate and/or the sensor assembly part, the number of terminals and the position of the terminals in the coupling part may be adapted to the electrode configuration used in the electrode assembly of the base plate and/or the sensor assembly part.

Figure 11:
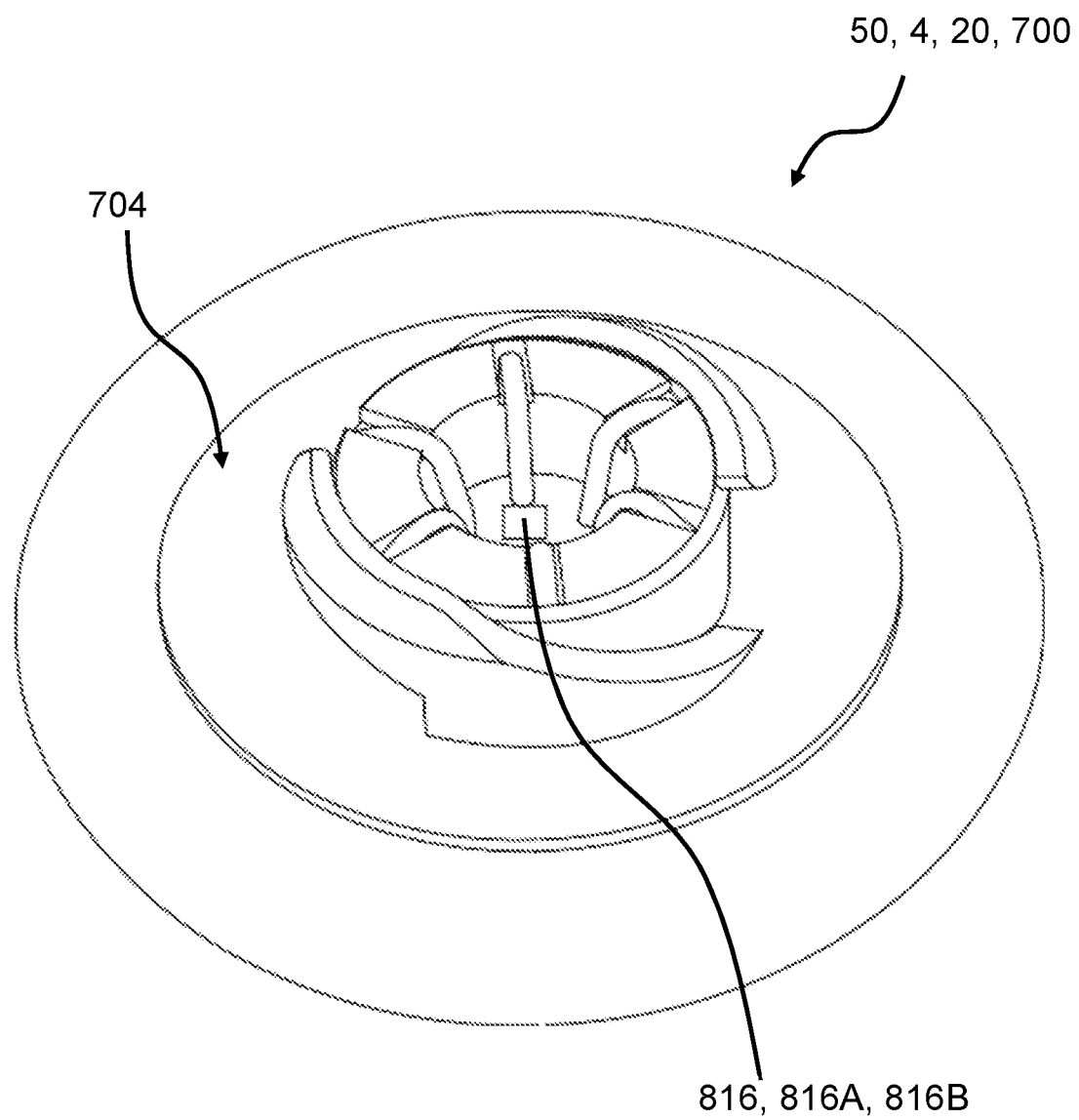
FIG. 11 is a distal view of an exemplary electrode configuration.

FIG. 11 illustrates an exemplary target device 50 having an identifier element 816. The target device 50 comprises a target device coupling part 704 configured to releasably and structurally couple the target device 50 to a monitor device. The target device 50 may be a base plate 4, or a sensor assembly part 700 for a base plate, as exemplified in relation to previous figures, e.g. FIG. 3. Alternatively, the target device 50 may be a docking station 20 as described in relation to previous figures, e.g. FIG. 1. The target device 50 may be one of a plurality of base plates, sensor assembly parts and/or docking stations. The target device 50 may be any device configured to be received by the monitor device. For example, one of the one or more base plates may comprise a base plate identifier element 816A, such as a base plate identifier element, whereas the docking station may comprise a docking station identifier element 816B, such as a docking station identifier element 816B. The others of the one or more base plates may each comprise another identifier element. The identifier element 816 of the target device 50 may be configured to engage with an identifier sensor of the monitor device, e.g. when the target device 50 is coupled to the monitor device. Additionally or alternatively, the identifier element 816 may be configured to be detected or identified by the identifier sensor of the monitor device such that the monitor device may identify which target device 50 (e.g. which of the plurality of base plates, sensor assembly parts or the docking stations) is being coupled to the monitor device.

As illustrated in FIG. 11, the identifier element 816 may be centrally disposed on or in the coupling part 704 of the target device 50. However, any reasonable disposition of the identifier element 816 on the target device 50 may be considered.

Figure 12:
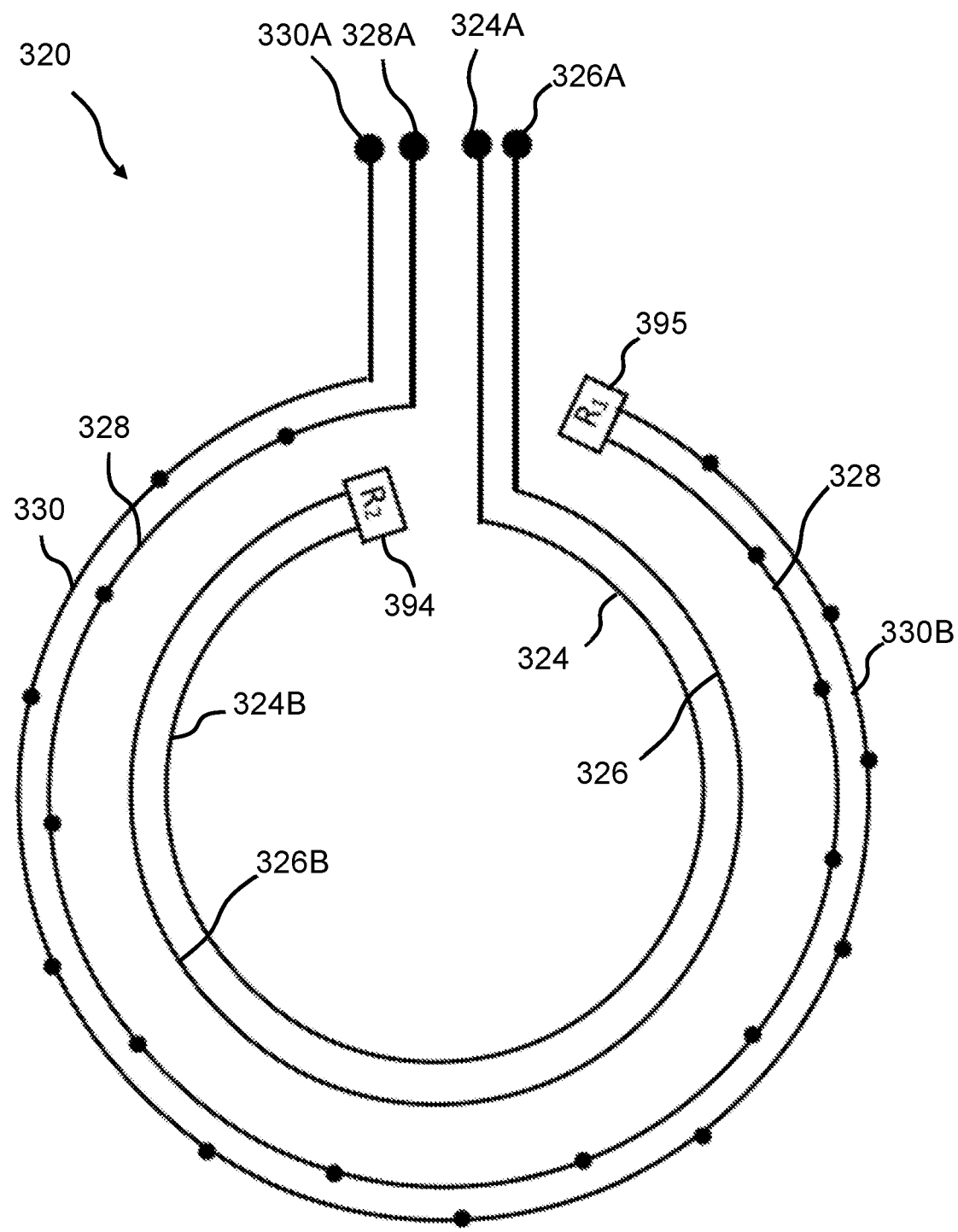
FIG. 12 is a distal view of an exemplary electrode configuration.

FIG. 12 is a distal view of an exemplary electrode configuration 320, for a base plate and/or a sensor assembly part, including identifier elements 394, 395. Electrode configuration 320 may be substituted for electrode configuration 220 of electrodes 216 in the electrode assembly 204, e.g. of FIG. 4 and/or 6. In addition, elements of electrode configuration 320, such as identifier elements 394, 395 may be added to electrode configuration 220 of electrodes 216 in the electrode assembly 204, The electrode configuration 320, as illustrated, comprises a first electrode 324, a second electrode 326, a third electrode 328, and a fourth electrode 330. Each of the electrodes 324, 326, 328, 330 comprise a sensing part and a connection part. The first electrode 324 comprises a first connection part 324A and a first sensing part 324B. The second electrode 326 comprises a second connection part 326A and a second sensing part 326B. The third electrode 328 comprises a third connection part 328A and a third sensing part 328B. The fourth electrode 330 comprises a fourth connection part 330A and a fourth sensing part 330B. In this manner, each electrode has a respective connection part for connecting the electrodes to respective terminal elements of a monitor device, such as a monitor interface of a monitor device.

With electrode configuration 320, any of first electrode 324, second electrode 326, third electrode 328, and fourth electrode 330 may be configured as ground electrodes or active sensing electrodes. For example, sensing may occur between adjacent or non-adjacent pairs of electrodes according to selections of a monitoring device, such as the monitor device 6 as disclosed in relation to other figures, e.g. FIG. 2, connected to first connection part 324A, second connection part 326A, third connection part 328A, and fourth connection part 330A. Such selectable electrode pairs may provide additional data useful for diagnosis and or monitoring of stoma output or leakage. Exemplary electrode pairs suitable for monitoring include: first electrode 324 and second electrode 326, first electrode 324 and third electrode 328, first electrode 324 and fourth electrode 330, second electrode 326 and third electrode 328, second electrode 326 and fourth electrode 330, as well as third electrode 328 and fourth electrode 330.

Electrode configuration 320 further includes identifier elements 394, 395, such as base plate identifier elements. The electrode configuration 320 comprises a first identifier element 394 and a second identifier element 395. First identifier element 394 is electrically coupled to first and second electrodes 324, 326. Second identifier element 395 is electrically coupled to third and fourth electrodes 328, 330. First and second identifier elements 394, 395 each represent base plate information that can be determined through the electrodes to which the identifier element is coupled. The identifier elements 394, 395 is located at the far end of the pair of electrodes, such as at the sensing part of the electrodes, such as at the far end of the sensing part of the electrodes.

The first and second identifier elements 394, 395 may be resistors, e.g. a first resistor having a first resistance R1 and a second resistor having a second resistance R2. The first resistance R1 may be the same as the second resistance R2 or the first resistance R1 may differ from the second resistance R2, e.g. by a measurable amount. Thus, the monitor device may be able to identify the electrode configuration 320 and/or the sensor assembly part and/or base plate comprising the electrode configuration 320 based on the measured resistances between the first connection part 324A and the second connection part 326A and/or the measured resistance between the third connection part 328A and the fourth connection part 330A.

With the placement of the resistors at the far ends of the electrode pairs, the entire length of the electrodes forming each electrode pair can be evaluated for operability. For example, the resistors may be constructed to generate different resistances, thereby allowing the processor to evaluate the resistance by comparing such values to known values, e.g. stored in memory, and thereby determine which pair of the electrodes is potentially inoperable. Thereafter, an appropriate warning or message can be provided to the user.

Capacitive elements may be used as alternatives to resistors, e.g., the identifier elements, such as the first identifier element 394 and/or the second identifier element 395 may be capacitive elements, or capacitive elements may be provided in addition to the illustrated resistors.

Figure 13:
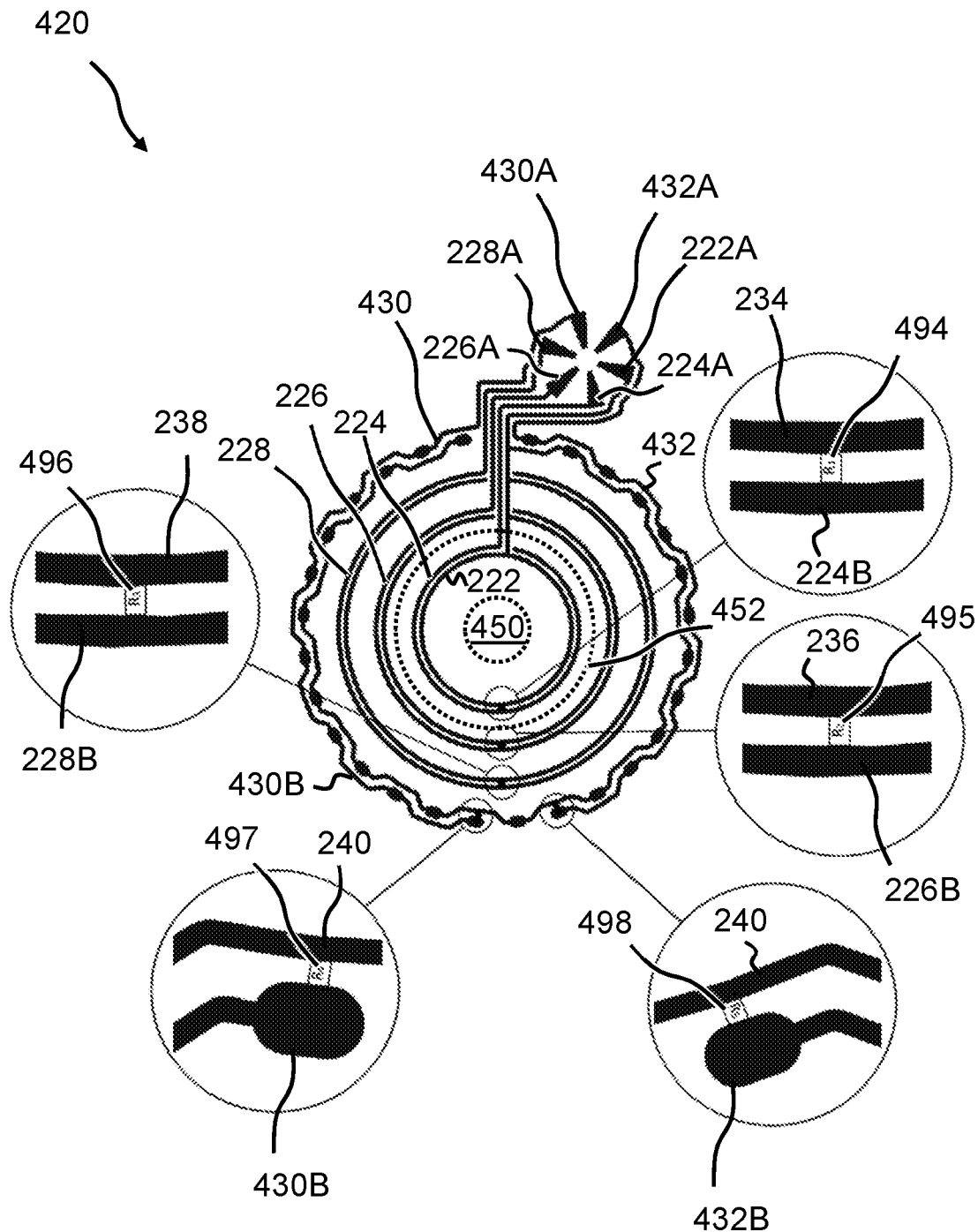
FIG. 13 is a distal view of an exemplary electrode configuration.

FIG. 13 shows distal view of an exemplary electrode configuration 420 including identifier elements 494, 495, 496, 497, 498. Electrode configuration 420 may be substituted for electrode configuration 220 of electrodes 216 in the electrode assembly 204, e.g. of FIG. 4 and/or 6. In addition, elements of electrode configuration 420, such as identifier elements 494, 495, 496, 497, 498 may be added to electrode configuration 220 of electrodes 216 in the electrode assembly 204 or substituted for identifier elements 394, 395 in electrode configuration 320, e.g. of FIG. 12.

The electrode configuration 420 comprises a ground electrode 222, a first electrode 224, a second electrode 226, a third electrode 228, a fourth electrode 430, and a fifth electrode 432. In this manner, electrode configuration 420 is similar to electrode configuration 220, e.g. of FIG. 4 and/or 6, except that the fourth electrode 430, and the fifth electrode 432 are arranged differently than with the fourth electrode 230, and the fifth electrode 232 of electrode configuration 220. In addition, as previously mentioned, electrode configuration 420 also includes identifier elements 494, 495, 496, 497, 498. Each electrode has a respective connection part for connecting the electrodes to respective terminal elements of the monitor interface, and a sensing part arranged with respect to the center for providing a stomal opening 450.

While described according to their intended uses, any of ground electrode 222, first electrode 224, second electrode 226, third electrode 228, fourth electrode 430, and fifth electrode 432 may be configured as ground electrodes or active sensing electrodes, i.e. resistance, capacitance, resonance frequency etc. may be measured between any pair of electrodes.

Electrode configuration 420 further includes identifier elements 494, 495, 496, 497, 498. Identifier elements 494, 495, 496, 497, 498 each represent base plate and/or sensor assembly part information that can be determined through the electrodes to which the identifier element is coupled. Identifier element 494 is electrically coupled to sensing part 224B of the first electrode 224 and first electrode part 234 of the ground electrode 222. Identifier element 495 is electrically coupled to sensing part 226B of the second electrode 226 and second electrode part 236 of the ground electrode 222. Identifier element 496 is electrically coupled to sensing part 228B of the third electrode 228 and third electrode part 238 of the ground electrode 222. Identifier element 497 is electrically coupled to sensing part 430B of the fourth electrode 430 and fourth electrode part 240 of the ground electrode 222. Identifier element 498 is electrically coupled to sensing part 432B of the fifth electrode 432 and fourth electrode part 240 of the ground electrode 222.

The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 430 comprises a fourth connection part 430A and the fifth electrode 432 comprise a fifth connection part 432A.

Ground connection part 222A, first connection part 224A, second connection part 226A, third connection part 228A, fourth connection part 430A and fifth connection part 432A are positioned adjacent one another at a monitor interface location spaced apart from the sensing parts 222B, 224B, 226B, 228B, 430B, 432B.

Identifier elements 494, 495, 496, 497, 498 can individually or collectively represent base plate and/or sensor assembly part information including one or more of base plate and/or sensory assembly part type, manufacturing batch, manufacture date and unique identification. Such information can be used by a monitoring device, coupled to the base plate and/or sensor assembly part comprising the electrode configuration 420, to associate sensor measurements with predicted outcomes, for example, by adjusting modelling according to properties of the base plate and/or sensor assembly part as indicated by the information.

In some implementations, identifier elements 494, 495, 496, 497, 498 may be electrical resistors. Thus, a monitoring device may detect the electrical resistance of identifier elements 494, 495, 496, 497, 498 upon connection to connection parts 222A, 224A, 226A, 228A, 430A, 432A. Identifier elements 494, 495, 496, 497, 498 may have the same selected resistance, or identifier elements 494, 495, 496, 497, 498 may have different selected resistances, and the combination of selected resistances may represent the information. The amount of information is limited by the possible combinations of preselected possible discrete resistances for identifier elements 494, 495, 496, 497, 498. For example, with the five identifier elements 494, 495, 496, 497, 498, and five possible discrete resistances, such as fifty megaohms, sixty megaohms, seventy megaohms, eighty megaohms and ninety megaohms, provides for 3125 unique combinations of baseplate identifiers (5^5=3125).

Identifier elements 494, 495, 496, 497, 498 are electrically connected near a far end of their respective sensing parts facilitating conductor integrity testing. Thereby, a detected resistance higher than any of the preselected discrete resistances used to encode information, may indicate either a poor connection between the monitor device and electrode configuration 420 or a fractured or cut conductor of one of the measured electrodes. Thus, measuring resistances between the ground electrode 222 and the first electrode 224, between the ground electrode 222 and the second electrode 226, between the ground electrode 222 and the third electrode 228, between the ground electrode 222 and the fourth electrode 430, and between the ground electrode 222 and the fifth electrode 432 may reveal if any of the electrodes are inoperable based on if a measured resistance is above a respective threshold value.

In alternative implementations, identifier elements 494, 495, 496, 497, 498 are capacitive elements. In such implementations, the preselected discrete capacitance of the different identifier elements 494, 495, 496, 497, 498 would represent the information. In contrast to implementations relying upon resistive elements, such capacitive elements will not interfere with resistive measurements.

In the same or different alternative implementations, identifier elements 494, 495, 496, 497, 498 may be provided between connection parts 222A, 224A, 226A, 228A, 430A, 432A. Such implementations may include resistive and/or capacitive elements for the identifier elements. While such implementations would provide base plate and/or sensor assembly part information, they would not also facilitate conductor integrity testing.

In the same or different alternative implementations, identifier elements 494, 495, 496, 497, 498 may include a circuit element configured to provide a multiple bit digital value or be replaced by a single circuit element configured to provide a multiple bit digital value. Such a configuration would provide for a much greater amount of information than with resistive and/or capacitive elements.

FIG. 13 further includes an indication of stomal opening 450, and an exemplary cut line 452, where a user might cut the base plate and/or sensor assembly part in order to fit the base plate and/or sensor assembly part to his/her stoma. In such situation, the sensing part 224B of first electrode 224, as well as the first electrode part 234 of the ground electrode 222, is cut away. Thus, monitoring the first electrode 224 will not reveal anything meaningful in terms of erosion or leakage of the base plate. However, the monitor device may initially query the first electrode 224, e.g. relative to the ground electrode 222, and find that the measured resistance, capacitance, resonance frequency etc. is not within an expected range and thereby detect that the first electrode 224 is inoperable. Thereby, the monitor device may be configured to only monitor the remaining electrodes.

As the identifier elements closer to the center, e.g. the first identifier element 494 and possibly the second identifier element 495 are more likely to be cut away by the user when customizing the stomal opening, information necessary for identification of the base plate and/or sensor assembly part could advantageously be provided by the other identifier elements, such as the third identifier element 496, the fourth identifier element 497 and/or the fifth identifier element 498.

Figure 14:
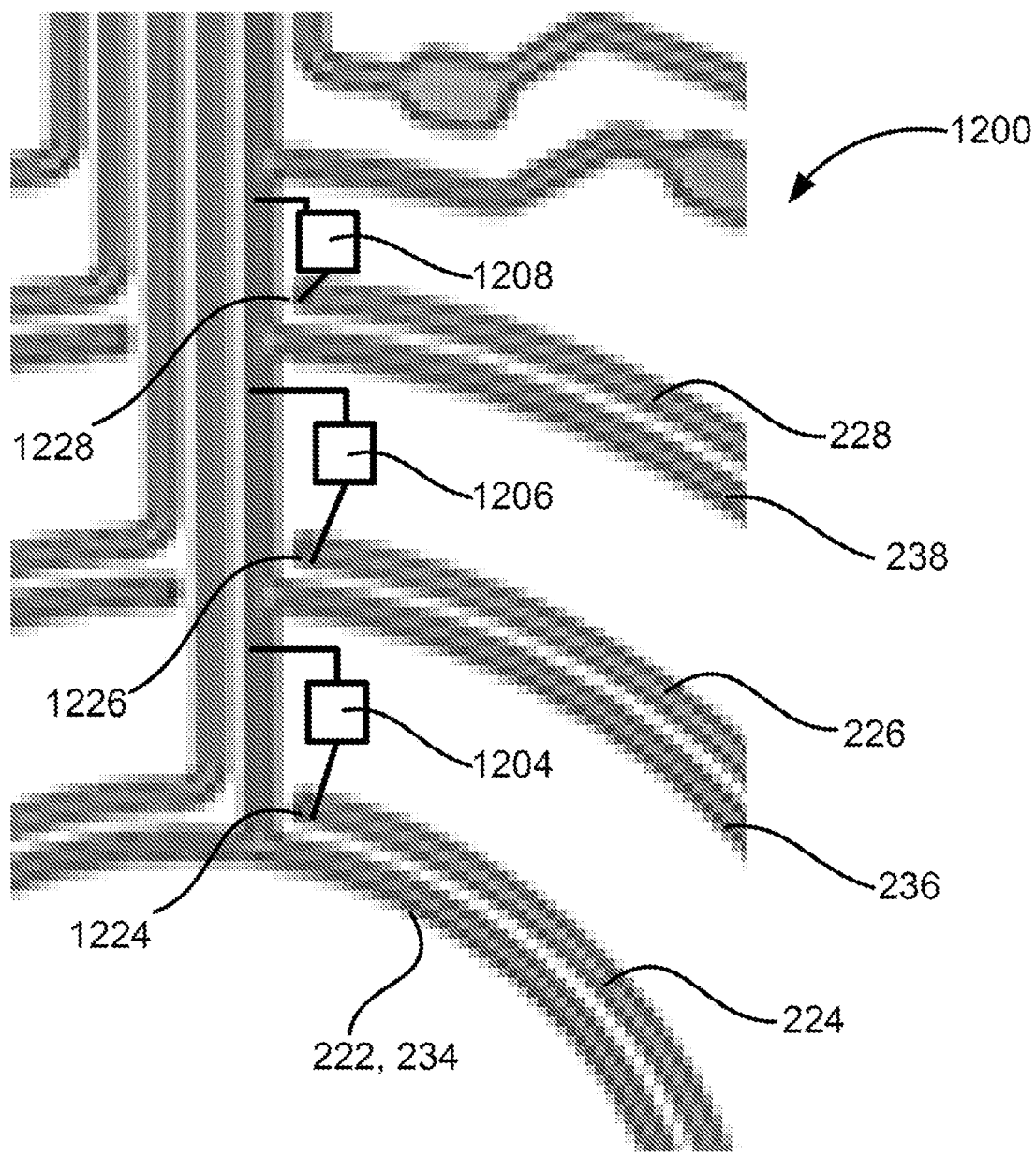
FIG. 14 shows an enlarged portion of an exemplary electrode configuration, FIG. 15 schematically illustrates an exemplary monitor device.

FIG. 14 shows an enlarged portion of the exemplary electrode configuration 220, as illustrated in FIG. 6. The electrode configuration 220 is shown with an exemplary identifier element configuration 1200. For example, the identifier elements may be resistors or capacitors.

The identifier element configuration 1200 include a first identifier element 1204 positioned between the ground electrode 222 and the first electrode 224 to allow a monitor device to query the associated electrodes and obtain one or more parameters based on a first identifier response received from the query of the first identifier element 1204 via the ground electrode 222 and the first electrode 224.

The identifier element configuration 1200 include a second identifier element 1206 positioned between the ground electrode 222 and the second electrode 226 to allow a monitor device to query the associated electrodes and obtain one or more parameters based on a second identifier response received from the query of the second identifier element 1206 via the ground electrode 222 and the second electrode 226.

The identifier element configuration 1200 include a third identifier element 1208 positioned between the ground electrode 222 and the third electrode 228 to allow a monitor device to query the associated electrodes and obtain one or more parameters based on a third identifier response received from the query of the third identifier element 1208 via the ground electrode 222 and the third electrode 228.

Additional identifier elements may be provided between other electrodes and/or other conducting elements, such as terminals and/or conducting parts electrically connected to the terminals, to assess the operability of such structures. Accordingly, and with reference to FIG. 6, an identifier element can be provided between the fourth electrode 230 and the fourth electrode part 240 of the ground electrode 222. Alternatively or additionally, an identifier element may be provided between the fifth electrode 232 and the fourth electrode part 240 of the ground electrode 222. Alternatively or additionally, an identifier element may be provided between the fourth electrode 230 and the fifth electrode 232.

Identifier elements 1204, 1206, 1208 may have a similar value, such as the same selected resistance. Alternatively, some or all of the identifier elements 1204, 1206, 1208 may have different values, such as different resistances.

The first identifier element 1204 can be positioned at and/or electrically interconnected to a far end 1224 of the first electrode 224, as illustrated. By electrically connecting the first identifier element 1204 at or near a far end 1224 of the first electrode 224, all or substantially all of the first electrode 224 can be assessed for operability. Similarly, the second identifier element 1206 can be positioned at and/or electrically interconnected to a far end 1226 of the second electrode 226, as illustrated. By electrically connecting the second identifier element 1206 at or near a far end 1226 of the second electrode 226, all or substantially all of the second electrode 226 can be assessed for operability. Likewise, the third identifier element 1208 can be positioned at and/or electrically interconnected to a far end 1228 of the third electrode 228, as illustrated. By electrically connecting the third identifier element 1208 at or near a far end 1228 of the first electrode 228, all or substantially all of the third electrode 228 can be assessed for operability.

Figure 15:
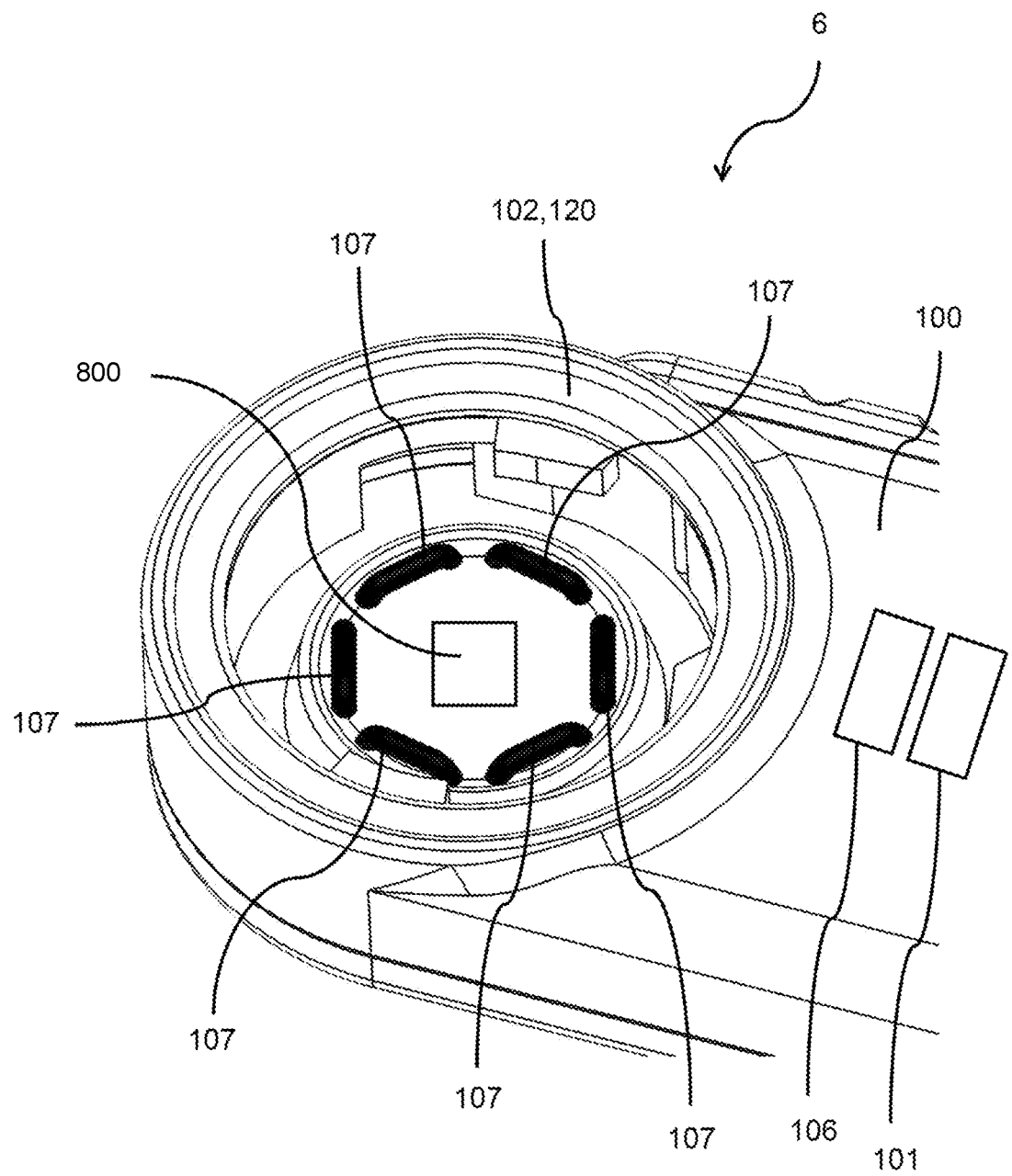

FIG. 15 schematically illustrates an exemplary monitor device 6. The monitor device 6 includes a housing 100, a processor 101, a first interface 102 and memory 106. The first interface 102 includes a coupling part 120 and a plurality of terminals 107. The coupling part 120 may be configured to releasably and structurally couple the monitor device 6 to the coupling part 210 of a base plate and/or a sensor assembly part, such as a base plate and/or sensor assembly part as described in relation to other figures. In addition, the plurality of terminals 107 of the monitor device 6 may be configured to be electrically coupled to respective terminals of the base plate and/or sensor assembly part. More particularly, the plurality of terminals 107 of the monitor device 6 may be configured to form electrical connections with the plurality of terminals 282, 284, 286, 288, 290 and 292 of the base plate 4 and/or sensor assembly part 700, as shown in FIG. 10. The coupling part 120 may also be configured to releasably and/or structurally couple the monitor device 6 to a docking station.

The monitor device 6 includes an identifier sensor 800. The identifier sensor 800 may be configured to detect and/or identify an identifier element of a target device, such as a base plate, sensor assembly part and/or docking station. The identifier sensor 800 may be a coupling sensor configured to detect coupling, such as correct and/or complete coupling, between the monitor device 6 and a target device, such as the base plate and/or the sensor assembly part and/or a docking station. Additionally or alternatively, the identifier sensor 800 may be configured to identify the target device that is being coupled to the monitor device 6. For example, the detection or identification may be performed when the monitor device 6 is coupled to the target device. Alternatively or additionally, the detection and/or identification may be performed without the monitor device 6 being coupled to the target device.

The identifier sensor 800 may be configured to cooperate with an identifier element, such as the identifier element 816 as illustrated in FIG. 11. More particularly, the monitor device identifier sensor 800 may form an electrical connection to the identifier element 816 as illustrated in FIG. 11. Accordingly, the processor 101 is configured to evaluate a connection parameter indicative of a mechanical connection quality between the monitor device 6 and the target device. In addition, an electrical connection between the monitor device 6 and the target device can also be assessed. Therefore, the processor 101 can determine if operability criteria are satisfied based on one or more connection parameters as compared to excepted values that are stored for reference in the memory 106.

As illustrated, the identifier sensor 800 may be centrally disposed on or in the coupling part 120 of the monitor device 6. However, any reasonable disposition of the identifier sensor 800 may be considered (e.g. on or in the housing 100).

Figure 16:
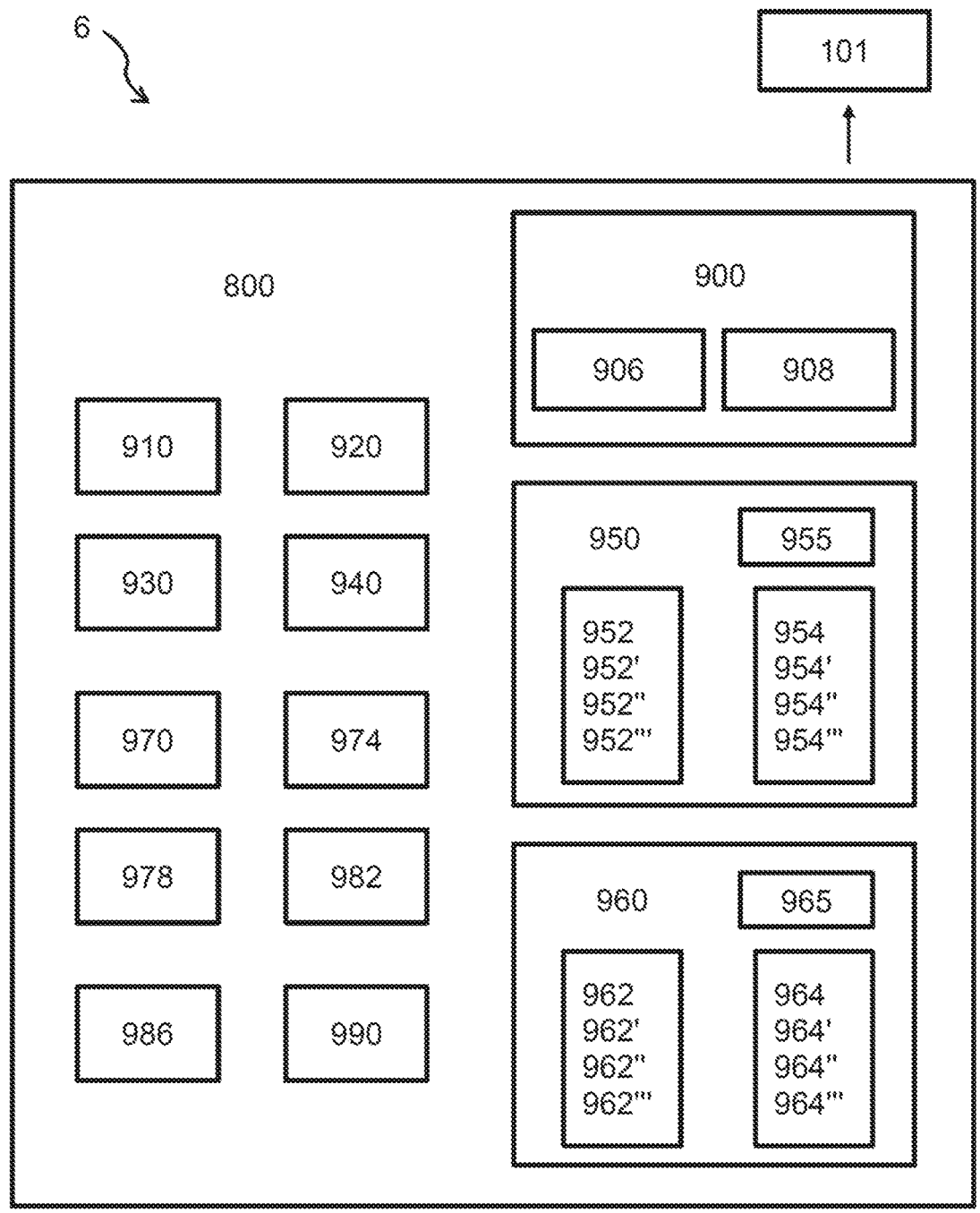
FIG. 16 illustrates an exemplary identifier sensor of a monitor device.

FIG. 16 illustrates an exemplary identifier sensor 800 of a monitor device, such as the monitor device as described in relation to FIG. 15. As previously described, the identifier sensor 800 may be configured to detect the coupling between the monitor device and a target device and/or identify the target device that is being coupled to the monitor device. To do so, the identifier sensor 800 may comprise at least one or more of a resistive sensor 900, a Hall sensor 910, a reed switch 920, an inductive sensor 930, a capacitive sensor 940, an ultrasonic sensor 950, a photoelectric sensor 960, a bar code reader 970, a magnetic strip reader 974, a variable depth ID reader 982, a variable depth ID reader 982, an RFID reader 986, and an NFC tag reader 990.

The coupling sensor 800 may be configured to generate a coupled signal and/or an identifier signal to be received by the processor 101 of the monitor device. The coupled signal may be generated when the identifier sensor 800 detects an identifier element of a target device (e.g. when the monitor device 6 is coupled to the target device) to indicate that the monitor device 6 is being coupled to the target device. The identifier signal may be indicative of certain information retrieved from the identifier element.

The processor 101 of the monitor device 6 may be configured to receive the coupled signal and/or the identifier signal from the coupling sensor 800 and determine that the target device is being coupled to the monitor device 6. The coupled signal may be in the form of voltage or current output. The determining step may comprise comparing the coupled signal and/or the identifier signal to a threshold value to determine a coupled state (e.g. when the coupled signal is greater or equal to the threshold value) or a decoupled state (e.g. when the coupled signal is lower than the threshold value).

The processor 101 of the monitor device 6 may be configured to receive the identifier signal from the identifier sensor 800 and determine which target device (e.g. which of one or more base plates, sensor assembly parts or a docking station) is coupled to the monitor device 6. The determining step may comprise comparing the identifier signal to a database content (e.g. from a database stored in the monitor device and/or on a remote server).

Figure 17:
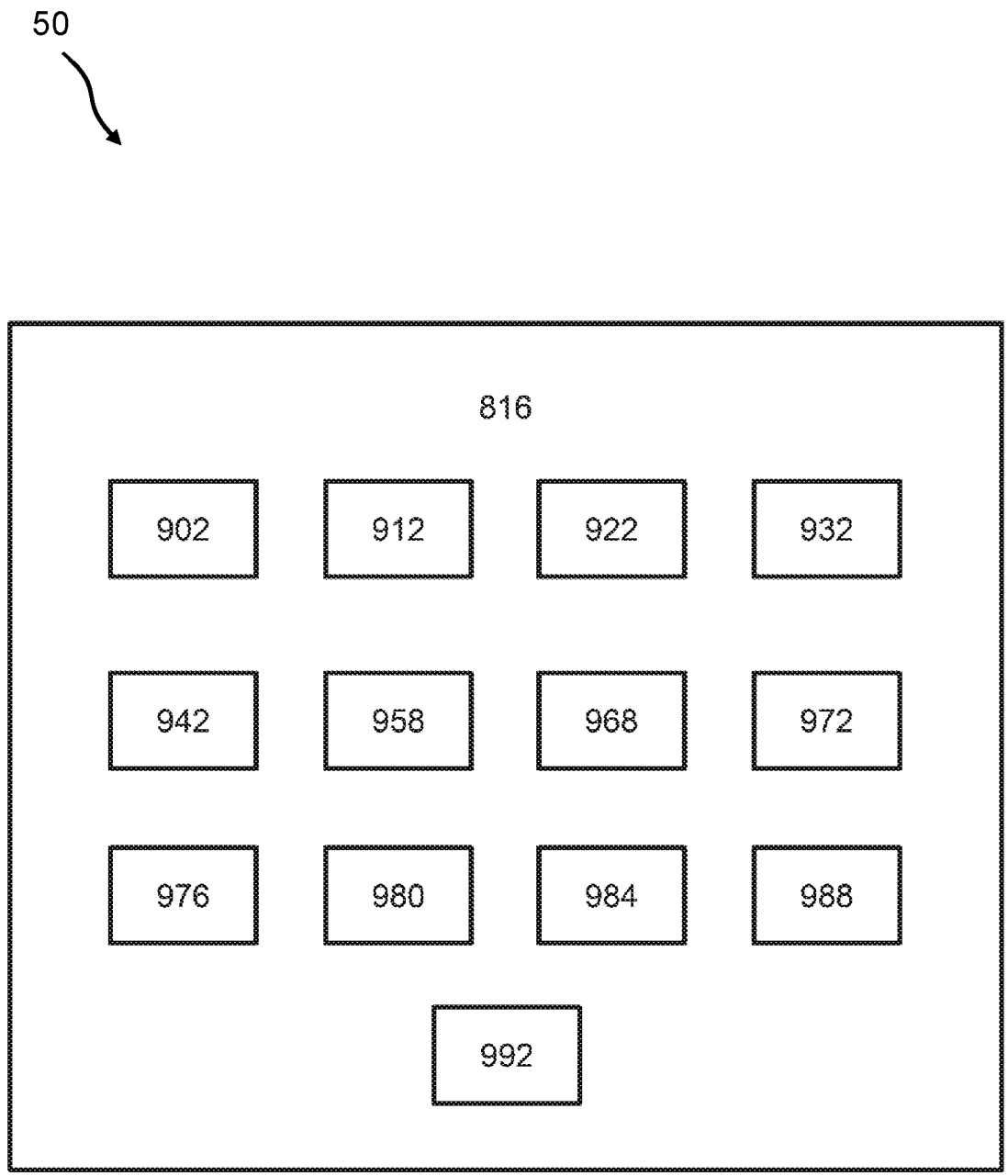
FIG. 17 illustrates an exemplary identifier element of a target device

FIG. 17 illustrates an exemplary identifier element 816 of a target device 50, such as a base plate, sensor assembly part and/or a docking station. The identifier element 816 may be a base plate identifier element 816A or a docking station identifier element 816B, as described in relation to FIG. 11. As previously described, the identifier element 816 may be configured to be queried, such as detected and/or identified by the identifier sensor 800 of the monitor device.

The identifier element 816 may comprise at least one or more of a target resistor 902, a target magnet 912, a turning magnet 922, a metallic actuator 932, a dielectric actuator 942, a sonic target 958, a photonic target 968, a reference bar code 972, a reference magnetic strip 976, a reference image ID 980, a reference variable depth ID 984, a reference RFID 988, a reference NFC tag 992, a QR code, and a colour code.

In reference to FIGS. 16 and 17, the identifier sensor 800 of the monitor device 6 may comprise a resistive sensor 900, whereas the identifier element 816 of the target device 50 may comprise a target resistor 902. The resistive sensor 900 may be configured to engage the target resistor 902 to measure a resistance. The resistive sensor 900 may include a first resistive sensor terminal 906 and a second resistive sensor terminal 908 configured to engage with the target resistor 902 of the target device 50. In embodiments, the first and second resistive sensor terminals 906, 908 of the resistive sensor 900 may be two of the plurality of terminals 107 of the monitor device 6, as illustrated in FIG. 15.

The resistive sensor 900 may be configured to generate the coupled signal to be received by the processor of the monitor device when the resistance measured by the resistive sensor 900 substantially matches a target resistance. The target resistance may be a calibrated resistance corresponding to the resistance measurable by the resistive sensor 900 when the monitor device and the target device 50 are coupled. In other embodiments, the coupled signal may be generated when the resistance measured is less than a threshold resistance.

In embodiments, the resistive sensor 900 of the monitor device 6 may transmit the measured resistance to the processor 101 of the monitor device, e.g. the identifier signal. The monitor device 6 may be configured to determine whether the target device and the monitor device are coupled and/or which of the target device is coupled to the monitor device, based on the resistance received from the resistive sensor 900, such as the identifier signal.

In reference to FIGS. 16 and 17, the identifier sensor 800 of the monitor device may comprise a Hall sensor 910, whereas the identifier element 816 of the target device 50 may comprise a target magnet 912. The Hall sensor 910 may be configured to engage the target magnet 912 to detect a magnetic flux density.

The Hall sensor 910 may be configured to generate the coupled signal to be received by the processor 101 of the monitor device 6 when the magnetic flux density detected by the Hall sensor 910 substantially matches a target magnetic flux density. The target magnetic flux density may be a calibrated magnetic flux density corresponding to the magnetic flux density detectable by the Hall sensor 910 when the monitor device 6 and the target device 50 are coupled. In other embodiments, the coupled signal may be generated when the magnetic flux density detected is larger than a threshold magnetic flux density.

In reference to FIGS. 16 and 17, the identifier sensor 800 of the monitor device 6 may comprise a reed switch 920, whereas the identifier element 816 of the target device 50 may comprise a turning magnet 922. The reed switch 920 may be configured to engage the turning magnet 922 and be triggered when the monitor device is coupled to the target device 50, due to the magnetic field of the turning magnet.

The reed switch 920 may be configured to switch from an open circuit to a closed circuit when the monitor device 6 is coupled to the target device 50. The reed switch 920 may be configured to generate the coupled signal to be received by the processor of the monitor device 6 when the reed switch is triggered. The coupled signal may be in the form of electrical charge transmittable through the closed circuit indicative of a triggered reed switch 920, indicative of the coupling between the target device 50 and the monitor device.

In reference to FIGS. 16 and 17, the identifier sensor 800 of the monitor device 6 may comprise an inductive sensor 930, whereas the identifier element 816 of the target device 50 may comprise a metallic actuator 932. In embodiments, the metallic actuator 932 may be ferrous (steel), in others the metallic actuator may be nonferrous (e.g. aluminium, copper, stainless steel, brass). The inductive sensor 930 may be configured to engage the metallic actuator 932 and detect a change in oscillation amplitude and/or resonance frequency in the inductive sensor 930 when the monitor device is coupled to the target device 50.

The inductive sensor 930 may be configured to detect the metallic actuator 932 by way of detecting a change from having a first oscillation amplitude and/or a first resonance frequency to having a second oscillation amplitude (e.g. approximately zero) and/or having a second resonance frequency when the metallic actuator 932 is sufficiently near the inductive sensor 930 (e.g. when the monitor device 6 is coupled to a target device).

The inductive sensor 930 may be further configured to generate the coupled signal to be received by the processor 101 of the monitor device 6 when the change in oscillation amplitude and/or resonance frequency detected by the inductive sensor 930 substantially matches a target change in oscillation amplitude and/or resonance frequency. The target change in oscillation amplitude and/or resonance frequency corresponds to the change in oscillation amplitude and/or resonance frequency detectable by the inductive sensor 930 when the monitor device 6 and the target device 50 are coupled, respectively.

The inductive sensor 930 may be configured to detect a plurality of metallic actuators, e.g., each having one of a plurality of ferrite contents. In embodiments, the inductive response in oscillation amplitude and/or resonance frequency of the inductive sensor differs between more ferrous and less ferrous materials. The inductive sensor 930 may be further configured to generate the identifier signal to be received by the processor 101 of the monitor device 6 indicative of the different inductive response correlating to which of the metallic actuator has engaged the inductive sensor. Each of such plurality of metallic actuators may correspond to one of the various target devices (e.g. one or more base plates, sensor assembly parts or docking stations). For example, one of the plurality of base plates may comprise a first metallic actuator, and/or a docking station may comprise a second metallic actuator. The processing unit 101 may, based on the identifier signal from the inductive sensor 930, identify which target device 50 is coupled to the monitor device 6.

In reference to FIGS. 16 and 17, the identifier sensor 800 of the monitor device 6 may comprise a capacitive sensor 940, whereas the identifier element 816 of the target device 50 may comprise a dielectric actuator 942. In embodiments, the dielectric actuator 942 may comprise material having dielectric constant greater than that of the material of the coupling parts of the monitor device and of the base plate. For example, the dielectric actuator 942 may comprise alumina and/or titanates. The capacitive sensor 940 may be configured to engage the dielectric actuator 942 and detect a change in oscillation amplitude and/or resonance frequency in the capacitive sensor 940 when the monitor device is coupled to the target device 50.

The capacitive sensor 940 may be configured to detect the dielectric actuator 942 by way of detecting a change from having a first oscillation amplitude (e.g. approximately zero) and/or a first resonance frequency to having a second oscillation amplitude and/or a second resonance frequency when the dielectric actuator 942 is sufficiently near the capacitive sensor 940 (e.g. when the monitor device is coupled to a target device).

The capacitive sensor 940 may be further configured to generate the coupled signal to be received by the processor 101 of the monitor device 6 when the change in oscillation amplitude and/or resonance frequency detected by the capacitive sensor 940 substantially matches a target change in oscillation amplitude and/or resonance frequency. The target change in oscillation amplitude and/or resonance frequency corresponds to the change in oscillation amplitude and/or resonance frequency detectable by the capacitive sensor 940 when the monitor device and a target device are coupled, respectively.

The capacitive sensor 940 may be configured to detect a plurality of dielectric actuators, e.g., each having one of a plurality of dielectric constants. In embodiments, the capacitive response in oscillation amplitude and/or resonance frequency of the capacitive sensor differs between materials with higher and lower dielectric constants. The capacitive sensor 940 may be further configured to generate the identifier signal to be received by the processor 101 of the monitor device 6 indicative of the different capacitive response correlating to which of the dielectric actuator has engaged the capacitive sensor. Each of the plurality of dielectric actuators corresponds to one of the various target devices (e.g. one or more base plates or docking stations). For example, one of the plurality of base plates may comprise a first dielectric actuator, and/or a docking station may comprise a second dielectric actuator. The processing unit 101 may, based on the identifier signal from the capacitive sensor 940, identify which target device 50 is coupled to the monitor device.

In reference to FIGS. 16 and 17, the identifier sensor 800 of the monitor device 6 may comprise an ultrasonic sensor 950, whereas the identifier element 816 of the target device 50 may comprise a sonic target 958. The ultrasonic sensor 950 may include an emitter 952 and a receiver 954, the emitter 952 being configured to emit sonic pulses to be received by the receiver 954 with or without passing through or reflecting off a sonic target 958 of the target device 50 located on a sensing path. The sonic target 958 may be sound-reflective and/or sound-absorbent. The ultrasonic sensor 950 may be one of a diffuse ultrasonic sensor 950', a retro-reflective ultrasonic sensor 950", or a through-beam ultrasonic sensor 950"'.

In embodiments where the ultrasonic sensor 950 is a diffuse ultrasonic sensor 950', the emitter 952' may be configured to emit sonic pulses along the sensing path where, when the sonic target 958 of the target device 50 enters the sensing path (e.g. when the monitor device is coupled to the target device 50), at least part of the sonic pulses will be reflected towards the receiver 954' of the diffuse ultrasonic sensor 950'. The diffuse ultrasonic sensor 950' may be configured to generate the coupled signal to be received by the processor 101 of the monitor device 6 when the at least part of the sonic pulses is received by the receiver 954', indicative of the sonic target 958 of the target device 50 being on the sensing path (e.g. when the monitor device is coupled to the target device 50).

In embodiments where the ultrasonic sensor 950 is a retro-reflective ultrasonic sensor 950", the emitter 952" may be configured to emit sonic pulses towards the receiver 954" by way of reflecting off a fixed reflector 955 of the retro-reflective ultrasonic sensor 950". The sensing path of such retro-reflective ultrasonic sensor 950" may be from the emitter 952" to the fixed reflector 955 to the receiver 954". When the sonic target 958 of the target device 50 enters the sensing path (e.g. when the monitor device is coupled to the target device 50), at least part of the sonic pulses may be reflected and/or absorbed by the sonic target 958, causing the remaining parts of the sonic pulses received by the receiver 954" to have different wave characteristics (e.g. amplitude) than the sonic pulses emitted by the emitter in totality, which would have been received by the receiver 954" if the sonic target 958 was absent from the sensing path. The retro-reflective ultrasonic sensor 950" may be configured to generate the coupled signal to be received by the processor of the monitor device when such change in wave characteristics is detected by the receiver 954", indicative of the sonic target 958 of the target device 50 being on the sensing path (e.g. when the monitor device is coupled to the target device 50).

In embodiments where the ultrasonic sensor 950 is a through-beam ultrasonic sensor 950"', the emitter 952"' may be configured to emit sonic pulses towards the receiver 954"' along the sensing path (i.e. from the emitter 952"' to the receiver 954"'). When the sonic target 958 of the target device 50 enters the sensing path (e.g. when the monitor device 6 is coupled to the target device 50), at least part of the sonic pulses may be reflected and/or absorbed by the sonic target 958 causing the remaining parts of the sonic pulses received by the receiver 954"' to have different wave characteristics (e.g. amplitude) than the totality of the sonic pulses that would have been received by the receiver 954"' without the sonic target 958 on the sensing path. The through-beam ultrasonic sensor 950"' may be configured to generate the coupled signal to be received by the processor 101 of the monitor device 6 when such change in wave characteristics is detected by the receiver 954"', indicative of the sonic target 958 of the target device 50 being on the sensing path (e.g. when the monitor device 6 is coupled to the target device 50).

In reference to FIGS. 16 and 17, the identifier sensor 800 of the monitor device 6 may comprise a photoelectric sensor 960, whereas the identifier element 816 of the target device 50 may comprise a photonic target 968. The photoelectric sensor 960 may include an emitter 962 and a receiver 964. The emitter 962 being configured to emit a light beam to be received by the receiver 964 with or without passing through and/or reflecting off a photonic target 968 of the target device 50 located on a sensing path. The photonic target 968 may be light-reflective and/or light-absorbent. The photoelectric sensor 960 may be one of a diffuse photoelectric sensor 960', a retro-reflective photoelectric sensor 960", or a through-beam photoelectric sensor 960"'.

In embodiments where the photoelectric sensor 960 is a diffuse photoelectric sensor 960', the emitter 962' may be configured to emit a light beam along the sensing path where, when the photonic target 968 of the target device 50 enters the sensing path (e.g. when the monitor device 6 is coupled to the target device 50), at least part of the light beam will be reflected towards the receiver 964' of the diffuse photoelectric sensor 960'. The diffuse photoelectric sensor 960' may be configured to generate the coupled signal to be received by the processor 101 of the monitor device 6 when the at least part of the light beam is received by the receiver 964', indicative of the photonic target 968 of the target device 50 being on the sensing path (e.g. when the monitor device is coupled to the target device 50).

In embodiments where the photoelectric sensor 960 is a retro-reflective photoelectric sensor 960", the emitter 962" may be configured to emit a light beam towards the receiver 964" by way of reflecting off a fixed reflector 955 of the retro-reflective photoelectric sensor 960". The sensing path of such retro-reflective photoelectric sensor 960" may be from the emitter 962" to the fixed reflector 965 to the receiver 964". When the photonic target 968 of the target device 50 enters the sensing path (e.g. when the monitor device 6 is coupled to the target device 50), at least part of the light beam may be reflected and/or absorbed by the photonic target 968, causing the remaining parts of the light beam received by the receiver 964" to have different wave characteristics (e.g. amplitude) than the light beam emitted by the emitter in totality, which would have been received by the receiver 964" when the photonic target 968 is absent on the sensing path. The retro-reflective photoelectric sensor 960" may be configured to generate the coupled signal to be received by the processor 101 of the monitor device 6 when such change in wave characteristics is detected by the receiver 964", indicative of the photonic target 968 of the target device 50 being on the sensing path (e.g. when the monitor device 6 is coupled to the target device 50).

In embodiments where the photoelectric sensor 960 is a through-beam photoelectric sensor 960''', the emitter 962''' may be configured to emit a light beam towards the receiver 964''' along the sensing path (i.e. from the emitter 962''' to the receiver 964"). When the photonic target 968 of the target device 50 enters the sensing path (e.g. when the monitor device 6 is coupled to the target device 50), at least part of the light beam may be reflected and/or absorbed by the photonic target 968 causing the remaining parts of the light beam received by the receiver 964''' to have different wave characteristics (e.g. amplitude) than the totality of the light beam that would have been received by the receiver 964''' without the photonic target 968 on the sensing path. The through-beam photoelectric sensor 960''' may be configured to generate the coupled signal to be received by the processor 101 of the monitor device 6 when such change in wave characteristics is detected by the receiver 964''', indicative of the photonic target 968 of the target device 50 being on the sensing path (e.g. when the monitor device 6 is coupled to the target device 50).

In reference to FIGS. 16 and 17, the identifier sensor 800 of the monitor device 6 may comprise a bar code reader 970, whereas the identifier element 816 of the target device 50 may comprise a reference bar code 972. The bar code reader 970 may be configured to detect and/or identify the reference bar code 972.

The bar code reader 970 may be configured to generate the identifier signal to be received by the processor of the monitor device indicative of the reference bar code 972 being identified and/or detected.

The reference bar code 972 may be one of a plurality of reference bar codes. Each of the plurality of reference bar codes may correspond to one of the various target devices (e.g. one or more base plates or docking stations). For example, one of the plurality of base plates may comprise a first reference bar code, and/or a docking station may comprise a second reference bar code. The processing unit 101 may, based on the identifier signal received from the bar code reader 970, identify which target device 50 is coupled to the monitor device.

In reference to FIGS. 16 and 17, the identifier sensor 800 of the monitor device 6 may comprise a magnetic strip reader 974, whereas the identifier element 816 of the target device 50 may comprise a reference magnetic strip 976. The magnetic strip reader 974 may be configured to detect and/or identify the reference magnetic strip 976.

The magnetic strip reader 974 may be configured to generate the identifier signal to be received by the processor 101 of the monitor device 6 indicative of the reference magnetic strip 976 being identified and/or detected.

The reference magnetic strip 976 may be one of a plurality of reference magnetic strips. Each of the plurality of reference magnetic strips corresponds to one of the various target devices (e.g. one or more base plates or docking stations). For example, one of the plurality of base plates may comprise a first reference magnetic strip, and a docking station may comprise a second reference magnetic strip. The processing unit 101 may, based on the identifier signal received from the magnetic strip reader 974, identify which target device 50 is coupled to the monitor device.

In reference to FIGS. 16 and 17, the identifier sensor 800 of the monitor device 6 may comprise an image ID reader 978, whereas the identifier element 816 of the target device 50 may comprise a reference image ID 980. The image ID reader 978 may be configured to detect or identify the reference image ID 980.

The image ID reader 978 may be configured to generate the identifier signal to be received by the processor 101 of the monitor device 6 indicative of the reference image ID 980 identified and/or detected.

The reference image ID 980 may be one of a plurality of reference image IDs. Each of the plurality of reference image IDs corresponds to one of the various target devices (e.g. one or more base plates and/or docking stations). For example, one of the plurality of base plates may comprise a first reference image ID, and a docking station may comprise a second reference image ID. The processing unit 101 may, based on the identifier signal received from the image ID reader 978, identify which target device 50 is coupled to the monitor device.

In reference to FIGS. 16 and 17, the identifier sensor 800 of the monitor device 6 may comprise a variable depth ID reader 982, whereas the identifier element 816 of the target device 50 may comprise a reference variable depth ID 984. In embodiments, the reference variable depth ID 984 of the target device 50 may comprise one or more regions with a first depth or height and one or more regions with a second depth or height. The variable depth ID reader 982 may be configured to detect or identify the reference variable depth ID 984.

The variable depth ID reader 982 may be configured to generate the identifier signal to be received by the processor 101 of the monitor device 6 indicative of the reference variable depth ID 984 being detected.

The reference variable depth ID 984 may be one of a plurality of reference variable depth IDs. Each of the plurality of reference variable depth IDs corresponds to one of the various target devices (e.g. one or more base plates and/or docking stations). For example, one of the plurality of base plates may comprise a first reference image ID, and a docking station may comprise a second reference image ID. For example, one of the one or more base plates may comprise a first reference image ID, and the docking station 20 may comprise a second reference image ID. The processing unit 101 may, based on the identifier signal received from the variable depth ID reader 982, identify which target device 50 is coupled to the monitor device.

In reference to FIGS. 16 and 17, the identifier sensor 800 of the monitor device 6 may comprise a RFID reader 986, whereas the identifier element 816 of the target device 50 may comprise a reference RFID 988. The RFID reader 986 may be configured to detect or identify the reference RFID 988.

The RFID reader 986 may be configured to generate the identifier signal to be received by the processor 101 of the monitor device 6 indicative of the reference RFID 988 detected and/or identified.

The reference RFID 988 may be one of a plurality of reference RFIDs. Each of the plurality of reference RFIDs corresponds to one of the various target devices (e.g. one or more base plates and/or docking stations). For example, one of the plurality of base plates may comprise a first reference RFID, and a docking station may comprise a second reference RFID. The processing unit 101 may, based on the identifier signal received from the RFID reader 986, identify which target device 50 is coupled to the monitor device 6.

In reference to FIGS. 16 and 17, the identifier sensor 800 of the monitor device 6 may comprise a NFC tag reader 990, whereas the identifier element 816 of the target device 50 may comprise a reference NFC tag 992. The NFC tag reader 990 may be configured to detect or identify the reference NFC tag 992.

The NFC tag reader 990 may be configured to generate the identifier signal to be received by the processor 101 of the monitor device 6 indicative of the NFC tag 992 detected.

The reference NFC tag 992 may be one of a plurality of reference NFC tags. Each of the plurality of reference NFC tags corresponds to one of the various target devices (e.g. one or more base plates or docking stations). For example, one of the plurality of base plates may comprise a first reference NFC tag, and a docking station may comprise a second reference NFC tag. The processing unit 101 may, based on the identifier signal received from the NFC tag reader 990, identify which target device 50 is coupled to the monitor device 6.

Figure 18:
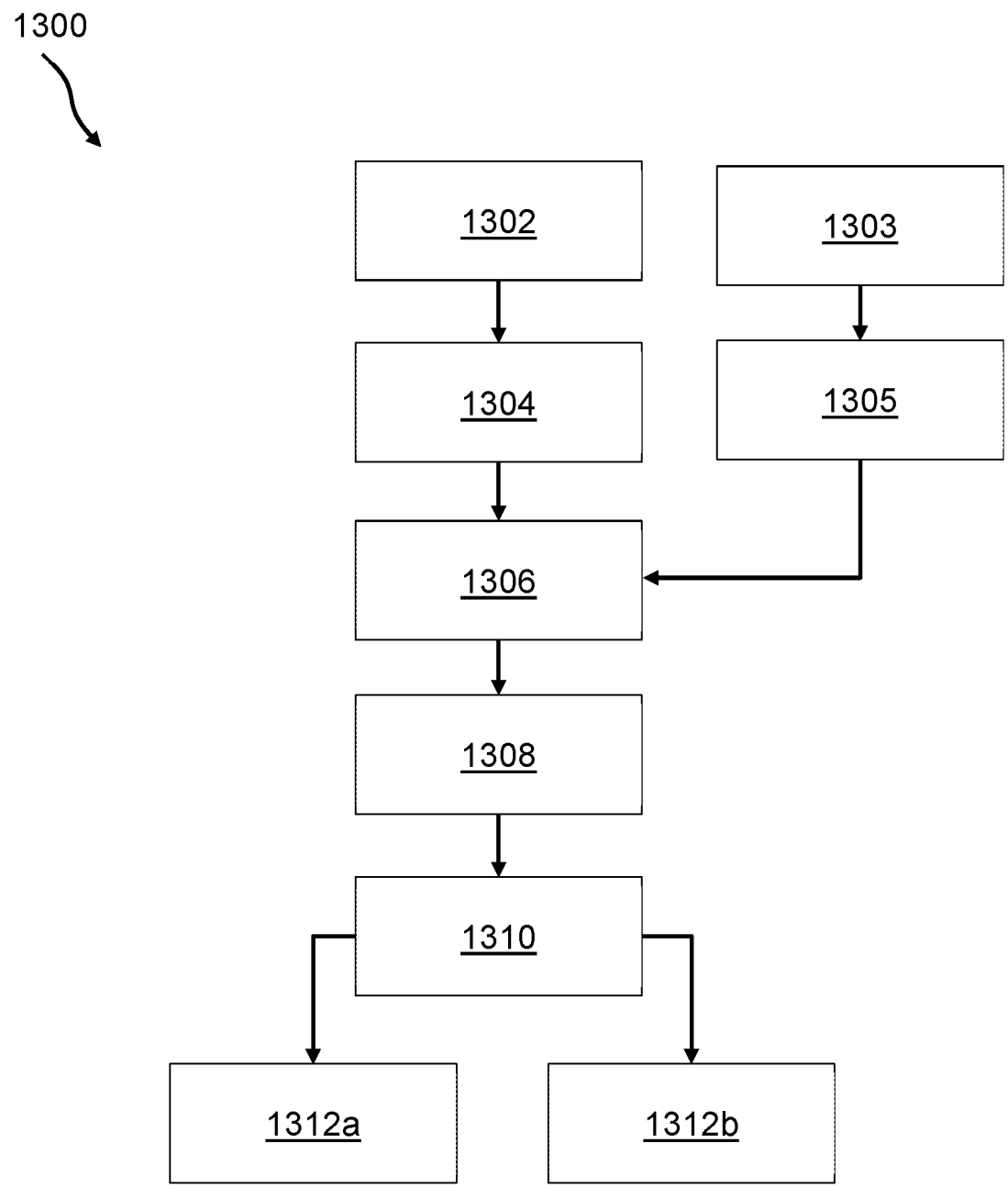
FIG. 18 is a flowchart of an exemplary method.

FIG. 18 is a flowchart of an exemplary method 1300 for operating a monitor device, such as a monitor device 6 as described in relation to the previous figures, such as a monitor device configured to be connected to target device, such as a base plate of an ostomy appliance, a sensor assembly part of the base plate and/or a docking station, and wherein the target device has a monitor interface; and a first identifier element. The method 1300 comprises querying 1302 the first identifier element, receiving 1304 a first identifier response from the first identifier element, and obtaining 1306 one or more parameters based on the first identifier response.

Concurrently (as shown), or sequentially with querying 1302 the first identifier element and receiving 1304 the first identifier response, the method 1300 may comprise querying 1303 other identifier elements, such as a second identifier element and/or a third identifier element, and receiving 1305 other identifier responses from the other identifier elements, such as a second identifier response from the second identifier element and/or a third identifier response from the third identifier element. Obtaining 1306 the one or more parameters may additionally and/or alternatively be based on the other identifier responses received 1305.

Querying 1302 the first identifier element and/or querying 1303 the other identifier elements may be utilized in accordance with the type of the identifier element implemented on the target device. For example, such as exemplified in more detail with respect to FIGS. 11-17. In particular, querying 1302, 1303 may comprise measuring a resistive value indicative of a resistance between a terminal pair of the monitor interface, whereby the received 1304, 1305 identifier response is the resistive value. Alternatively or additionally querying 1302, 1303 may comprise measuring a capacitive value indicative of a capacitance between a terminal pair of the monitor interface, whereby the received 1304, 1305 identifier response is the capacitive value. Alternatively or additionally, querying 1302, 1303 may comprise measuring a resonance frequency value indicative of a resonance frequency between a terminal pair of the monitor interface, whereby the received 1304, 1305 identifier response is the resonance frequency value.

The one or more parameters obtained 1306 may be indicative of a type of the target device, such as a type of base plate or type of sensor assembly part, and/or the type of the target device may reveal if the target device is a base plate, a sensor assembly part or a docking station. Alternatively or additionally, the one or more parameters obtained 1306 may be indicative of manufacturing batch of the target device. Alternatively or additionally, the one or more parameters obtained 1306 may be indicative of manufacturing date of the target device. Alternatively or additionally, the one or more parameters obtained 1306 may be indicative of a unique identifier of the target device, such as a unique identification number. Alternatively or additionally, the one or more parameters may be indicative of the monitor device being fully, or not fully, connected to the target device.

Obtaining 1306 the one or more parameters may be utilized by comparing the received 1304, 1305 identifier response(s) to known values. For example, obtaining 1306 the one or more parameters may include retrieving the one or more parameters from a memory of the monitor device, e.g. based on the received 1304, 1305 identifier response(s). Alternatively or additionally, obtaining 1306 the one or more parameters may include retrieving the one or more parameters from a remote device, e.g. an accessory device and/or a remote server. Thus, obtaining 1306 the one or more parameters may include transmitting a request signal based on the received 1304, 1305 identifier response(s) to the remote device and receiving the one or more parameters from the remote device. Alternatively or additionally, the identifier response(s) may be factors in an algorithm for obtaining 1306 the one or more parameters, i.e. the monitor device may calculate one or more of the one or more parameters based on the received 1304, 1305 identifier response(s). Alternatively or additionally, the identifier response(s) may be directly indicating the one or more parameters. For example a digital response received from an NFC chip may be the unique identification number constituting one of the one or more parameters.

The monitor device may be configured in accordance with the obtained 1306 one or more parameters. For example, the obtained 1306 one or more parameters may be indicative of how data should be collected from the base plate and/or sensor assembly part. For example, as also described above, the one or more parameters may be indicative of one or more of the electrodes being inoperable. Thus, the method 1300 may comprise collecting 1308 ostomy data representative of a condition of the ostomy appliance, and the collecting 1308 of ostomy data may be based on a data collection scheme, wherein the data collection scheme may be determined based on the obtained 1306 one or more parameters. Alternatively or additionally, the obtained 1306 one or more parameters may be indicative of how collected 1308 ostomy data is to be processed. For example, the obtained 1306 one or more parameters may comprise information of correspondence between terminals and electrodes, i.e. the obtained 1306 one or more parameters may be used in order to properly process and evaluate the collected 1308 ostomy data. Thus, the method 1300 may comprise processing 1310 the collected 1308 ostomy data to obtain processed ostomy data, and the processing 1310 of the ostomy data may be based on a processing scheme, wherein the processing scheme may be based on the obtained 1306 one or more parameters. The processed 1310 ostomy data may be stored 1312a, e.g. in memory of the monitor device. The obtained 1306 one or more parameters and/or the collected 1308 ostomy data may also be stored 1312a. Alternatively or additionally, the processed 1310 ostomy data may be transmitted 1312b, e.g. to a remote device, such as an accessory device and/or a remote server. The obtained 1306 one or more parameters and/or the collected 1308 ostomy data may also be transmitted 1312b.

Figure 19:
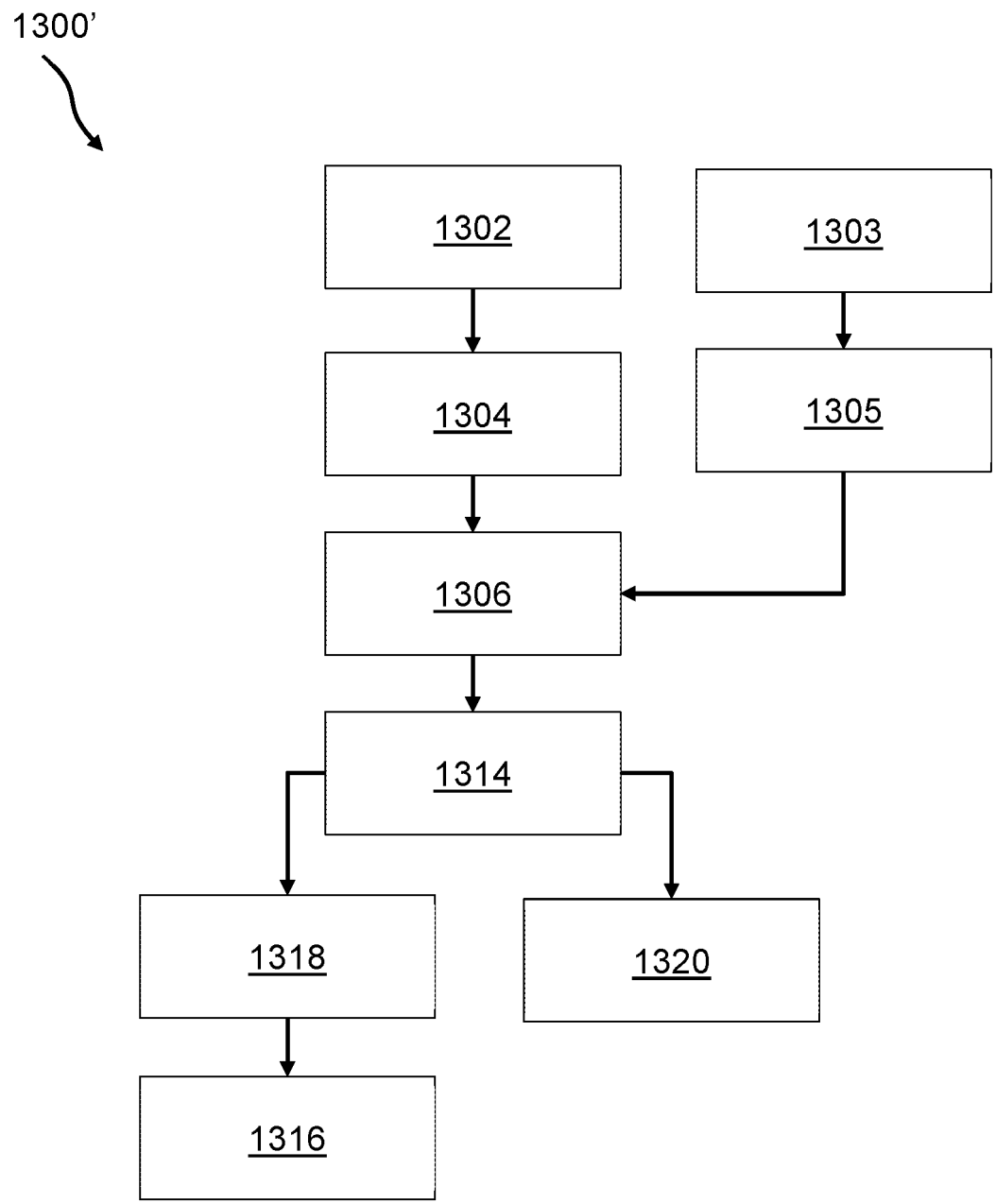
FIG. 19 is a flowchart of an exemplary method

FIG. 19 is a flowchart of an exemplary method 1300' for operating a monitor device, such as a monitor device 6 as described in relation to the previous figures, such as a monitor device configured to be connected to target device, such as a base plate of an ostomy appliance, a sensor assembly part of the base plate and/or a docking station, and wherein the target device has a monitor interface; and a first identifier element. The method 1300' comprises querying 1302 the first identifier element and receiving 1304 a first identifier response from the first identifier element, as described in relation to FIG. 18. The method 1300' may, as also described in more detail in relation to FIG. 18, comprise concurrent or sequential querying 1303 of other identifier elements and receiving 1305 identifier responses from the other identifier elements. The method 1300 further comprises obtaining 1306 one or more parameters based on the first identifier response and/or other identifier response(s), as described in relation to FIG. 18.

The method 1300' comprises determining 1314 if one or more operability criteria are satisfied based on the one or more parameters. For example, the one or more parameters may be indicative of an operating state of the target device. For example, the one or more parameters may be indicative of one or more of the electrodes being inoperable or of the monitor device not being fully connected, etc. Thus, the monitor device may be provided with certain minimum requirements for operating, and determining 1314 if one or more operability criteria are satisfied may comprise determining whether such requirements are met.

The method 1300' further comprises providing 1316 a first monitor device signal indicative of operating failure of the base plate and/or sensor assembly part if the one or more operability criteria are not being satisfied. The provided 1316 first monitor device signal may comprise an audible signal, a tactile signal, and/or a wireless signal to a remote device, such as an accessory device or a remote server.

The method 1300' may further comprise determining 1318 an operating failure type from a set of operating failure types. Thus, in providing 1316 the first monitor device signal, the first monitor device signal may be indicative of the operating failure type, i.e. the system and/or the user may be made aware of a likely cause of the operating failure. For example, the provided 1316 first monitor device signal may be indicative of a component of the ostomy appliance that is one or more of inoperative, damaged, defective, improperly connected, or improperly attached.

The method 1300' may further comprise providing 1320 a second monitor device signal indicative of correct operation of the base plate and/or the sensor assembly part. The second monitor device signal may be provided 1320 in accordance with the operability criteria being satisfied, such as based on that the determination 1314 of if the one or more operability criteria are satisfied has revealed that the operability criteria are satisfied. For example, the user may be provided with guidance of correct intended use of the target device when the target device is considered operable.

The method 1300' as illustrated in FIG. 19 may be combined with the method 1300 as illustrated in FIG. 18. Thus, a combined method may comprise all of the mentioned steps 1302-1322.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

First Exemplary Embodiments are set out in the Following First Items:

1. A base plate for an ostomy appliance, comprising:
    a first adhesive layer, including:
        a proximal surface configured to be attached to a skin surface of a user; and
        an stomal opening;
    an electrode assembly including a plurality of electrodes mounted with respect to the first adhesive layer, each electrode including:
        a sensing part arranged with respect to the stomal opening; and
        a connection part configured to electrically couple the sensing part to a monitor device; and
    one or more base plate identifier elements mounted with respect to the first adhesive layer, wherein each base plate identifier element is electrically coupled to at least two electrodes and represents base plate information that can be determined through the at least two electrodes to which the base plate identifier element is coupled.

2. The base plate of first item 1, wherein:
    the electrode assembly includes a ground electrode and a first electrode; and
    the one or more base plate identifier elements includes a first resistive element having a first resistance electrically connected between the ground electrode and the first electrode.

3. The base plate of first item 2, wherein the first resistive element is electrically connected to a sensing part of the first electrode.

4. The base plate of first item 2, wherein the first resistive element is electrically connected to a connection part of the first electrode.

5. The base plate of any of first items 1-4, wherein:
    the electrode assembly includes a second electrode; and
    the one or more base plate identifier elements further includes a second resistive element having a second resistance electrically connected between the second electrode and at least one of the ground electrode and the first electrode.

6. The base plate of first item 5, wherein the second resistive element is electrically connected to a sensing part of the second electrode.

7. The base plate of first item 5, wherein the second resistive element is electrically connected to a connection part of the second electrode.

8. The base plate of any of first items 5-7, wherein the second resistance is a measurably different resistance than the first resistance.

9. The base plate of any of first items 5-8, wherein:
the ground electrode includes:
   a first electrode part; and
   a second electrode part;
the first resistive element is connected between the first electrode and the first electrode part of the ground electrode; and
the second resistive element is connected between the second electrode and the second electrode part of the ground electrode.

10. The base plate of any of first items 5-9, wherein:
the electrode assembly further includes a third electrode; and
the one or more base plate identifier elements further includes a third resistive element having a third resistance electrically connected between the third electrode and at least one of the ground electrode, the first electrode, and the second electrode.

11. The base plate of first item 10, wherein the third resistive element is electrically connected to a sensing part of the third electrode.

12. The base plate of first item 10, wherein the third resistive element is electrically connected to a connection part of the third electrode.

13. The base plate of any of first items 10-12, wherein the third resistance is a measurably different resistance than the first and second resistances.

14. The base plate of any of first items 10-13, wherein:
the ground electrode further includes a third electrode part; and
the third resistive element is connected between the third electrode and the third electrode part of the ground electrode.

15. The base plate of first item 3, wherein the first resistive element is electrically connected proximate a distal end of the sensing parts of the first electrode to facilitate conductor integrity testing of the first electrode.

16. The base plate of any of first items 1-15, wherein the sensing part of each electrode extends circumferentially around at least a portion of the stomal opening.

17. The base plate of any of first items 1-15, wherein the sensing part of each electrode extends circumferentially and around substantially an entire perimeter of the stomal opening.

18. The base plate of any of first items 16-17, wherein the sensing parts of the plurality of electrodes are located at radially-spaced positions with respect to one another.

19. The base plate of any of first items 16-18, wherein:
the proximal surface of the first adhesive layer includes a cuttable region adjacent the stomal opening to facilitate sizing the stomal opening through the removal of all or a portion of the cuttable region, and the first adhesive layer further includes a noncuttable region surrounding the cuttable region; and
the one or more base plate identifier elements are located in the noncuttable region.

20. The base plate of first item 19, wherein the sensing part of one or more of the plurality of electrodes is located within the cuttable region.

21. The base plate of any of first items 1-20, wherein the connection parts of the electrodes are positioned adjacent one another at a monitor interface location spaced apart from the sensing parts of the electrodes.

22. The base plate of any of first items 1-21, wherein:
the electrode assembly includes a ground electrode and a first electrode; and
the one or more base plate identifier elements includes a first capacitive element having a first capacitance electrically connected between the ground electrode and the first electrode.

23. The base plate of any of first items 1-22, wherein:
the electrode assembly includes a ground electrode and a first electrode; and
the one or more base plate identifier elements includes a circuit element configured to provide a multiple bit digital value.

24. The base plate of any of first items 1-23, wherein the one or more base plate identifier elements represents base plate information including one or more of base plate type, base plate manufacturing batch, base plate manufacture date and unique base plate identification.

25. A method for operating the base plate of any of first items 1-24, comprising:
receiving an electrical signal from two or more of the plurality of electrodes to which each base plate identifier element is coupled; and
altering characteristics of the received electrical signal by the base plate identifier element.

Second Exemplary Embodiments are set out in the Following Second Items:

1. A method for operating a monitor device configured to be connected to a base plate of an ostomy appliance, the base plate having an electrode assembly, comprising:
receiving base plate identification information from the ostomy appliance base plate; and
one or more of (1) transmitting, (2) storing or (3) processing the received base plate identification information.

2. The method of second item 1 wherein the method further includes:
determining a data collection scheme based on the base plate identification information;
collecting ostomy data representative of a condition of the ostomy appliance from the base plate based on the data collection scheme; and
one or more of (1) transmitting, (2) storing or (3) processing the collected ostomy data.

3. The method of second item 2 wherein determining the data collection scheme includes receiving the data collection scheme from an accessory device.

4. The method of any of second items 2-3 wherein determining the data collection scheme includes retrieving the data collection scheme from a memory of the monitor device.

5. The method of any of second items 2-4 wherein determining the data collection scheme includes selecting a data collection scheme from a plurality of data collection schemes including at least (1) a first data collection scheme that includes a first criteria set, and (2) a second data collection scheme that includes a second criteria set, and wherein the first criteria set and the second criteria set are different.

6. The method of any of second items 1-5 wherein the method further includes:
determining a processing scheme based on the base plate identification information;
receiving ostomy data representative of a condition of the ostomy appliance;
processing the ostomy data based on the determined data processing scheme to determine an operating state of the ostomy appliance; and
one or more of (1) storing or (2) transmitting the operating state.

7. The method of second item 6 wherein determining the processing scheme includes receiving the processing scheme from an accessory device.
8. The method of any of second items 6-7 wherein determining the processing scheme includes retrieving the processing scheme from a memory of the monitor device.
9. The method of an of second items 6-8 wherein processing the ostomy data based on the processing scheme includes processing the ostomy data to determine an operating state indicative of one or more of (1) adhesive performance of the ostomy appliance, (2) moisture level of an adhesive layer of the ostomy appliance, (3) electrical properties of the adhesive layer of the ostomy appliance, (4) moisture patterns of the base plate, (5) leakage state of the ostomy appliance, (6) leakage location, or (7) leakage risk of the ostomy appliance.
10. The method of any of second items 6-9 wherein determining the processing scheme includes determining one or more base plate operating state parameters.
11. The method of any of second items 6-10 wherein determining the processing scheme includes selecting a processing scheme from a plurality of processing schemes including at least (1) a first processing scheme that includes a first threshold set, and (2) a second processing scheme that includes a second threshold set, and wherein the first threshold set and the second threshold set are different.
12. The method of any of second items 1-11 wherein receiving the base plate identification information includes receiving one or more of (1) base plate type, (2) base plate manufacturing batch, (3) base plate manufacture date, or (4) unique base plate identifier.
13. The method of any of second items 1-12 wherein receiving the base plate identification information includes receiving information representative of one or more resistance values.
14. The method of any of second items 1-13 wherein the method further includes:
receiving ostomy data representative of a condition of the ostomy appliance from the base plate; and
transmitting to an accessory device one or both of (1) monitor data based on the ostomy data, or (2) the base plate identification information.
15. A monitor device of an ostomy system, the monitor device configured to be connected to a base plate of an ostomy appliance, the base plate having an electrode assembly, comprising:
a first interface including a plurality of terminals;
memory;
a second interface including a transceiver; and
a processor coupled to the first interface, memory and second interface, configured to:
  receive base plate identification information through the first interface; and
  one or more of (1) transmit the base plate identification information by the transceiver, (2) store the base plate identification information in the memory, or (3) process the base plate identification information.
16. The monitor device of second item 15 wherein the processor is configured to:
determine a data collection scheme based on the base plate identification information;
collect ostomy data representative of a condition of the ostomy appliance from the base plate based on the data collection scheme; and
one or more of (1) transmit the collected ostomy data by the transceiver, (2) store the collected ostomy data in the memory, or (3) process the collected ostomy data.
17. The monitor device of second item 16 wherein the processor is configured to determine the data collection scheme by receiving the data collection scheme through the transceiver.
18. The monitor device of any of second items 16-17 wherein: the data collection scheme is stored in the memory; and
the processor is configured to determine the data collection scheme by retrieving the data collection scheme from the memory.
19. The monitor device of any of second items 14-16 wherein the processor is configured to:
to select a data collection scheme from a plurality of data collection schemes including at least (1) a first data collection scheme that includes a first criteria set, and (2) a second data collection scheme that includes a second criteria set, and wherein the first criteria set and the second criteria set are different; and
control the collection of the ostomy data based on the selected data collection scheme.
20. The monitor device of any of second items 15-19 wherein the processor is configured to:
determine a processing scheme based on the base plate identification information;
receive ostomy data representative of a condition of the ostomy appliance through the first interface;
process the ostomy data based on the processing scheme to determine an operating state of the ostomy appliance; and
one or more of (1) store the operating state, or (2) transmit the operating state.
21. The monitor device of second item 20 wherein the processor is configured to determine the processing scheme by receiving the processing scheme through the transceiver.
22. The monitor device of any of second items 20-21 wherein: the processing scheme is stored in the memory; and
the processor is configured to determine the processing scheme by retrieving the processing scheme from the memory.
23. The monitor device of any of second items 20-22 wherein the processor is configured to process the ostomy data based on the processing scheme to determine an operating state indicative of one or more of (1) adhesive performance of the ostomy appliance, (2) moisture level of an adhesive layer of the ostomy appliance, (3) electrical properties of the adhesive layer of the ostomy appliance, (4) moisture patterns of the base plate, (5) leakage state of the ostomy appliance, (6) leakage location, or (7) leakage risk of the ostomy appliance.
24. The monitor device of any of second items 20-23 wherein the processor is configured to determine the processing scheme by determining one or more base plate operating state parameters.
25. The monitor device of any of second items 20-24 wherein the processor is configured to determine the processing scheme by selecting a processing scheme from a plurality of processing schemes including at least (1) a first processing scheme that includes a first threshold set, and (2) a second processing scheme that includes a second threshold set, and wherein the first threshold set and the second threshold set are different.

26. The monitor device of any of second items 15-25 wherein the processor is configured to receive base plate identification information representative of one or more of (1) base plate type, (2) base plate manufacturing batch, (3) base plate manufacture date, or (4) unique base plate identifier.

27. The monitor device of any of second items 15-26 wherein the processor is configured to receive the base plate identification information in the form of one or more resistance values.

28. The monitor device of any of second items 15-27 wherein the processor is configured to:
receive ostomy data representative of a condition of the ostomy appliance from the base plate; and
transmit to an accessory device by the transceiver one or both of (1) monitor data based on the ostomy data, or (2) the base plate identification information.

Third Exemplary Embodiments are set out in the Following Third Items:

1. A monitor device of an ostomy system including an ostomy appliance, comprising:
a processor;
a memory; and
a first interface configured for structural coupling to a base plate of the ostomy appliance; and
wherein the processor is configured to:
obtain one or more parameters indicative of an operating state of the monitor device and/or the base plate;
determine if one or more operability criteria are satisfied based on the one or more parameters; and
provide a first monitor device signal indicative of operating failure of the monitor device and/or the base plate if the one or more operability criteria are not being satisfied.

2. The monitor device according to third item 1, wherein the processor is configured to:
obtain the one or more parameters indicative of an operating state of the monitor device and/or the base plate including by obtaining a first resistor value indicative of a resistance between a first terminal pair of the first interface connected to a respective first terminal pair of the base plate; and
determine if the one or more operability criteria are satisfied based on the first resistor value.

3. The monitor device according to any of third items 1-2, wherein the processor is configured to:
obtain the one or more parameters indicative of an operating state of the monitor device and/or the base plate including by obtaining a first capacitor value indicative of a capacitance between a first terminal pair of the first interface connected to a respective first terminal pair of the base plate; and
determine if the one or more operability criteria are satisfied based on the first capacitor value.

4. The monitor device according to any of third items 1-3, wherein the processor is configured to:
obtain the one or more parameters indicative of an operating state of the monitor device and/or the base plate including by obtaining a second resistor value indicative of a resistance between a second terminal pair of the first interface connected to a respective second terminal pair of the base plate; and
determine if the one or more operability criteria are satisfied based on the second resistor value.

5. The monitor device according to any of third items 1-4, wherein the processor is configured to:
obtain the one or more parameters indicative of an operating state of the monitor device and/or the base plate including by obtaining a first resonance frequency value indicative of a resonance frequency between a terminal pair of the first interface connected to a respective terminal pair of the base plate; and
determine if the one or more operability criteria are satisfied based on the first resonance frequency value.

6. The monitor device according to any of third items 1-5, wherein the processor is configured to:
obtain the one or more parameters indicative of an operating state of the monitor device and/or the base plate including by obtaining a power parameter value indicative of a power capacity of a power unit of the monitor device; and
determine if the one or more operability criteria are satisfied based on the power parameter value.

7. The monitor device according to any of third items 1-6, wherein the processor is configured to:
obtain the one or more parameters indicative of an operating state of the monitor device and/or the base plate including by obtaining ostomy data from the base plate via the first interface during a time period that the base plate is applied to a skin surface of the user;
determine a base plate application parameter indicative of application quality based on the ostomy data; and
determine if the one or more operability criteria are satisfied based on the base plate application parameter.

8. The monitor device according to any of third items 1-7, wherein the processor is configured to:
obtain the one or more parameters indicative of an operating state of the monitor device and/or the base plate including by obtaining a connection parameter indicative of mechanical connection quality between the monitor device and the base plate; and
determine if the one or more operability criteria are satisfied based on the connection parameter.

9. The monitor device according to any of third items 1-8, wherein the processor is configured to determine an operating failure type from a set of operating failure types, and wherein the first monitor device signal is indicative of the operating failure type.

10. The monitor device according to any of third items 1-9, wherein the first monitor device signal indicates that a component of the ostomy appliance is one or more of inoperative, damaged, defective, improperly connected and/or improperly attached.

11. The monitor device according to any of third items 1-10, wherein the first monitor device signal is one or more of an audible signal, a tactile signal, or a wireless signal to an accessory device.

12. The monitor device according to any of third items 1-11, wherein the processor is configured to, in accordance with the operability criteria being satisfied, provide a second monitor device signal indicative of correct operation of the monitor device and/or the base plate.

13. The monitor device of third item 12, wherein the second monitor device signal is one or more of an audible signal, a tactile signal, or a wireless signal to an accessory device.

14. A method of operating a monitor device of an ostomy system to assess the operability of the monitor device and/or a base plate, comprising:
obtaining one or more parameters indicative of an operating state of the monitor device and/or the base plate;

determining if one or more operability criteria are satisfied based on the one or more parameters; and providing a first monitor device signal indicative of operating failure of the monitor device and/or the base plate if the one or more operability criteria are not being satisfied.

15. The method of third item 14, wherein:
    obtaining the one or more parameters indicative of an operating state of the monitor device and/or the base plate comprises obtaining a first resistor value indicative of a resistance between a first terminal pair of a first interface connected to a respective first terminal pair of the base plate; and
    determining if the one or more operability criteria are satisfied includes determining an operability criterion based on the first resistor value.

16. The method of any of third items 14-15, wherein:
    obtaining the one or more parameters indicative of an operating state of the monitor device and/or the base plate comprises obtaining a first capacitor value indicative of a capacitance between a first terminal pair of a first interface connected to a respective first terminal pair of the base plate; and
    determining if the one or more operability criteria are satisfied includes determining an operability criterion based on the first capacitor value.

17. The method of any of third items 14-16, wherein:
    obtaining the one or more parameters indicative of an operating state of the monitor device and/or the base plate comprises obtaining a second resistor value indicative of a resistance between a second terminal pair of the first interface connected to a respective second terminal pair of the base plate; and
    determining if the one or more operability criteria are satisfied includes determining an operability criterion based on the second resistor value.

18. The method of any of third items 14-17, wherein:
    obtaining the one or more parameters indicative of an operating state of the monitor device and/or the base plate comprises obtaining a first resonance frequency value indicative of a resonance frequency between a terminal pair of the first interface connected to a respective terminal pair of the base plate; and
    determining if the one or more operability criteria are satisfied includes determining an operability criterion based on the first resonance frequency value.

19. The method of any of third items 14-18, wherein:
    obtaining the one or more parameters indicative of an operating state of the monitor device and/or the base plate comprises obtaining a power parameter value indicative of a power capacity of a power unit of the monitor device; and
    determining if the one or more operability criteria are satisfied includes determining an operability criterion based on the power parameter value.

20. The method of any of third items 14-19, wherein:
    obtaining one or more parameters indicative of an operating state of the monitor device and/or the base plate comprises obtaining ostomy data from the base plate via the first interface during a time period that the base plate is applied to a skin surface of the user; and
    the method further includes determining a base plate application parameter indicative of application quality based on the ostomy data; and
    determining if the one or more operability criteria are satisfied includes determining an operability criterion based on the base plate application parameter.

21. The method of any of third items 14-20, wherein:
    obtaining the one or more parameters indicative of an operating state of the monitor device and/or the base plate comprises obtaining a connection parameter indicative of mechanical connection quality between the monitor device and the base plate; and
    determining if the one or more operability criteria are satisfied includes determining an operability criterion based on the connection parameter.

22. The method of any of third items 14-21, wherein:
    the method further includes determining an operating failure type from a set of operating failure types; and
    providing the first monitor device signal includes providing the first monitor device signal indicative of the operating failure type.

23. The method of any of third items 14-22, wherein the first monitor device signal is indicative of a component of the ostomy appliance that is one or more of inoperative, damaged, defective, improperly connected, or improperly attached.

24. The method of any of third items 14-23, wherein providing the first monitor device signal includes providing one or more of an audible signal, a tactile signal, or a wireless signal to an accessory device.

25. The method of any of third items 14-24 and further including, in accordance with the operability criteria being satisfied, providing a second monitor device signal indicative of correct operation of the monitor device and/or the base plate.

Fourth Exemplary Embodiments are set out in the Following Fourth Items:

1. A monitor device for an ostomy system, comprising:
    a first interface configured to couple the monitor device to a target device; and
    a coupling sensor configured to detect and/or identify a coupling element of the target device.

2. The monitor device of fourth item 1, wherein the coupling sensor is configured to generate (i) a coupled signal indicative of the monitor device being coupled to the target device, and/or (ii) an identification signal indicative of which target device is coupled to the monitor device.

3. The monitor device of fourth item 2, wherein the monitor device further comprises a processor configured to (i) receive the coupled signal, and/or (ii) receive the identification signal.

4. The monitor device of any of the preceding fourth items, wherein the target device is one of a plurality of base plates and/or docking stations.

5. The monitor device of any of the preceding fourth items, wherein the coupling sensor comprises a resistive sensor configured to measure a resistance of a target resistor of the coupling element.

6. The monitor device of fourth item 5, wherein the resistive sensor comprises a first resistive sensor terminal and a second resistive sensor terminal.

7. The monitor device of any of fourth items 5-6, wherein the resistive sensor is further configured to generate the coupled signal (i) when the resistance measured substantially matches a target resistance and/or (ii) when the resistance measured is larger than a threshold resistance.

8. The monitor device of any of fourth items 5-7, wherein the resistive sensor is further configured to generate the identification signal when the resistance measured by the resistive sensor substantially matches one of a plurality of reference resistances.

9. The monitor device of any of the preceding fourth items, wherein the coupling sensor comprises a Hall sensor configured to measure a magnetic flux density of a target magnet of the coupling element.

10. The monitor device of any of fourth items 9, wherein the Hall sensor is further configured to generate the coupled signal (i) when the magnetic flux density measured substantially matches a target magnetic flux density and/or (ii) when the magnetic flux density measured is larger than a threshold magnetic flux density.

11. The monitor device of any of fourth items 9-10, wherein the Hall sensor is further configured to generate the identification signal when the magnetic flux density measured by the Hall sensor substantially matches one of a plurality of reference magnetic flux densities.

12. The monitor device of any of the preceding fourth items, wherein the coupling sensor comprises a reed switch configured to be triggered by a turning magnet of the coupling element.

13. The monitor device of fourth item 12, wherein the reed switch is further configured to generate the coupled signal when the reed switch is triggered.

14. The monitor device of any of the preceding fourth items, wherein the coupling sensor comprises an inductive sensor configured to engage a metallic actuator of the coupling element.

15. The monitor device of fourth item 14, wherein the inductive sensor is further configured to generate the coupled signal when the inductive sensor engages the metallic actuator.

16. The monitor device of any of fourth items 14-15, wherein the inductive sensor detects the metallic actuator by detecting a change in oscillation amplitude in the inductive sensor resulted from the metallic actuator being sufficiently near the inductive sensor.

17. The monitor device of any of fourth items 14-16, wherein the inductive sensor generates the coupled signal when the change in oscillation amplitude substantially matches a target change in oscillation amplitude, the target change in oscillation amplitude corresponding to the change in oscillation amplitude measurable by the inductive sensor when the monitor device and the target device are coupled.

18. The monitor device of any of the preceding fourth items, wherein the coupling sensor comprises a capacitive sensor configured to engage a dielectric actuator of the coupling element.

19. The monitor device of fourth item 18, wherein the capacitive sensor is further configured to generate the coupled signal when the capacitive sensor engages the dielectric actuator.

20. The monitor device of any of fourth items 18-19, wherein the capacitive sensor detects the dielectric actuator by detecting a change in oscillation amplitude of the inductive sensor resulted from the dielectric actuator being sufficiently near the capacitive sensor.

21. The monitor device of any of fourth items 18-20, wherein the capacitive sensor generates the coupled signal when the change in oscillation amplitude substantially matches a target change in oscillation amplitude, the target change in oscillation amplitude corresponding to the change in oscillation amplitude measurable by the capacitive sensor when the monitor device and the target device are coupled.

22. The monitor device of any of the preceding fourth items, wherein the coupling sensor comprises an ultrasonic sensor including an emitter and a receiver, the ultra-sonic sensor configured to detect a sonic target of the coupling element.

23. The monitor device of fourth item 22, wherein the ultrasonic sensor is further configured to generate the coupled signal when the sonic target is detected.

24. The monitor device of any of fourth items 22-23, wherein the ultrasonic sensor is a diffuse ultrasonic sensor, a retro-reflective ultrasonic sensor, or a through-beam ultrasonic sensor.

25. The monitor device of any of the preceding fourth items, wherein the coupling sensor comprises a photoelectric sensor including an emitter and a receiver, the photoelectric sensor configured to detect a photonic target of the coupling element.

26. The monitor device of fourth item 25, wherein the photoelectric sensor is further configured to generate the coupled signal when the photonic target is detected.

27. The monitor device of any of fourth items 25-26, wherein the photoelectric sensor is a diffuse photoelectric sensor, a retro-reflective photoelectric sensor, or a through-beam photoelectric sensor.

28. The monitor device of any of the preceding fourth items, wherein the coupling sensor comprises a bar code reader configured to identify a reference bar code of the coupling element.

29. The monitor device of fourth item 28, wherein the bar code reader is further configured to generate the identification signal to be received by the processor of the monitor device when the reference bar code is identified.

30. The monitor device of any of the preceding fourth items, wherein the coupling sensor comprises a magnetic strip reader configured to identify a reference magnetic strip of the coupling element.

31. The monitor device of fourth item 30, wherein the magnetic strip reader is further configured to generate the identification signal to be received by the processor of the monitor device when the reference magnetic strip is identified.

32. The monitor device of any of the preceding fourth items, wherein the coupling sensor comprises an image ID reader configured to identify a reference image ID of the coupling element.

33. The monitor device of fourth item 32, wherein the image ID reader is further configured to generate the identification signal to be received by the processor of the monitor device when the reference image ID is identified.

34. The monitor device of any of the preceding fourth items, wherein the coupling sensor comprises a variable depth ID reader configured to identify a reference variable depth ID of the coupling element.

35. The monitor device of fourth item 34, wherein the variable depth ID reader is further configured to generate the identification signal to be received by the processor of the monitor device when the reference variable depth ID is identified.

36. The monitor device of any of the preceding fourth items, wherein the coupling sensor comprises a RFID reader configured to identify a reference RFID of the coupling element.

37. The monitor device of fourth item 36, wherein the RFID reader is further configured to generate the identification signal to be received by the processor of the monitor device when the reference RFID is identified.

38. The monitor device of any of the preceding fourth items, wherein the coupling sensor comprises a NFC tag reader configured to identify a reference NFC tag of the coupling element.

39. The monitor device of fourth item 38, wherein the NFC tag reader is further configured to generate the identification signal to be received by the processor of the monitor device when the NFC tag is identified.

40. A base plate for an ostomy system, comprising:
a monitor interface configured to couple the base plate to a monitor device for the ostomy system; and
a coupling element configured to be detected and/or identified by a coupling sensor of the monitor device for the ostomy system.

41. The base plate of fourth item 40, wherein the coupling element comprises at least one of a resistor, a magnet, a metallic actuator, a dielectric actuator, a sonic target, a photonic target, a bar code, a magnetic strip, an image ID, a variable depth ID, a RFID, and a NFC tag.

42. A docking station for an ostomy system, comprising:
a monitor interface configured to couple the docking station to a monitor device for the ostomy system; and
a coupling element configured to be detected and/or identified by a coupling sensor of the monitor device for the ostomy system.

43. The docking station of fourth item 42, wherein the coupling element comprises at least one of a resistor, a magnet, a metallic actuator, a dielectric actuator, a sonic target, a photonic target, a bar code, a magnetic strip, an image ID, a variable depth ID, a RFID, and a NFC tag.

Fifth Exemplary Embodiments are set out in the Following Fifth Items:

1. Sensor assembly part for a base plate of an ostomy system, the sensor assembly part comprising:
an electrode assembly including a plurality of electrodes, each electrode including a sensing part and a connection part, the connection part being configured to electrically couple the sensing part to a monitor device of the ostomy system;
a monitor interface configured to couple the sensor assembly part to the monitor device; and
a first identifier element configured to be queried by the monitor device.

2. Sensor assembly part according to fifth item 1, wherein the first identifier element comprises one or more of a resistor, a capacitive element, a magnet, a metallic actuator, a dielectric actuator, a sonic target, a pho-tonic target, a bar code, a magnetic strip, an image ID, a variable depth ID, and a circuit element, such as an RFID tag, and an NFC tag.

3. Sensor assembly part according to any of fifth items 1-2, wherein the first identifier element is electrically coupled to a first set of electrodes of the plurality of electrodes including a first electrode of the plurality of electrodes, such that the first identifier element can be queried through the first set of electrodes.

4. Sensor assembly part according to fifth item 3, wherein the first identifier element includes a first resistive element having a first resistance.

5. Sensor assembly part according to any of fifth items 3-4, wherein the first identifier element is electrically connected to the sensing part of the first electrode.

6. Sensor assembly part according to fifth item 5, wherein the sensing part of the first electrode extends from the connection part of the first electrode to a sensing part end of the first electrode, and wherein the first identifier element is electrically connected near the sensing part end of the sensing part of the first electrode.

7. Sensor assembly part according to any of fifth items 3-4, wherein the first identifier element is electrically connected to the connection part of the first electrode.

8. Sensor assembly part according to any of fifth items 4-7, wherein the plurality of electrodes includes a second electrode, and the sensor assembly part comprises a second identifier element configured to be queried by the monitor device, the second identifier element being electrically coupled to a second set of electrodes of the plurality of electrodes including a second electrode of the plurality of electrodes, such that the second identifier element can be queried through the second set of electrodes.

9. Sensor assembly part according to fifth item 8, wherein the first set of electrodes includes a common electrode of the plurality of electrodes, and wherein the second set of electrodes includes the common electrode, such as a third electrode and/or a ground electrode.

10. Sensor assembly part according to any of fifth items 8-9, wherein the second identifier element includes a second resistive element having a second resistance, wherein the second resistance is different from the first resistance.

11. Sensor assembly part according to any of fifth items 8-10, wherein the second identifier element is electrically connected to a sensing part of the second electrode.

12. Sensor assembly part according to fifth item 11, wherein the sensing part of the second electrode extends from the connection part of the second electrode to a sensing part end of the second electrode, and wherein the second identifier element is electrically connected near the sensing part end of the sensing part of the second electrode.

13. Sensor assembly part according to any of fifth items 8-10, wherein the second identifier element is electrically connected to a connection part of the second electrode.

14. Method for operating a monitor device configured to be connected to a base plate of an ostomy appliance, such as to a sensor assembly part of the base plate, the base plate and/or the sensor assembly part having an electrode assembly; a monitor interface; and a first identifier element, the method comprising:
querying the first identifier element;
receiving a first identifier response from the first identifier element; and
obtaining one or more parameters based on the first identifier response.

15. Method according to fifth item 14 comprising one or more of (1) transmitting, (2) storing or (3) processing the one or more parameters.

16. Method according to any of fifth items 14-15 wherein obtaining the one or more parameters includes transmitting a request signal based on the first identifier response to an accessory device and receiving the one or more parameters from the accessory device.

17. Method according to any of fifth items 14-16 wherein obtaining the one or more parameters includes retrieving the one or more parameters from a memory of the monitor device.

18. Method according to any of fifth items 14-17, wherein the one or more parameters are indicative of a data collection scheme, and wherein the method comprises:

collecting ostomy data representative of a condition of the ostomy appliance based on the data collection scheme; and transmitting, storing and/or processing the collected ostomy data.

19. Method according to any of fifth items 14-18, wherein the one or more parameters are indicative of a data processing scheme, and wherein the method comprises:

collecting ostomy data representative of a condition of the ostomy appliance;

processing the collected ostomy data based on the processing scheme to obtain processed ostomy data; and storing and/or transmitting the processed ostomy data.

20. Method according to any of fifth items 14-19, wherein the one or more parameters are indicative of one or more of (1) base plate type or sensor assembly part type, (2) base plate manufacturing batch or sensor assembly part manufacturing batch, (3) base plate manufacture date or sensor assembly part manufacturing date, or (4) unique base plate identifier or unique sensor assembly part identifier.

21. Method according to any of fifth items 14-20, wherein querying the first identifier element comprises measuring a first resistive value indicative of a resistance between a first terminal pair of the monitor interface, and wherein the first identifier response is the first resistive value.

22. Method according to any of fifth items 14-21, wherein querying the first identifier element comprises measuring a first capacitive value indicative of a capacitance between a first terminal pair of the monitor interface, and wherein the first identifier response is the first capacitive value.

23. Method according to any of fifth items 14-22, wherein querying the first identifier element comprises measuring a first resonance frequency value indicative of a resonance frequency between a terminal pair of the monitor interface, and wherein the first identifier response is the first resonance frequency value.

24. Method according to any of fifth items 14-23 comprising:

querying a second identifier element; and receiving a second identifier response from the second identifier element, and wherein obtaining the one or more parameters includes obtaining the one or more parameters based on the second identifier response.

25. Method according to fifth item 24, wherein querying the second identifier element comprises measuring a second resistive value indicative of a resistance between a second terminal pair of the monitor interface, and wherein the second identifier response is the second resistive value.

26. Method according to any of fifth items 24-25, wherein querying the second identifier element comprises measuring a second capacitive value indicative of a capacitance between a second terminal pair of the monitor interface, and wherein the second identifier response is the second capacitive value.

27. Method according to any of fifth items 14-26, wherein the one or more parameters are indicative of an operating state of the base plate and/or the sensor assembly part, and the method comprises:

determining if one or more operability criteria are satisfied based on the one or more parameters; and providing a first monitor device signal indicative of operating failure of the base plate and/or sensor assembly part if the one or more operability criteria are not being satisfied.

28. Method according to fifth item 27, comprising determining an operating failure type from a set of operating failure types; and providing the first monitor device signal includes providing the first monitor device signal indicative of the operating failure type.

29. Method according to any of fifth items 27-28, wherein the first monitor device signal is indicative of a component of the ostomy appliance that is one or more of inoperative, damaged, defective, improperly connected, or improperly attached.

30. Method according to any of fifth items 27-29, wherein providing the first monitor device signal includes providing one or more of an audible signal, a tactile signal, or a wireless signal to an accessory device.

31. Method according to any of fifth items 27-30 comprising in accordance with the operability criteria being satisfied, providing a second monitor device signal indicative of correct operation of the base plate and/or the sensor assembly part.

32. Method according to any of fifth items 14-31, wherein the one or more parameters are indicative of the monitor device being fully connected to the base plate and/or sensor assembly part.

33. A monitor device of an ostomy system, the monitor device configured to be connected to a base plate or a sensor assembly part of an ostomy appliance, the monitor device comprising:

a first interface including a plurality of terminals configured to be connected with respective terminals of a monitor interface of the base plate or sensor assembly;

memory;

a processor coupled to the first interface and memory, the processor being configured to perform the method of any of fifth items 14-32.

LIST OF REFERENCES 1 ostomy system
2 ostomy appliance
4 base plate
6 monitor device
8 accessory device
10 server device
12 network
14 coupling member
16 coupling ring
18 stoma-receiving opening
20 docking station
22 first connector
24 user interface
50 target device
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver 126 loudspeaker
128 haptic feedback element
140 sensor unit
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
218 masking element
218A distal surface of masking element
218B proximal surface of masking element
220 electrode configuration
222 ground electrode
222A ground connection part
222B ground sensing part
224 first electrode
224A first connection part
224B first sensing part
226 second electrode
226A second connection part
226B second sensing part
228 third electrode
228A third connection part
228B third sensing part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
320 electrode configuration
324 first electrode
324A first connection part
324B first sensing part
326 second electrode
326A second connection part
326B second sensing part
328 third electrode
328A third connection part
328B third sensing part
330 fourth electrode
330A fourth connection part
330B fourth sensing part
394 first base plate identifier element
395 second base plate identifier element
420 electrode configuration
430 fourth electrode
430A fourth connection part
430B fourth sensing part
432 fifth electrode
432A fifth connection part
432B fifth sensing part
450 stomal opening
452 maximum cut line
454 cuttable region
456 noncuttable region
494 first base plate identifier element
495 second base plate identifier element
496 third base plate identifier element
497 fourth base plate identifier element
498 fifth base plate identifier element
700 sensor assembly part
800 identifier sensor
816 identifier element
900 resistive sensor
902 target resistor
906 first resistive sensor terminal
908 second resistive sensor terminal
910 Hall sensor
912 target magnet
920 reed switch
922 turning magnet
930 inductive sensor 932 metallic actuator
940 capacitive sensor
942 dielectric actuator
950 ultrasonic sensor
950' diffuse ultrasonic sensor
950" retro-reflective ultrasonic sensor
950'" through-beam ultrasonic sensor
952 emitter
952' emitter of diffuse ultrasonic sensor
952" emitter of retro-reflective ultrasonic sensor
952'" emitter of through-beam ultrasonic sensor
954 receiver
954' receiver of diffuse ultrasonic sensor
954" receiver of retro-reflective ultrasonic sensor
954'" receiver of through-beam ultrasonic sensor
955 fixed reflector
958 sonic target
960 photoelectric sensor
960' diffuse photoelectric sensor
960" retro-reflective photoelectric sensor
960'" through-beam photoelectric sensor
962 emitter
962' emitter of diffuse photoelectric sensor
962" emitter of retro-reflective photoelectric sensor
962'" emitter of through-beam photoelectric sensor
964 receiver
964' receiver of diffuse photoelectric sensor
964" receiver of retro-reflective photoelectric sensor
964'" receiver of through-beam photoelectric sensor
965 fixed reflector
968 photonic target
970 bar code reader
972 reference bar code
974 magnetic strip reader
976 reference magnetic strip
978 image ID reader
980 reference image ID
982 variable depth ID reader
984 reference variable depth ID
986 RFID reader
988 reference RFID
990 NFC tag reader
992 reference NFC tag
1200 resistive element configuration
1204 first resistive element
1206 second resistive element
1208 third resistive element
1224 far end of first electrode
1226 far end of second electrode
1228 far end of third electrode

The invention claimed is:

1. A base plate of an ostomy system, the base plate comprising:
a first adhesive layer with a proximal side configured for attachment of the base plate to the skin surface of a user;
an electrode assembly including a plurality of electrodes, each electrode including a sensing part and a connection part, the connection part being configured to electrically couple the sensing part to a monitor device of the ostomy system;
a monitor interface configured to couple the base plate to the monitor device; and
a first identifier element electrically coupled to a first set of electrodes of the plurality of electrodes and configured to be queried by the monitor device through the first set of electrodes.

2. The base plate according to claim 1, wherein the first identifier element comprises one or more of a resistor, a capacitive element, a magnet, a metallic actuator, a dielectric actuator, a sonic target, a photonic target, a bar code, a magnetic strip, an image ID, a variable depth ID, and a circuit element, such as an RFID tag, and an NFC tag.

3. The base plate according to claim 1, wherein the first identifier element includes a first resistive element having a first resistance.

4. The base plate according to claim 3, wherein the plurality of electrodes includes a second electrode, and the base plate comprises a second identifier element configured to be queried by the monitor device, the second identifier element being electrically coupled to a second set of electrodes of the plurality of electrodes including a second electrode of the plurality of electrodes, such that the second identifier element can be queried through the second set of electrodes.

5. The base plate according to claim 4, wherein the first set of electrodes includes a common electrode of the plurality of electrodes, and wherein the second set of electrodes includes the common electrode, such as a third electrode and/or a ground electrode.

6. The base plate according to claim 4, wherein the second identifier element includes a second resistive element having a second resistance, wherein the second resistance is different from the first resistance.

7. The base plate according to claim 4, wherein the second identifier element is electrically connected to a sensing part of the second electrode.

8. The base plate according to claim 7, wherein the sensing part of the second electrode extends from the connection part of the second electrode to a sensing part end of the second electrode, and wherein the second identifier element is electrically connected near the sensing part end of the sensing part of the second electrode.

9. The base plate according to claim 4, wherein the second identifier element is electrically connected to a connection part of the second electrode.

10. The base plate according to claim 1, wherein the first identifier element is electrically connected to the sensing part of a first electrode of the first set of electrodes.

11. The base plate according to claim 10, wherein the sensing part of the first electrode extends from the connection part of the first electrode to a sensing part end of the first electrode, and wherein the first identifier element is electrically connected near the sensing part end of the sensing part of the first electrode.

12. The base plate according to claim 1, wherein the first identifier element is electrically connected to the connection part of a first electrode of the first set of electrodes.

13. A monitor device of an ostomy system, the monitor device configured to be connected to a base plate of an ostomy appliance, the monitor device comprising:
a first interface including a plurality of terminals configured to be connected with respective terminals of a monitor interface of the base plate, wherein a respective terminal of the base plate is electrically coupled to an identifier element of the base plate, thereby enabling the monitor device to query the identifier element via the first interface;
memory; and
a processor coupled to the first interface and memory, the processor being configured to perform a set of operations, comprising:
querying, via the first interface, the identifier element of the base plate;

receiving, from the identifier element of the base plate, a first identifier response; and obtaining one or more parameters based on the first identifier response.

14. The monitor device of claim 13, wherein querying the identifier element comprises determining a resistance of the identifier element.

15. The monitor device of claim 13, wherein the identifier element comprises one or more of a resistor, a capacitive element, a magnet, a metallic actuator, a dielectric actuator, a sonic target, a photonic target, a bar code, a magnetic strip, an image ID, a variable depth ID, and a circuit element, such as an RFID tag, and an NFC tag.

16. The monitor device of claim 13, wherein:

the identifier element is a first identifier element; and the base plate further comprises a second identifier element that is electrically coupled to a terminal of the respective terminals of the monitor interface of the base plate, thereby enabling the monitor device to query the second identifier element via the first interface.

17. The monitor device of claim 16, wherein the monitor device is configured to query both the first identifier element and the second identifier element using a common terminal of the plurality of terminals.

18. The monitor device of claim 16, wherein querying the second identifier element comprises determining a resistance of the second identifier element.

19. The monitor device of claim 16, wherein the second identifier element comprises one or more of a resistor, a capacitive element, a magnet, a metallic actuator, a dielectric actuator, a sonic target, a photonic target, a bar code, a magnetic strip, an image ID, a variable depth ID, and a circuit element, such as an RFID tag, and an NFC tag.

20. The monitor device of claim 13, wherein obtaining the one or more parameters comprises determining a parameter of the one or more parameters from the memory of the monitor device based on the first identifier response.

* * * * *